United States Patent
Almsick et al.

(10) Patent No.: US 9,035,067 B2
(45) Date of Patent: May 19, 2015

(54) N-(1,2,5-OXADIAZOL-3-YL)-, N-(TETRAZOL-5-YL)- AND N-(TRIAZOL-5-YL)BICYCLOARYLCARBOXAMIDES AND THEIR USE AS HERBICIDES

(75) Inventors: Andreas Almsick, Karben (DE); Hartmut Ahrens, Egelsbach (DE); Arnim Köhn, Klein-Winternheim (DE); Simon Dörner-Rieping, Neu-Anspach (DE); Ralf Braun, Ramberg (DE); Isolde Häuser-Hahn, Leverkusen (DE); Christopher Hugh Rosinger, Hofheim am Taunus (DE); Ines Heinemann, Hofheim (DE); Elmar Gatzweiler, Bad Nauheim (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/005,246

(22) PCT Filed: Mar. 12, 2012

(86) PCT No.: PCT/EP2012/054269
§ 371 (c)(1),
(2), (4) Date: Dec. 20, 2013

(87) PCT Pub. No.: WO2012/123409
PCT Pub. Date: Sep. 20, 2012

(65) Prior Publication Data
US 2014/0106969 A1      Apr. 17, 2014

(30) Foreign Application Priority Data
Mar. 15, 2011   (EP) ..................... 11158258

(51) Int. Cl.
| | | |
|---|---|---|
| *A01N 43/707* | (2006.01) | |
| *A01N 43/713* | (2006.01) | |
| *A01N 43/82* | (2006.01) | |
| *C07D 249/08* | (2006.01) | |
| *C07D 271/04* | (2006.01) | |
| *A01N 43/653* | (2006.01) | |
| *C07D 409/12* | (2006.01) | |
| *C07D 409/14* | (2006.01) | |
| *C07D 411/12* | (2006.01) | |
| *C07D 413/12* | (2006.01) | |
| *C07D 413/14* | (2006.01) | |
| *C07D 417/12* | (2006.01) | |

(52) U.S. Cl.
CPC ............ *A01N 43/653* (2013.01); *C07D 271/04* (2013.01); *A01N 43/707* (2013.01); *C07D 249/08* (2013.01); *C07D 409/12* (2013.01); *C07D 409/14* (2013.01); *C07D 411/12* (2013.01); *C07D 413/12* (2013.01); *C07D 413/14* (2013.01); *C07D 417/12* (2013.01); *A01N 43/713* (2013.01); *A01N 43/82* (2013.01)

(58) Field of Classification Search
CPC .. C07D 249/08; C07D 271/04; A01N 43/707; A01N 43/713; A01N 43/82
USPC ........ 514/364, 382, 383; 548/125, 251, 265.4
See application file for complete search history.

(56) References Cited

U.S. PATENT DOCUMENTS

| 4,432,986 A * | 2/1984 | Erickson .................. 514/382 |
| 2011/0152084 A1 | 6/2011 | Kohn et al. |

FOREIGN PATENT DOCUMENTS

| EP | 0 173 657 A3 | 3/1986 |
| EP | 0173657 | 3/1986 |
| WO | 03/010143 A1 | 2/2003 |
| WO | 03010143 | 2/2003 |
| WO | 03010153 | 2/2003 |
| WO | 2004/101532 A1 | 11/2004 |
| WO | 2004101532 | 11/2004 |
| WO | 2011/035874 A1 | 3/2011 |
| WO | 2012/123409 A1 | 9/2012 |

OTHER PUBLICATIONS

Rao, Der Pharmacia Lettre, 2012, vol. 4, No. 2, p. 620-625.*
PubChem compound CID 62306, create date Mar. 28, 2005 [online], retrived from the internet on Sep. 23, 2014. URL; http://pubchem.ncbi.nlm.nih.gov/assay/assay.cgi?cid=62306.*
Komarova et al, FASEB, 2005, p. 1-21.*
International Search Report for PCT/EP2012/054269 Mailed May 11, 2012.
European Search Report dated Jul. 22, 2011, issued in counterpart German Application No. 11 15 8258.1.
International Search Report dated May 3, 2012, issued in counterpart European Application No. 2012*054269.

* cited by examiner

*Primary Examiner* — Rebecca Anderson
*Assistant Examiner* — Karen Cheng
(74) *Attorney, Agent, or Firm* — Miles and Stockbridge

(57) ABSTRACT

N-(1,2,5-Oxadiazol-3-yl)-, N-(tetrazol-5-yl)- and N-(triazol-5-yl)bicycloarylcarboxamides of the general formula (I) are described as herbicides.

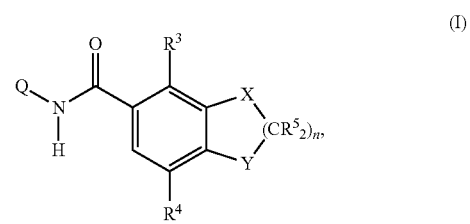

In this formula (I), $R^3$, $R^4$ and $R^5$ are each radicals such as hydrogen, organic radicals such as alkyl, and other radicals such as halogen. Q is a heterocycle. X and Y are each oxygen and sulfur.

18 Claims, No Drawings

N-(1,2,5-OXADIAZOL-3-YL)-, N-(TETRAZOL-5-YL)- AND N-(TRIAZOL-5-YL)BICYCLOARYLCAR-BOXAMIDES AND THEIR USE AS HERBICIDES

CROSS REFERENCE TO RELATED APPLICATIONS

This application is a §371 National Stage Application of PCT/EP2012/054269, filed Mar. 12, 2012, which claims priority to European Application No. 11158258.1, filed Mar. 15, 2011.

BACKGROUND OF THE INVENTION

1. Field of the Invention
2. Description of Related Art

The invention relates to the technical field of herbicides, especially that of herbicides for selective control of broad-leaved weeds and weed grasses in crops of useful plants.

WO2003/010143 and WO2003/010153 disclose particular N-(tetrazol-5-yl)- and N-(triazol-5-yl)benzamides and the pharmacological action thereof. Under CAS No. 639048-78-5, the compound N-(1-propyltetrazol-5-yl)-2,5-dichlorobenzamide is known. No herbicidal action of these compounds is disclosed in these documents. European patent applications No. 0912169.0 and No. 10174893.7, which have earlier priority dates but were yet to be published at the priority date of the present application, disclose N-(1,2,5-oxadiazol-3-yl)-, N-(tetrazol-5-yl)- and N-(triazol-5-yl)arylcarboxamides and the use thereof as herbicides.

SUMMARY

It has now been found that N-(1,2,5-oxadiazol-3-yl)-, N-(tetrazol-5-yl)- and N-(triazol-5-yl)bicycloarylcarboxamides are of good suitability as herbicides.

The present invention thus provides N-(1,2,5-oxadiazol-3-yl)-, N-(tetrazol-5-yl)- or N-(triazol-5-yl)bicycloarylcarboxamides of the formula (I) or salts thereof

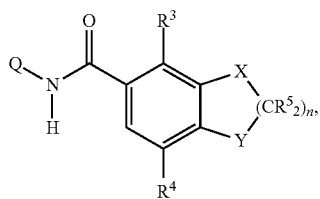

(I)

in which
Q is a Q1, Q2 or Q3 radical,

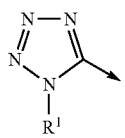

(Q1)

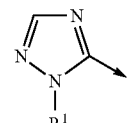

(Q2)

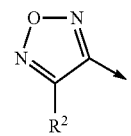

(Q3)

$R^1$ is $(C_1-C_6)$-alkyl, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_1-C_6)$-alkoxy-$(C_1-C_6)$-alkyl, $(C_1-C_6)$-alkoxy-$(C_2-C_6)$-alkenyl, $(C_1-C_6)$-alkoxy-$(C_2-C_6)$-alkynyl, $CH_2R^6$, heteroaryl, heterocyclyl or phenyl, where the three latter radicals are each substituted by u radicals from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkylthio, $(C_1-C_6)$-alkylsulfinyl, $(C_1-C_6)$-alkylsulfonyl, $(C_1-C_6)$-alkoxy, halo-$(C_1-C_6)$-alkoxy and $(C_1-C_6)$-alkoxy-$(C_1-C_4)$-alkyl;

$R^2$ is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, halo-$(C_2-C_6)$-alkenyl, $(C_2-C_6)$-alkynyl, $(C_2-C_6)$-alkynyloxy, halo-$(C_2-C_6)$-alkynyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl each substituted by u radicals from the group consisting of methyl, ethyl, methoxy, trifluoromethyl and halogen;

$R^3$ and $R^4$ are each independently hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, $(C_3-C_7)$-halocycloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_1-C_6)$-alkoxy-$(C_1-C_4)$-alkyl, halogen, nitro or cyano;

$R^5$ is hydrogen or fluorine;

$R^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_3-C_6)$-cycloalkyl, or heteroaryl, heterocyclyl or phenyl each substituted by u radicals from the group consisting of methyl, ethyl, methoxy, trifluoromethyl and halogen;

$R^7$ and $R^8$ are each independently hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, halo-$(C_3-C_7)$-cycloalkyl, —$OR^9$, $S(O)_mR^9$, $(C_1-C_6)$-alkylthio, halo-$(C_1-C_6)$-alkylthio, $(C_1-C_6)$-alkylsulfinyl, halo-$(C_1-C_6)$-alkylsulfinyl, $(C_1-C_6)$-alkylsulfonyl, halo-$(C_1-C_6)$-alkylsulfonyl, $(C_1-C_6)$-alkoxy-$(C_1-C_4)$-alkyl, halogen, nitro, cyano, heteroaryl, heterocyclyl or phenyl, where the three latter radicals are each substituted by u radicals from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkylthio, $(C_1-C_6)$-alkylsulfinyl, $(C_1-C_6)$-alkylsulfonyl, $(C_1-C_6)$-alkoxy, halo-$(C_1-C_6)$-alkoxy and $(C_1-C_6)$-alkoxy-$(C_1-C_4)$-alkyl, or $R^7$ and $R^8$ together with the carbon atom to which they are bonded form the —$X^1$—$(CH_2)_r$—$X^2$—, —$(CH_2)_s$—$X^3$—, —$(CH_2)_t$—$X^3$—$CH_2$—, —$(CH_2)_v$—$X^3$—$CH_2CH_2$— or —$(CH_2)_w$— unit in which each of the ($CH_2$) groups is substituted by m radicals from the group consisting of halogen, methyl and $(C_1-C_3)$-alkoxy, or $R^7$ and $R^8$ together with the carbon atom to which they are bonded form the —O—N($(C_1-C_3)$-alkyl)-$CHR^{10}$—$CH_2$— or —O—N=$CR^{10}$—$CH_2$— unit in which each of the ($CH_2$) groups is substituted by m radicals from the group consisting of halogen and methyl;

$R^9$ is hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, $(C_3-C_7)$-halocycloalkyl, $(C_3-C_7)$-cycloalkyl-$(C_1-C_3)$-alkyl, halo-$(C_3-C_7)$-cycloalkyl-$(C_1-C_3)$-alkyl, heteroaryl, heterocyclyl or phenyl, where the three latter radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkylthio, $(C_1-C_6)$-alkylsulfinyl, $(C_1-C_6)$-alkylsulfonyl, $(C_1-C_6)$-alkoxy, halo-$(C_1-C_6)$-alkoxy and $(C_1-C_6)$-alkoxy-$(C_1-C_4)$-alkyl;

$R^{10}$ is hydrogen, $(C_1-C_3)$-alkyl, or phenyl substituted by u radicals from the group consisting of $(C_1-C_3)$-alkyl, halogen, cyano and nitro;

$R^{11}$ is hydrogen, $(C_1-C_6)$-alkyl, $(C_2-C_6)$-alkenyl, $(C_2-C_6)$-alkynyl, formyl, $(C_2-C_6)$-alkylcarbonyl, $(C_2-C_6)$-alkoxycarbonyl or $(C_1-C_2)$-alkylsulfonyl;

X and Y are each independently O, S, SO, $SO_2$, $NR^{10}$, $CR^7R^8$, C=O, C=S, C=$NOR^{10}$ or C=NN$(R^{11})_2$;

$X^1$ and $X^2$ are each independently O, S or N($(C_1-C_3)$-alkyl);

$X^3$ is O or S;

m is 0, 1 or 2;

n is 1, 2 or 3;

r is 2, 3 or 4;

s is 2, 3, 4 or 5;

t is 1, 2, 3 or 4;

u is 0, 1, 2 or 3;

v is 2 or 3;

w is 2, 3, 4, 5 or 6.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. Halogen is fluorine, chlorine, bromine or iodine.

Heterocyclyl is a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl, Heteroaryl is an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned.

According to the nature and the bonding of the substituents, the compounds of the general formula (I) may be present as stereoisomers. When, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is equally possible to selectively prepare stereoisomers by using stereoselective reactions using optically active starting materials and/or auxiliaries. The invention also relates to all stereoisomers and mixtures thereof which are encompassed by the general formula (I) but not defined specifically.

Preference is given to compounds of the general formula (I) in which $R^1$ is $(C_1-C_3)$-alkyl, $(C_3-C_5)$-cycloalkyl, halo-$(C_1-C_3)$-alkyl or $(C_1-C_3)$-alkoxy-$(C_1-C_3)$-alkyl;

$R^2$ is hydrogen, $(C_1-C_3)$-alkyl, $(C_3-C_5)$-cycloalkyl, halo-$(C_1-C_3)$-alkyl, $(C_1-C_3)$-alkoxy, halo-$(C_1-C_3)$-alkoxy, cyano, nitro, methylsulfenyl, methylsulfinyl, methylsulfonyl, acetylamino, methoxycarbonyl, ethoxycarbonyl, halogen, amino, aminocarbonyl, methylaminocarbonyl, dimethylaminocarbonyl or methoxymethyl;

$R^3$ and $R^4$ are each independently hydrogen, $(C_1-C_3)$-alkyl, halo-$(C_1-C_3)$-alkyl, $(C_3-C_5)$-cycloalkyl, $(C_1-C_3)$-alkoxy, $(C_1-C_3)$-haloalkoxy, $(C_1-C_6)$-alkylthio, $(C_1-C_6)$-alkylsulfinyl, $(C_1-C_6)$-alkylsulfonyl, $(C_1-C_6)$-alkoxy-$(C_1-C_4)$-alkyl, halogen, nitro or cyano;

$R^5$ is hydrogen;

$R^7$ and $R^8$ are each independently hydrogen, $(C_1-C_3)$-alkyl, halo-$(C_1-C_3)$-alkyl, $(C_3-C_5)$-cycloalkyl, —$OR^9$, —S(O)$_m R^9$, $(C_1-C_3)$-alkylthio, $(C_1-C_3)$-alkylsulfinyl, $(C_1-C_3)$-alkylsulfonyl, $(C_1-C_3)$-alkoxy-$(C_1-C_3)$-alkyl, halogen, nitro, cyano, heteroaryl, heterocyclyl or phenyl, where the three latter radicals are each substituted by u radicals from the group consisting of halogen, nitro, cyano, $(C_1-C_3)$-alkyl, halo-$(C_1-C_3)$-alkyl, $(C_3-C_5)$-cycloalkyl, $(C_1-C_3)$-alkylthio, $(C_1-C_3)$-alkylsulfinyl, $(C_1-C_3)$-alkylsulfonyl, $(C_1-C_3)$-alkoxy, halo-$(C_1-C_3)$-alkoxy and $(C_1-C_3)$-alkoxy-$(C_1-C_3)$-alkyl, or $R^7$ and $R^8$ together with the carbon atom to which they are bonded form the —$X^1$—$(CH_2)_r$—$X^2$—, —$(CH_2)_s$—$X^3$—, —$(CH_2)_t$—$X^3$—$CH_2$—, —$(CH_2)_v$—$X^3$—$CH_2CH_2$— or —$(CH_2)_w$— unit in which each of the ($CH_2$) groups is substituted by m radicals from the group consisting of halogen, methyl and $(C_1-C_3)$-alkoxy, or $R^7$ and $R^8$ together with the carbon atom to which they are bonded form the—O—N($(C_1-C_3)$-alkyl)-$CHR^{10}$—$CH_2$— or —O—N=$CR^{10}$—$CH_2$— unit in which each of the ($CH_2$) groups is substituted by m radicals from the group consisting of halogen and methyl;

$R^9$ is hydrogen, $(C_1-C_3)$-alkyl, halo-$(C_1-C_3)$-alkyl, $(C_2-C_3)$-alkenyl, $(C_2-C_4)$-alkynyl, $(C_3-C_5)$-cycloalkyl, $(C_3-C_5)$-cycloalkyl-$(C_1-C_3)$-alkyl, heteroaryl, heterocyclyl or phenyl, where the three latter radicals are each substituted by s radicals from the group consisting of halogen, nitro, cyano, $(C_1-C_3)$-alkyl, halo-$(C_1-C_3)$-alkyl, $(C_3-C_6)$-cycloalkyl, $(C_1-C_3)$-alkylthio, $(C_1-C_3)$-alkylsulfinyl, $(C_1-C_3)$-alkylsulfonyl, $(C_1-C_3)$-alkoxy, halo-$(C_1-C_3)$-alkoxy and $(C_1-C_3)$-alkoxy-$(C_1-C_3)$-alkyl;

$R^{10}$ is hydrogen or $(C_1-C_3)$-alkyl;

X and Y are each independently O, $SO_2$, C=O, C=S, $CR^7R^8$, C=$NOR^{10}$;

$X^1$ and $X^2$ are each independently O, S, N($CH_3$);

$X^3$ is O or S;

m is 0, 1 or 2;

n is 1 or 2;

r is 2 or 3;

s is 2, 3 or 4;

t is 1, 2 or 3;

u is 0, 1 or 2;

v is 2 or 3;

w is 2, 3, 4 or 5.

In all the formulae specified hereinafter, the substituents and symbols have the same definition as in formula (I), unless defined differently.

Inventive compounds in which Q is Q1 or Q2 can be prepared, for example, by the method shown in scheme 1, by base-catalyzed reaction of a bicyclic benzoyl chloride (II) with a 5-amino-1H-1,2,4-triazole or 5-amino-1H-tetrazole (III):

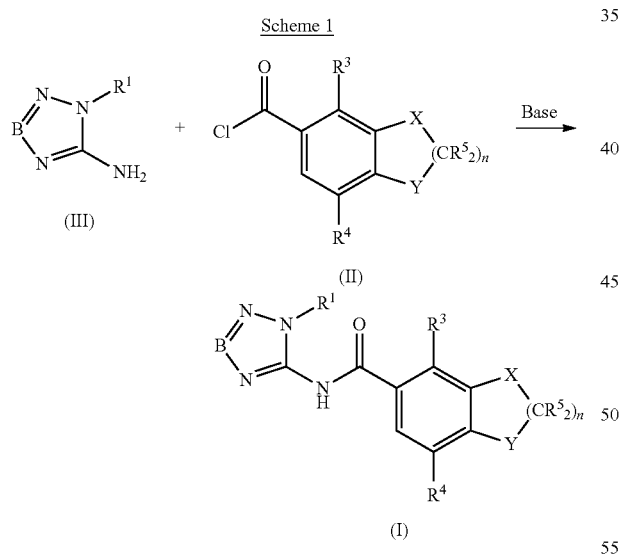

B therein is CH or N. The bicyclic benzoyl chlorides of the formula (II) or their parent bicyclic benzoic acids are known in principle and can be prepared, for example, by the methods known in WO 96/25413, WO 97/09324, WO 97/30993, WO 97/08164, WO 98/49159, WO 98/35954, WO 98/12192, WO 0014087 and EP 0636622.

Inventive compounds in which Q is Q1 or Q2 can also be prepared by the method shown in scheme 2, by reaction of a benzoic acid of the formula (IV) with a 5-amino-1H-1,2,4-triazole or 5-amino-1H-tetrazole (III):

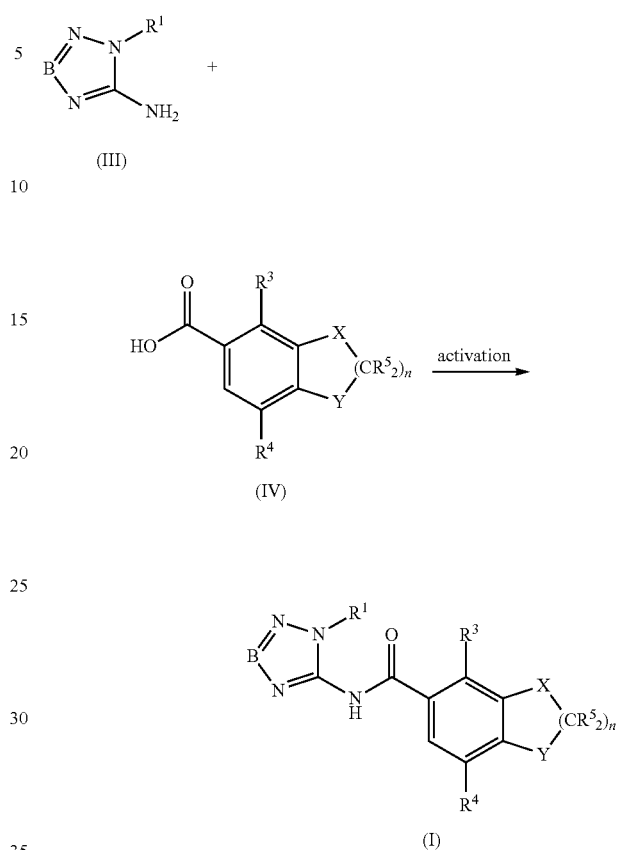

For the activation, it is possible to use dehydrating reagents which are typically used for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) etc.

Inventive compounds in which Q is Q1 or Q2 can also be prepared by the method shown in scheme 3, by reaction of an N-(1H-1,2,4-triazol-5-yl)benzamide, N-(1H-tetrazol-5-yl)benzamide, N-(1H-1,2,4-triazol-5-yl)nicotinamide or N-(1H-tetrazol-5-yl)nicotinamide:

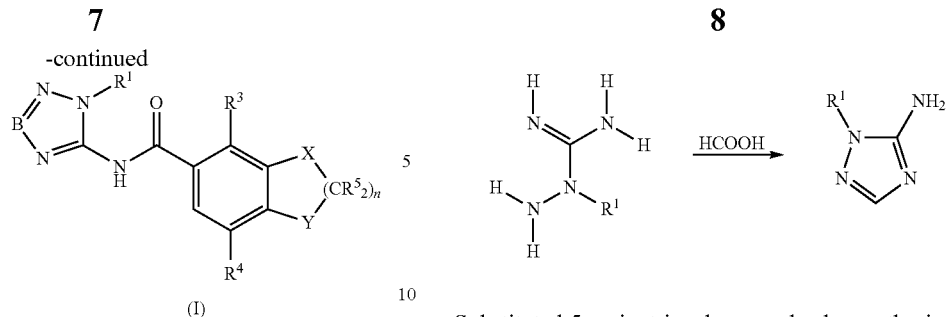

(I)

For this reaction shown in scheme 3, it is possible, for example, to use alkylating agents, for example alkyl halides or sulfonates or dialkyl sulfates, in the presence of a base.

It may be appropriate to alter the sequence of reaction steps. For instance, benzoic acids bearing a sulfoxide cannot be converted directly to their acid chlorides. One option here is first to prepare the amide to the thioether stage and then to oxidize the thioether to the sulfoxide.

The 5-amino-1H-tetrazoles of the formula (III) are either commercially available or can be prepared analogously to methods known from the literature. For example, substituted 5-aminotetrazoles can be prepared from aminotetrazole by the method described in Journal of the American Chemical Society (1954), 76, 923-924:

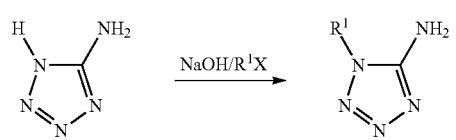

In the above reaction, X is a leaving group such as iodine. Substituted 5-aminotetrazoles can also be synthesized, for example, as described in Journal of the American Chemical Society (1954) 76, 88-89:

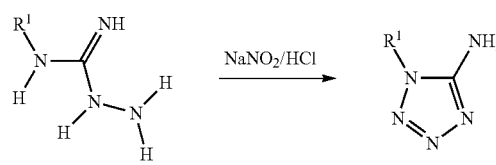

The 5-amino-1H-triazoles of the formula (III) are either commercially available or can be prepared analogously to methods known from the literature. For example, substituted 5-aminotriazoles can be prepared from aminotriazole by the method described in Zeitschrift füer Chemie (1990), 30(12), 436-437:

Substituted 5-aminotriazoles can also be synthesized, for example, as described in Chemische Berichte (1964), 97(2), 396-404:

Substituted 5-aminotriazoles can also be synthesized, for example, as described in Angewandte Chemie (1963), 75, 918:

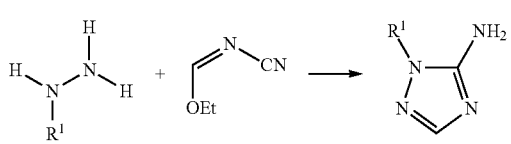

Inventive compounds in which Q is Q3 can be prepared, for example, by the method shown in scheme 4, by base-catalyzed reaction of a bicyclic benzoyl chloride (II) with a 4-amino-1,2,5-oxadiazole (VI):

Scheme 4

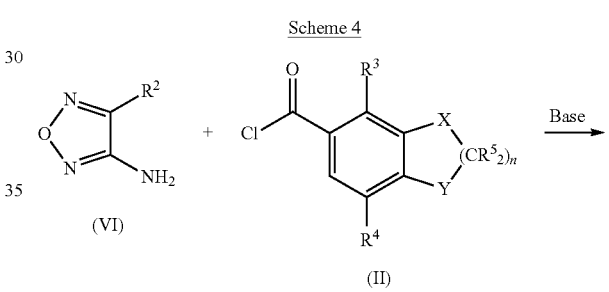

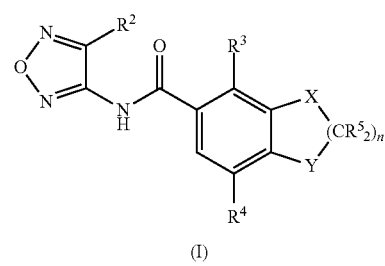

(I)

Inventive compounds can also be prepared by the method described in scheme 5, by reacting a bicyclic benzoic acid of the formula (IV) with a 4-amino-1,2,5-oxadiazole (VI):

Scheme 5

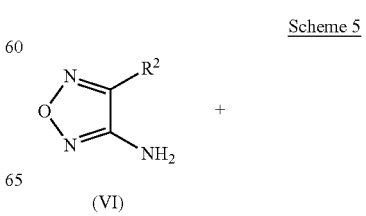

(VI)

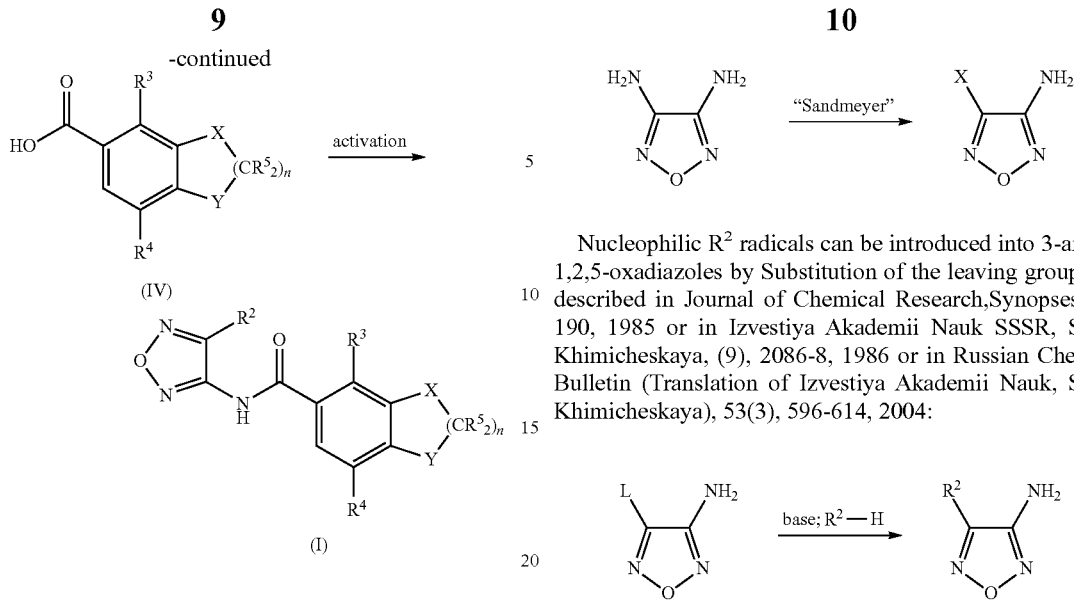

For the activation, it is possible to use dehydrating reagents which are typically used for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) etc.

The 4-amino-1,2,5-oxadiazoles of the formula (VI) are either commercially available or known, or can be prepared analogously to methods known from the literature. For example, 3-alkyl-4-amino-1,2,5-oxadiazoles can be prepared from β-keto esters by the method described in Russian Chemical Bulletin, Int. Ed., vol. 54, 4, p. 1032-1037 (2005):

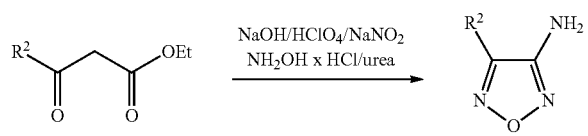

3-Aryl-4-amino-1,2,5-oxadiazoles can be synthesized, for example, as described in Russian Chemical Bulletin, 54(4), 1057-1059, (2005) or Indian Journal of Chemistry, Section B: Organic Chemistry Including Medicinal Chemistry, 26B(7), 690-2, (1987):

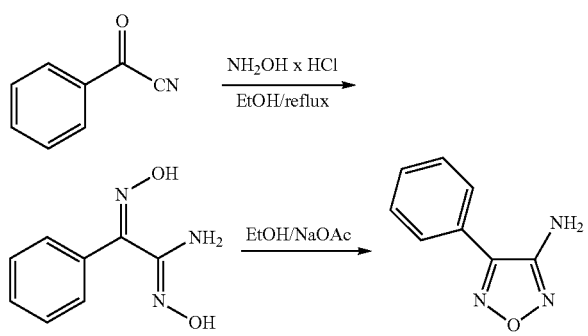

3-Amino-4-halo-1,2,5-oxadiazoles can be prepared, for example, by a Sandmeyer reaction from the commercially available 3,4-diamino-1,2,5-oxadiazole by the method described in Heteroatom Chemistry 15(3), 199-207 (2004):

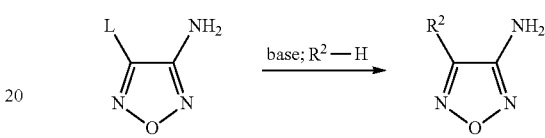

Nucleophilic $R^2$ radicals can be introduced into 3-amino-1,2,5-oxadiazoles by Substitution of the leaving group L as described in Journal of Chemical Research,Synopses, (6), 190, 1985 or in Izvestiya Akademii Nauk SSSR, Seriya Khimicheskaya, (9), 2086-8, 1986 or in Russian Chemical Bulletin (Translation of Izvestiya Akademii Nauk, Seriya Khimicheskaya), 53(3), 596-614, 2004:

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from Perkin Elmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The technical literature describes a number of experimental protocols, for example ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid-phase supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Either on a solid phase or in the liquid phase, the performance of single or multiple synthesis steps can be supported by the use of microwave technology. The technical literature describes a number of experimental protocols, for example Microwaves in Organic and Medicinal Chemistry (editors: C. O. Kappe and A. Stadler), Wiley, 2005.

The preparation by the process described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), collectively referred to hereinafter as "inventive compounds", have excellent herbicidal efficacy against a broad spectrum of economically important monocotyledonous and dicotyledonous annual harmful plants. The active ingredients also have good control over perennial weed plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the inventive compounds are applied to the soil surface before germination, either the weed seedlings are prevented completely from emerging or the weeds grow until they have reached the cotyledon stage, but then stop growing and, eventually, after three to four weeks have passed, die completely.

If the active ingredients are applied post-emergence to the green parts of the plants, there is likewise stoppage of growth after the treatment, and the harmful plants remain at the growth stage of the time of application, or they die completely after a certain time, such that competition by the weeds, which is harmful to the crop plants, is thus eliminated very early and in a lasting manner.

Although the inventive compounds have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, especially *Zea* and *Triticum*, are damaged only to an insignificant extent, if at all, depending on the structure of the respective inventive compound and the application rate thereof. For these reasons, the present compounds are very suitable for selective control of unwanted plant growth in plant crops such as agriculturally useful plants or ornamentals.

In addition, the inventive compounds (depending on their particular structure and the application rate deployed) have outstanding growth-regulating properties in crop plants. They intervene in the plant's own metabolism with a regulatory effect, and can thus be used to control plant constituents and to facilitate harvesting, for example by triggering desiccation and stunted growth. In addition, they are also suitable for general control and inhibition of unwanted vegetative growth without killing the plants. Inhibiting vegetative growth plays a major role for many monocotyledonous and dicotyledonous crops, since, for example, this can reduce or completely prevent lodging.

By virtue of their herbicidal and plant growth-regulating properties, the active ingredients can also be used for control of harmful plants in crops of genetically modified plants or plants modified by conventional mutagenesis. In general, the transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

With regard to transgenic crops, preference is given to the use of the inventive compounds in economically important transgenic crops of useful plants and ornamentals, for example of cereals such as wheat, barley, rye, oats, millet/sorghum, rice and corn, or else crops of sugar beet, cotton, soybean, oilseed rape, potato, tomato, peas and other vegetables. Preferably, the inventive compounds can be used as herbicides in crops of useful plants which are resistant, or have been made resistant by recombinant means, to the phytotoxic effects of the herbicides.

Preference is given to the use of the inventive compounds or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the inventive compounds can be used as herbicides in crops of useful plants which are resistant, or have been made resistant by recombinant means, to the phytotoxic effects of the herbicides.

Conventional ways of producing novel plants which have modified properties in comparison to existing plants consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

- recombinant modifications of crop plants for the purpose of modifying the starch synthesized in the plants (e.g. WO 92/11376, WO 92/14827, WO 91/19806),
- transgenic crop plants which are resistant to particular herbicides of the glufosinate type (cf., for example, EP-A-0242236, EP-A-242246) or glyphosate type (WO 92/00377) or the sulfonylureas (EP-A-0257993, US-A-5013659),
- transgenic crop plants, for example cotton, with the ability to produce *Bacillus thuringiensis* toxins (Bt toxins) which make the plants resistant to particular pests (EP-A-0142924, EP-A-0193259),
- transgenic crop plants with a modified fatty acid composition (WO 91/13972),
- genetically modified crop plants with novel constituents or secondary metabolites, for example novel phytoalexins, which cause an increased disease resistance (EPA 309862, EPA0464461),
- genetically modified plants with reduced photorespiration, which have higher yields and higher stress tolerance (EPA 0305398),
- transgenic crop plants which produce pharmaceutically or diagnostically important proteins ("molecular pharming"),
- transgenic crop plants which are notable for higher yields or better quality,
- transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.), Gene Transfer to Plants, Springer Lab Manual (1995), Springer Verlag Berlin, Heidelberg or Christou, "Trends in Plant Science" 1 (1996) 423-431).

For such recombinant manipulations, nucleic acid molecules which allow mutagenesis or a sequence change by recombination of DNA sequences can be introduced into plasmids. With the aid of standard methods, it it possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim, 2nd edition, 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product. For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, in order to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

Thus, it is possible to obtain transgenic plants whose properties are altered by overexpression, suppression or inhibition of homologous (=natural) genes or gene sequences, or expression of heterologous (=foreign) genes or gene sequences.

Preferably, the inventive compounds can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the inventive active ingredients in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds as herbicides for control of harmful plants in transgenic crop plants.

The inventive compounds can be applied in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], volume 7, C. Hanser Verlag Munich, 4th edition 1986, Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To produce the wettable powders, the herbicidal active ingredients are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granulated inert material or by applying active ingredient concentrates by means of adhesives, for example polyvinyl alcohol, sodium polyacrylate or mineral oils, to the surface of carrier substances, such as sand, kaolinites or granulated inert material. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active ingredient concentration is, for example, about 10 to 90% by weight; the remainder to 100% by weight consists of the customary formulation constituents. In emulsifiable concentrates, the active ingredient concentration may be about 1 to 90% and preferably 5 to 80% by weight.

Formulations in the form of dusts comprise 1 to 30% by weight of active ingredient, preferably usually 5 to 20% by weight of active ingredient; sprayable solutions contain about 0.05 to 80% and preferably 2 to 50% by weight of active ingredient. In the case of water-dispersible granules, the active ingredient content depends partly on whether the active compound is present in liquid or solid form and on which granulation assistants, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2009 and literature cited therein. Examples of known herbicides or plant growth regulators which can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. In this list, one or else, in some cases, more than one application form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4 (1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

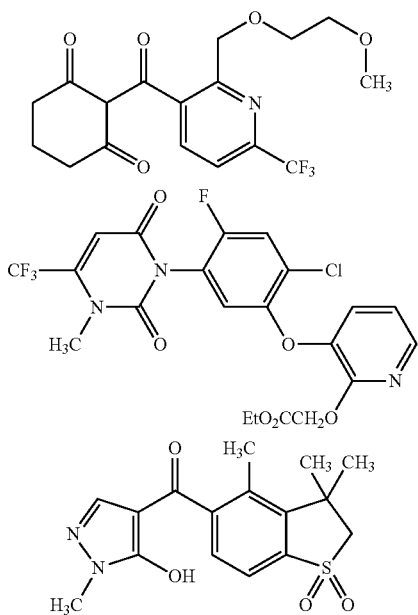

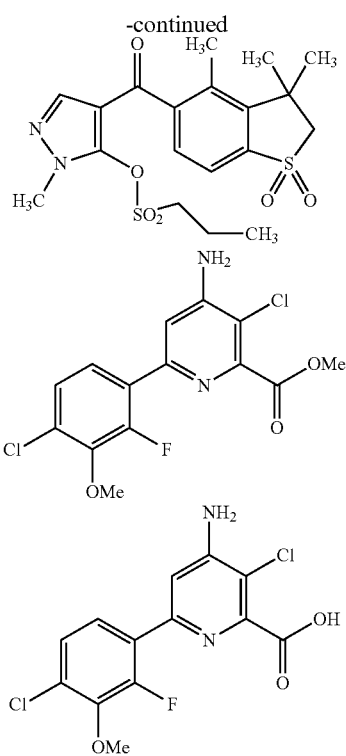

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more active substance, but it is preferably between 0.005 and 750 g/ha.

The examples which follow illustrate the invention.

A. CHEMICAL EXAMPLES

1. Synthesis of 4-chloro-3-methoxy-N-(4-methyl-1,2,5-oxadiazol-3-yl)-2,3-dihydro-1-benzothiophene-5-carboxamide 1,1-dioxide (table example No. 1928)

1.00 g (3.14 mmol) of 4-chloro-3-methoxy-2,3-dihydro-1-benzothiophene-5-carboxylic acid 1,1-dioxide and 0.33 g (3.15 mmol) of 4-methyl-1,2,5-oxadiazol-3-yl-amine were dissolved at room temperature (RT) in 35 ml of $CH_2Cl_2$, 3.02 g (4.74 mmol) of 2,4,6-tripropyl-1,3,5,2,4,6-trioxatriphosphinane 2,4,6-trioxide (50% solution in THF) were added and the mixture was stirred at RT for 1 h. Subsequently, 2.18 ml (15.64 mmol) of triethylamine and 75 mg (0.61 mmol) of 4-dimethylaminopyridine (DMAP) were added and the whole mixture was stirred at RT for 16 h. This was followed by washing with water and twice with 6N hydrochloric acid, drying of the organic phase over $Na_2SO_4$ and filtration with suction through silica gel, washing through with 1:2 heptane/ethyl acetate and concentration. Yield 708 mg (63%).

$^1$H NMR (CDCl$_3$): δ=2.44 (s,3H), 3.53 (s,3H), 3.57 (dd, 1H), 3.71 (d,1H), 5.15 (d,1H), 7.55 (d,1H), 7.74 (d,1H), 9.40 (s,1H)

2. Synthesis of 4-chloro-N-(1-methyl-1H-1,2,4-triazol-5-yl)-2,3-dihydro-1-benzothiophen-5-carboxamide 1,1-dioxide (table example No. 1545)

0.80 g (3.24 mmol) of 4-chloro-2,3-dihydro-1-benzothiophene-5-carboxylic acid 1,1-dioxide, 0.72 g (2.43 mmol) of di(1-methyl-1H-1,2,4-triazol-5-amine) sulfate and 20 mg (0.164 mmol) of DMAP were initially charged in 5 ml of pyridine, 0.65 g (5.35 mmol) of thionyl chloride were added and the mixture was stirred at 70° C. for 1 h. Subsequently, 0.5 ml of water was added, and the mixture was stirred for a further 30 min, acidified with saturated $KHSO_4$ solution and extracted three times with 100 ml each time of ethyl acetate. The combined organic phases were washed with saturated $NaHCO_3$ solution, dried over $Na_2SO_4$ and concentrated. The residue was purified by column chromatography (silica gel, heptane/ethyl acetate). Yield 642 mg (61%).
$^1$H NMR (DMSO-$d_6$): δ=3.40 (t,2H), 3.74 (t,2H), 3.79 (s,3H), 7.89 (br,3H), 11.39 (s,1H)

3. Synthesis of N-(1-ethyl-1H-tetrazol-5-yl)-4,4,5,8-tetramethyl-3,4-dihydro-2H-thiochromene-6-carboxamide 1,1-dioxide (table example No. 189)

1.00 g (3.54 mmol) of 4,4,5,8-tetramethyl-3,4-dihydro-2H-thiochromene-6-carboxylic acid 1,1-dioxide, 0.63 g (5.32 mmol) of 1-ethyl-5-aminotetrazole and 23 mg (0.188 mmol) of DMAP were initially charged in 7 ml of pyridine, 0.71 g (5.86 mmol) of thionyl chloride were added and the mixture was stirred at 70° C. for 1 h.

Subsequently, 0.5 ml of water was added, and the mixture was stirred for a further 30 min, acidified with saturated $KHSO_4$ solution and extracted three times with 100 ml each time of ethyl acetate. The combined organic phases were washed with saturated $NaHCO_3$ solution, dried over $Na_2SO_4$ and concentrated. The residue was purified by column chromatography (silica gel, heptane/ethyl acetate). Yield 492 mg (37%).
$^1$H NMR (CDCl$_3$): δ=1.56 (s,6H), 1.64 (t,3H), 2.36 (dd, 2H), 2.65 (s,3H), 2.77 (s,3H), 3.43 (dd,2H), 4.46 (q,2H), 7.37 (s,3H), 10.16 (s,1H)

The examples listed in the tables below were prepared analogously to the abovementioned methods or are obtainable analogously to the abovementioned methods. The compounds listed in the tables below are very particularly preferred.

The abbreviations used mean:

| | | | |
|---|---|---|---|
| Et = ethyl | Me = methyl | n-Pr = n-propyl | i-Pr = isopropyl |
| c-Pr = cyclopropyl | Ph = phenyl | | |

TABLE 1

Inventive compounds of the general formula (I) in which Q is Q1, Y is S(O)$_m$, R$^5$ is hydrogen and n is 2

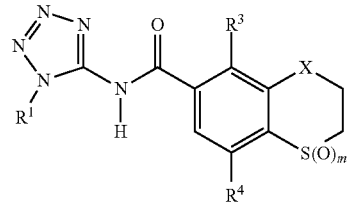

| No. | R$^1$ | R$^3$ | R$^4$ | m | X | 1H NMR |
|---|---|---|---|---|---|---|
| 1. | Me | Me | Me | 0 | CH$_2$ | |
| 2. | Me | Me | Me | 1 | CH$_2$ | |
| 3. | Me | Me | Me | 2 | CH$_2$ | |
| 4. | Me | Me | Me | 0 | CHMe | |
| 5. | Me | Me | Me | 1 | CHMe | |
| 6. | Me | Me | Me | 2 | CHMe | |
| 7. | Me | Me | Me | 0 | C(CH$_3$)$_2$ | CDCl3, 400 MHz: 1.49 (s, 6H), 2.04 (dd, 2H), 2.28 (s, 3H), 2.62 (s, 3H), 2.98 (dd, 2H), 4.10 (s, 3H), 7.22 (s, 1H), 8.81 (s, 1H) |
| 8. | Me | Me | Me | 1 | C(CH$_3$)$_2$ | |
| 9. | Me | Me | Me | 2 | C(CH$_3$)$_2$ | CDCl3, 400 MHz: 1.55 (s, 6H), 2.38 (dd, 2H), 2.64 (s, 3H), 2.81 (s, 3H), 3.43 (dd, 2H), 4.10 (s, 3H), 7.33 (s, 1H), 8.87 (s, 1H) |
| 10. | Me | Me | Me | 0 | C(OC$_2$H$_4$O) | |
| 11. | Me | Me | Me | 1 | C(OC$_2$H$_4$O) | |
| 12. | Me | Me | Me | 2 | C(OC$_2$H$_4$O) | |
| 13. | Me | Me | Me | 0 | C(SC$_2$H$_4$S) | |
| 14. | Me | Me | Me | 1 | C(SC$_2$H$_4$S) | |
| 15. | Me | Me | Me | 2 | C(SC$_2$H$_4$S) | |
| 16. | Me | Me | Me | 0 | CHOMe | |
| 17. | Me | Me | Me | 1 | CHOMe | |
| 18. | Me | Me | Me | 2 | CHOMe | |
| 19. | Me | Me | Me | 0 | CHOEt | |
| 20. | Me | Me | Me | 1 | CHOEt | |
| 21. | Me | Me | Me | 2 | CHOEt | |
| 22. | Me | Me | Me | 0 | CHOiPr | |
| 23. | Me | Me | Me | 1 | CHOiPr | |
| 24. | Me | Me | Me | 2 | CHOiPr | |
| 25. | Me | Me | Me | 0 | CHOCH$_2$cPr | |
| 26. | Me | Me | Me | 1 | CHOCH$_2$cPr | |
| 27. | Me | Me | Me | 2 | CHOCH$_2$cPr | |
| 28. | Me | Me | Me | 0 | CHOC$_2$H$_4$OMe | |
| 29. | Me | Me | Me | 1 | CHOC$_2$H$_4$OMe | |
| 30. | Me | Me | Me | 2 | CHOC$_2$H$_4$OMe | |
| 31. | Me | Me | Me | 0 | CHOCH$_2$CCH | |
| 32. | Me | Me | Me | 1 | CHOCH$_2$CCH | |
| 33. | Me | Me | Me | 2 | CHOCH$_2$CCH | |
| 34. | Me | Me | Me | 0 | CHOCH$_2$CH=CH$_2$ | |
| 35. | Me | Me | Me | 1 | CHOCH$_2$CH=CH$_2$ | |
| 36. | Me | Me | Me | 2 | CHOCH$_2$CH=CH$_2$ | |
| 37. | Me | Me | Me | 0 | OMe 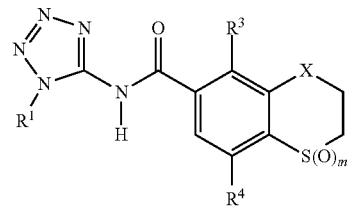 CH | |

TABLE 1-continued

Inventive compounds of the general formula (I) in which Q is Q1, Y is S(O)$_m$, R$^5$ is hydrogen and n is 2

| No. | R$^1$ | R$^3$ | R$^4$ | m | X | 1H NMR |
|---|---|---|---|---|---|---|
| 38. | Me | Me | Me | 1 | 2,6-dimethoxypyrimidin-4-yloxymethyl | |
| 39. | Me | Me | Me | 2 | 2,6-dimethoxypyrimidin-4-yloxymethyl | |
| 40. | Me | Me | Me | 0 | pyrazin-2-yloxymethyl | CDCl3, 400 MHz: 8.28-8.25 (m, 2H), 8.19 (m, 1H), 7.62 (s, 1H), 6.52 (m, 1H), 4.13 (s, 3H), 3.81 (m, 1H), 3.30 (m, 1H), 2.92-2.74 (m, 2H), 2.80 (s, 3H), 2.32 (s, 3H) |
| 41. | Me | Me | Me | 1 | pyrazin-2-yloxymethyl | |
| 42. | Me | Me | Me | 2 | pyrazin-2-yloxymethyl | |
| 43. | Me | Me | Me | 0 | pyrazol-1-ylmethyl | |
| 44. | Me | Me | Me | 1 | pyrazol-1-ylmethyl | |
| 45. | Me | Me | Me | 2 | pyrazol-1-ylmethyl | |
| 46. | Me | Me | Me | 0 | 1,2,3-triazol-1-ylmethyl | |
| 47. | Me | Me | Me | 1 | 1,2,3-triazol-1-ylmethyl | |
| 48. | Me | Me | Me | 2 | 1,2,3-triazol-1-ylmethyl | |
| 49. | Me | Me | Me | 0 | 1,2,3-triazol-2-ylmethyl | |
| 50. | Me | Me | Me | 1 | 1,2,3-triazol-2-ylmethyl | |
| 51. | Me | Me | Me | 2 | 1,2,3-triazol-2-ylmethyl | |
| 52. | Me | Me | Me | 0 | CHOC$_2$H$_4$F | |
| 53. | Me | Me | Me | 1 | CHOC$_2$H$_4$F | |
| 54. | Me | Me | Me | 2 | CHOC$_2$H$_4$F | |
| 55. | Me | Me | Me | 0 | C=NOMe | |
| 56. | Me | Me | Me | 1 | C=NOMe | |
| 57. | Me | Me | Me | 2 | C=NOMe | |
| 58. | Me | Me | Me | 0 | C=NOCH$_2$CCH | |
| 59. | Me | Me | Me | 1 | C=NOCH$_2$CCH | |
| 60. | Me | Me | Me | 2 | C=NOCH$_2$CCH | |
| 61. | Me | Me | Me | 0 | C=NOCH$_2$CH=CH$_2$ | |
| 62. | Me | Me | Me | 1 | C=NOCH$_2$CH=CH$_2$ | |
| 63. | Me | Me | Me | 2 | C=NOCH$_2$CH=CH$_2$ | |
| 64. | Me | Me | Me | 0 | C=O | |
| 65. | Me | Me | Me | 1 | C=O | |
| 66. | Me | Me | Me | 2 | C=O | |

TABLE 1-continued

Inventive compounds of the general formula (I) in which Q is Q1, Y is S(O)$_m$, R$^5$ is hydrogen and n is 2

| No. | R$^1$ | R$^3$ | R$^4$ | m | X | 1H NMR |
|---|---|---|---|---|---|---|
| 67. | Me | Me | Me | 0 | C=S | |
| 68. | Me | Me | Me | 1 | C=S | |
| 69. | Me | Me | Me | 2 | C=S | |
| 70. | Me | Me | Me | 0 | C=S | |
| 71. | Me | Me | Me | 1 | C=S | |
| 72. | Me | Me | Me | 2 | C=S | |
| 73. | Me | Me | Me | 0 | C=N—N(CH$_3$)$_2$ | |
| 74. | Me | Me | Me | 1 | C=N—N(CH$_3$)$_2$ | |
| 75. | Me | Me | Me | 2 | C=N—N(CH$_3$)$_2$ | |
| 76. | Me | Me | Me | 0 | O | |
| 77. | Me | Me | Me | 1 | O | |
| 78. | Me | Me | Me | 2 | O | |
| 79. | Me | Me | Me | 0 | S | |
| 80. | Me | Me | Me | 1 | S | |
| 81. | Me | Me | Me | 2 | S | |
| 82. | Me | Me | Me | 0 | SO | |
| 83. | Me | Me | Me | 1 | SO | |
| 84. | Me | Me | Me | 2 | SO | |
| 85. | Me | Me | Me | 0 | SO$_2$ | |
| 86. | Me | Me | Me | 1 | SO$_2$ | |
| 87. | Me | Me | Me | 2 | SO$_2$ | |
| 88. | Me | Me | Me | 0 | NMe | |
| 89. | Me | Me | Me | 1 | NMe | |
| 90. | Me | Me | Me | 2 | NMe | |
| 91. | Me | Me | H | 0 | CH$_2$ | |
| 92. | Me | Me | H | 1 | CH$_2$ | |
| 93. | Me | Me | H | 2 | CH$_2$ | |
| 94. | Me | Me | H | 0 | CHMe | |
| 95. | Me | Me | H | 1 | CHMe | |
| 96. | Me | Me | H | 2 | CHMe | |
| 97. | Me | Me | H | 0 | C(CH$_3$)$_2$ | |
| 98. | Me | Me | H | 1 | C(CH$_3$)$_2$ | |
| 99. | Me | Me | H | 2 | C(CH$_3$)$_2$ | |
| 100. | Me | Me | H | 0 | C(OC$_2$H$_4$O) | |
| 101. | Me | Me | H | 1 | C(OC$_2$H$_4$O) | |
| 102. | Me | Me | H | 2 | C(OC$_2$H$_4$O) | |
| 103. | Me | Me | H | 0 | C(SC$_2$H$_4$S) | |
| 104. | Me | Me | H | 1 | C(SC$_2$H$_4$S) | |
| 105. | Me | Me | H | 2 | C(SC$_2$H$_4$S) | |
| 106. | Me | Me | H | 0 | CHOMe | |
| 107. | Me | Me | H | 1 | CHOMe | |
| 108. | Me | Me | H | 2 | CHOMe | |
| 109. | Me | Me | H | 0 | CHOEt | |
| 110. | Me | Me | H | 1 | CHOEt | |
| 111. | Me | Me | H | 2 | CHOEt | |
| 112. | Me | Me | H | 0 | CHOiPr | |
| 113. | Me | Me | H | 1 | CHOiPr | |
| 114. | Me | Me | H | 2 | CHOiPr | |
| 115. | Me | Me | H | 0 | CHOCH$_2$cPr | |
| 116. | Me | Me | H | 1 | CHOCH$_2$cPr | |
| 117. | Me | Me | H | 2 | CHOCH$_2$cPr | |
| 118. | Me | Me | H | 0 | CHOC$_2$H$_4$OMe | |
| 119. | Me | Me | H | 1 | CHOC$_2$H$_4$OMe | |
| 120. | Me | Me | H | 2 | CHOC$_2$H$_4$OMe | |
| 121. | Me | Me | H | 0 | CHOCH$_2$CCH | |
| 122. | Me | Me | H | 1 | CHOCH$_2$CCH | |
| 123. | Me | Me | H | 2 | CHOCH$_2$CCH | |
| 124. | Me | Me | H | 0 | CHOCH$_2$CH=CH$_2$ | |
| 125. | Me | Me | H | 1 | CHOCH$_2$CH=CH$_2$ | |
| 126. | Me | Me | H | 2 | CHOCH$_2$CH=CH$_2$ | |
| 127. | Me | Me | H | 0 | 2,6-dimethoxypyrimidin-4-yloxymethyl | |
| 128. | Me | Me | H | 1 | 2,6-dimethoxypyrimidin-4-yloxymethyl | |
| 129. | Me | Me | H | 2 | 2,6-dimethoxypyrimidin-4-yloxymethyl | |
| 130. | Me | Me | H | 0 | pyrazin-2-yloxymethyl | |
| 131. | Me | Me | H | 1 | pyrazin-2-yloxymethyl | |
| 132. | Me | Me | H | 2 | pyrazin-2-yloxymethyl | |
| 133. | Me | Me | H | 0 | pyrazol-1-ylmethyl | |

TABLE 1-continued

Inventive compounds of the general formula (I) in which Q is Q1, Y is S(O)$_m$, R$^5$ is hydrogen and n is 2

| No. | R$^1$ | R$^3$ | R$^4$ | m | X | 1H NMR |
|---|---|---|---|---|---|---|
| 134. | Me | Me | H | 1 | N-pyrazolyl-CH | |
| 135. | Me | Me | H | 2 | N-pyrazolyl-CH | |
| 136. | Me | Me | H | 0 | N-triazolyl-CH | |
| 137. | Me | Me | H | 1 | N-triazolyl-CH | |
| 138. | Me | Me | H | 2 | N-triazolyl-CH | |
| 139. | Me | Me | H | 0 | N-triazolyl-CH | |
| 140. | Me | Me | H | 1 | N-triazolyl-CH | |
| 141. | Me | Me | H | 2 | N-triazolyl-CH | |
| 142. | Me | Me | H | 0 | CHOC$_2$H$_4$F | |
| 143. | Me | Me | H | 1 | CHOC$_2$H$_4$F | |
| 144. | Me | Me | H | 2 | CHOC$_2$H$_4$F | |
| 145. | Me | Me | H | 0 | C=NOMe | |
| 146. | Me | Me | H | 1 | C=NOMe | |
| 147. | Me | Me | H | 2 | C=NOMe | |
| 148. | Me | Me | H | 0 | C=NOCH$_2$CCH | |
| 149. | Me | Me | H | 1 | C=NOCH$_2$CCH | |
| 150. | Me | Me | H | 2 | C=NOCH$_2$CCH | |
| 151. | Me | Me | H | 0 | C=NOCH$_2$CH=CH$_2$ | |
| 152. | Me | Me | H | 1 | C=NOCH$_2$CH=CH$_2$ | |
| 153. | Me | Me | H | 2 | C=NOCH$_2$CH=CH$_2$ | |
| 154. | Me | Me | H | 0 | C=O | |
| 155. | Me | Me | H | 1 | C=O | |
| 156. | Me | Me | H | 2 | C=O | |
| 157. | Me | Me | H | 0 | C=S | |
| 158. | Me | Me | H | 1 | C=S | |
| 159. | Me | Me | H | 2 | C=S | |
| 160. | Me | Me | H | 0 | C=S | |
| 161. | Me | Me | H | 1 | C=S | |
| 162. | Me | Me | H | 2 | C=S | |
| 163. | Me | Me | H | 0 | C=N—N(CH$_3$)$_2$ | |
| 164. | Me | Me | H | 1 | C=N—N(CH$_3$)$_2$ | |
| 165. | Me | Me | H | 2 | C=N—N(CH$_3$)$_2$ | |
| 166. | Me | Me | H | 0 | O | |
| 167. | Me | Me | H | 1 | O | |
| 168. | Me | Me | H | 2 | O | |
| 169. | Me | Me | H | 0 | S | |
| 170. | Me | Me | H | 1 | S | |
| 171. | Me | Me | H | 2 | S | |
| 172. | Me | Me | H | 0 | SO | |
| 173. | Me | Me | H | 1 | SO | |
| 174. | Me | Me | H | 2 | SO | |
| 175. | Me | Me | H | 0 | SO$_2$ | |
| 176. | Me | Me | H | 1 | SO$_2$ | |
| 177. | Me | Me | H | 2 | SO$_2$ | |
| 178. | Me | Me | H | 0 | NMe | |
| 179. | Me | Me | H | 1 | NMe | |
| 180. | Me | Me | H | 2 | NMe | |
| 181. | Et | Me | Me | 0 | CH$_2$ | |
| 182. | Et | Me | Me | 1 | CH$_2$ | |
| 183. | Et | Me | Me | 2 | CH$_2$ | |
| 184. | Et | Me | Me | 0 | CHMe | |
| 185. | Et | Me | Me | 1 | CHMe | |
| 186. | Et | Me | Me | 2 | CHMe | |
| 187. | Et | Me | Me | 0 | C(CH$_3$)$_2$ | CDCl3, 400 MHz: 1.49 (s, 6H), 1.61 (t, 3H), 2.04 (dd, 2H), 2.29 (s, 3H), 2.62 (s, 3H), 2.99 (dd, 2H), 4.46 (q, 2H), 7.23 (s, 1H), 9.12 (s, 1H) |
| 188. | Et | Me | Me | 1 | C(CH$_3$)$_2$ | |
| 189. | Et | Me | Me | 2 | C(CH$_3$)$_2$ | CDCl3, 400 MHz: 1.56 (s, 6H), 1.64 (t, 3H), 2.36 (dd, 2H), 2.65 (s, 3H), 2.77 (s, 3H), 3.43 (dd, 2H), 4.46 (q, 2H), 7.37 (s, 1H), 10.16 (s, 1H) |
| 190. | Et | Me | Me | 0 | C(OC$_2$H$_4$O) | |
| 191. | Et | Me | Me | 1 | C(OC$_2$H$_4$O) | |
| 192. | Et | Me | Me | 2 | C(OC$_2$H$_4$O) | |
| 193. | Et | Me | Me | 0 | C(SC$_2$H$_4$S) | |
| 194. | Et | Me | Me | 1 | C(SC$_2$H$_4$S) | |
| 195. | Et | Me | Me | 2 | C(SC$_2$H$_4$S) | |
| 196. | Et | Me | Me | 0 | CHOMe | |
| 197. | Et | Me | Me | 1 | CHOMe | |
| 198. | Et | Me | Me | 2 | CHOMe | |
| 199. | Et | Me | Me | 0 | CHOEt | |
| 200. | Et | Me | Me | 1 | CHOEt | |

TABLE 1-continued

Inventive compounds of the general formula (I) in which Q is Q1, Y is S(O)$_m$, R$^5$ is hydrogen and n is 2

| No. | R$^1$ | R$^3$ | R$^4$ | m | X | 1H NMR |
|---|---|---|---|---|---|---|
| 201. | Et | Me | Me | 2 | CHOEt | |
| 202. | Et | Me | Me | 0 | CHOiPr | |
| 203. | Et | Me | Me | 1 | CHOiPr | |
| 204. | Et | Me | Me | 2 | CHOiPr | |
| 205. | Et | Me | Me | 0 | CHOCH$_2$cPr | |
| 206. | Et | Me | Me | 1 | CHOCH$_2$cPr | |
| 207. | Et | Me | Me | 2 | CHOCH$_2$cPr | |
| 208. | Et | Me | Me | 0 | CHOC$_2$H$_4$OMe | |
| 209. | Et | Me | Me | 1 | CHOC$_2$H$_4$OMe | |
| 210. | Et | Me | Me | 2 | CHOC$_2$H$_4$OMe | |
| 211. | Et | Me | Me | 0 | CHOCH$_2$CCH | |
| 212. | Et | Me | Me | 1 | CHOCH$_2$CCH | |
| 213. | Et | Me | Me | 2 | CHOCH$_2$CCH | |
| 214. | Et | Me | Me | 0 | CHOCH$_2$CH=CH$_2$ | |
| 215. | Et | Me | Me | 1 | CHOCH$_2$CH=CH$_2$ | |
| 216. | Et | Me | Me | 2 | CHOCH$_2$CH=CH$_2$ | |
| 217. | Et | Me | Me | 0 | 2,6-dimethoxypyrimidin-2-yloxy-CH | |
| 218. | Et | Me | Me | 1 | 2,6-dimethoxypyrimidin-2-yloxy-CH | |
| 219. | Et | Me | Me | 2 | 2,6-dimethoxypyrimidin-2-yloxy-CH | |
| 220. | Et | Me | Me | 0 | pyrazin-2-yloxy-CH | |
| 221. | Et | Me | Me | 1 | pyrazin-2-yloxy-CH | |
| 222. | Et | Me | Me | 2 | pyrazin-2-yloxy-CH | |
| 223. | Et | Me | Me | 0 | pyrazol-1-yl-CH | |
| 224. | Et | Me | Me | 1 | pyrazol-1-yl-CH | |
| 225. | Et | Me | Me | 2 | pyrazol-1-yl-CH | |
| 226. | Et | Me | Me | 0 | 1,2,3-triazol-1-yl-CH | |
| 227. | Et | Me | Me | 1 | 1,2,3-triazol-1-yl-CH | |
| 228. | Et | Me | Me | 2 | 1,2,3-triazol-1-yl-CH | |
| 229. | Et | Me | Me | 0 | 1,2,3-triazol-2-yl-CH | |
| 230. | Et | Me | Me | 1 | 1,2,3-triazol-2-yl-CH | |

TABLE 1-continued

Inventive compounds of the general formula (I) in which Q is Q1, Y is S(O)$_m$, R$^5$ is hydrogen and n is 2

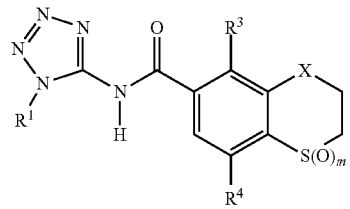

| No. | R$^1$ | R$^3$ | R$^4$ | m | X | 1H NMR |
|---|---|---|---|---|---|---|
| 231. | Et | Me | Me | 2 | 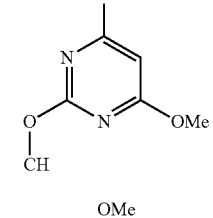 | |
| 232. | Et | Me | Me | 0 | CHOC$_2$H$_4$F | |
| 233. | Et | Me | Me | 1 | CHOC$_2$H$_4$F | |
| 234. | Et | Me | Me | 2 | CHOC$_2$H$_4$F | |
| 235. | Et | Me | Me | 0 | C=NOMe | |
| 236. | Et | Me | Me | 1 | C=NOMe | |
| 237. | Et | Me | Me | 2 | C=NOMe | |
| 238. | Et | Me | Me | 0 | C=NOCH$_2$CCH | |
| 239. | Et | Me | Me | 1 | C=NOCH$_2$CCH | |
| 240. | Et | Me | Me | 2 | C=NOCH$_2$CCH | |
| 241. | Et | Me | Me | 0 | C=NOCH$_2$CH=CH$_2$ | |
| 242. | Et | Me | Me | 1 | C=NOCH$_2$CH=CH$_2$ | |
| 243. | Et | Me | Me | 2 | C=NOCH$_2$CH=CH$_2$ | |
| 244. | Et | Me | Me | 0 | C=O | |
| 245. | Et | Me | Me | 1 | C=O | |
| 246. | Et | Me | Me | 2 | C=O | |
| 247. | Et | Me | Me | 0 | C=S | |
| 248. | Et | Me | Me | 1 | C=S | |
| 249. | Et | Me | Me | 2 | C=S | |
| 250. | Et | Me | Me | 0 | C=S | |
| 251. | Et | Me | Me | 1 | C=S | |
| 252. | Et | Me | Me | 2 | C=S | |
| 253. | Et | Me | Me | 0 | C=N—N(CH$_3$)$_2$ | |
| 254. | Et | Me | Me | 1 | C=N—N(CH$_3$)$_2$ | |
| 255. | Et | Me | Me | 2 | C=N—N(CH$_3$)$_2$ | |
| 256. | Et | Me | Me | 0 | O | |
| 257. | Et | Me | Me | 1 | O | |
| 258. | Et | Me | Me | 2 | O | |
| 259. | Et | Me | Me | 0 | S | |
| 260. | Et | Me | Me | 1 | S | |
| 261. | Et | Me | Me | 2 | S | |
| 262. | Et | Me | Me | 0 | SO | |
| 263. | Et | Me | Me | 1 | SO | |
| 264. | Et | Me | Me | 2 | SO | |
| 265. | Et | Me | Me | 0 | SO$_2$ | |
| 266. | Et | Me | Me | 1 | SO$_2$ | |
| 267. | Et | Me | Me | 2 | SO$_2$ | |
| 268. | Et | Me | Me | 0 | NMe | |
| 269. | Et | Me | Me | 1 | NMe | |
| 270. | Et | Me | Me | 2 | NMe | |
| 271. | Et | Me | H | 0 | CH$_2$ | |
| 272. | Et | Me | H | 1 | CH$_2$ | |
| 273. | Et | Me | H | 2 | CH$_2$ | |
| 274. | Et | Me | H | 0 | CHMe | |
| 275. | Et | Me | H | 1 | CHMe | |
| 276. | Et | Me | H | 2 | CHMe | |
| 277. | Et | Me | H | 0 | C(CH$_3$)$_2$ | |
| 278. | Et | Me | H | 1 | C(CH$_3$)$_2$ | |
| 279. | Et | Me | H | 2 | C(CH$_3$)$_2$ | |
| 280. | Et | Me | H | 0 | C(OC$_2$H$_4$O) | |
| 281. | Et | Me | H | 1 | C(OC$_2$H$_4$O) | |
| 282. | Et | Me | H | 2 | C(OC$_2$H$_4$O) | |
| 283. | Et | Me | H | 0 | C(SC$_2$H$_4$S) | |
| 284. | Et | Me | H | 1 | C(SC$_2$H$_4$S) | |
| 285. | Et | Me | H | 2 | C(SC$_2$H$_4$S) | |
| 286. | Et | Me | H | 0 | CHOMe | |
| 287. | Et | Me | H | 1 | CHOMe | |
| 288. | Et | Me | H | 2 | CHOMe | |
| 289. | Et | Me | H | 0 | CHOEt | |
| 290. | Et | Me | H | 1 | CHOEt | |
| 291. | Et | Me | H | 2 | CHOEt | |
| 292. | Et | Me | H | 0 | CHOiPr | |
| 293. | Et | Me | H | 1 | CHOiPr | |
| 294. | Et | Me | H | 2 | CHOiPr | |
| 295. | Et | Me | H | 0 | CHOCH$_2$cPr | |
| 296. | Et | Me | H | 1 | CHOCH$_2$cPr | |
| 297. | Et | Me | H | 2 | CHOCH$_2$cPr | |
| 298. | Et | Me | H | 0 | CHOC$_2$H$_4$OMe | |
| 299. | Et | Me | H | 1 | CHOC$_2$H$_4$OMe | |
| 300. | Et | Me | H | 2 | CHOC$_2$H$_4$OMe | |
| 301. | Et | Me | H | 0 | CHOCH$_2$CCH | |
| 302. | Et | Me | H | 1 | CHOCH$_2$CCH | |
| 303. | Et | Me | H | 2 | CHOCH$_2$CCH | |
| 304. | Et | Me | H | 0 | CHOCH$_2$CH=CH$_2$ | |
| 305. | Et | Me | H | 1 | CHOCH$_2$CH=CH$_2$ | |
| 306. | Et | Me | H | 2 | CHOCH$_2$CH=CH$_2$ | |
| 307. | Et | Me | H | 0 | 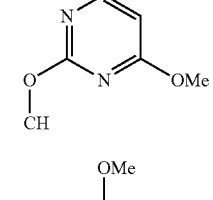 | |
| 308. | Et | Me | H | 1 | 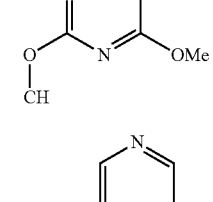 | |
| 309. | Et | Me | H | 2 | 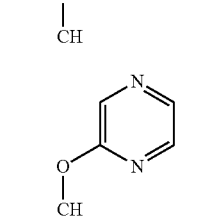 | |
| 310. | Et | Me | H | 0 |  | |
| 311. | Et | Me | H | 1 | | |

TABLE 1-continued

Inventive compounds of the general formula (I) in which Q is Q1, Y is S(O)$_m$, R$^5$ is hydrogen and n is 2

| No. | R$^1$ | R$^3$ | R$^4$ | m | X | 1H NMR |
|---|---|---|---|---|---|---|
| 312. | Et | Me | H | 2 | pyrazinyl-O-CH | |
| 313. | Et | Me | H | 0 | pyrazol-1-yl-CH | |
| 314. | Et | Me | H | 1 | pyrazol-1-yl-CH | |
| 315. | Et | Me | H | 2 | pyrazol-1-yl-CH | |
| 316. | Et | Me | H | 0 | 1,2,3-triazol-1-yl-CH | |
| 317. | Et | Me | H | 1 | 1,2,3-triazol-1-yl-CH | |
| 318. | Et | Me | H | 2 | 1,2,3-triazol-1-yl-CH | |
| 319. | Et | Me | H | 0 | 1,2,3-triazol-2-yl-CH | |
| 320. | Et | Me | H | 1 | 1,2,3-triazol-2-yl-CH | |
| 321 | Et | Me | H | 2 | 1,2,3-triazol-2-yl-CH | |
| 322. | Et | Me | H | 0 | CHOC$_2$H$_4$F | |
| 323. | Et | Me | H | 1 | CHOC$_2$H$_4$F | |
| 324. | Et | Me | H | 2 | CHOC$_2$H$_4$F | |
| 325. | Et | Me | H | 0 | C=NOMe | |
| 326. | Et | Me | H | 1 | C=NOMe | |
| 327. | Et | Me | H | 2 | C=NOMe | |
| 328. | Et | Me | H | 0 | C=NOCH$_2$CCH | |
| 329. | Et | Me | H | 1 | C=NOCH$_2$CCH | |
| 330. | Et | Me | H | 2 | C=NOCH$_2$CCH | |
| 331. | Et | Me | H | 0 | C=NOCH$_2$CH=CH$_2$ | |
| 332. | Et | Me | H | 1 | C=NOCH$_2$CH=CH$_2$ | |
| 333. | Et | Me | H | 2 | C=NOCH$_2$CH=CH$_2$ | |
| 334. | Et | Me | H | 0 | C=O | |
| 335. | Et | Me | H | 1 | C=O | |
| 336. | Et | Me | H | 2 | C=O | |
| 337. | Et | Me | H | 0 | C=S | |
| 338. | Et | Me | H | 1 | C=S | |
| 339. | Et | Me | H | 2 | C=S | |
| 340. | Et | Me | H | 0 | C=S | |
| 341. | Et | Me | H | 1 | C=S | |
| 342. | Et | Me | H | 2 | C=S | |
| 343. | Et | Me | H | 0 | C=N—N(CH$_3$)$_2$ | |
| 344. | Et | Me | H | 1 | C=N—N(CH$_3$)$_2$ | |
| 345. | Et | Me | H | 2 | C=N—N(CH$_3$)$_2$ | |
| 346. | Et | Me | H | 0 | O | |
| 347. | Et | Me | H | 1 | O | |
| 348. | Et | Me | H | 2 | O | |
| 349. | Et | Me | H | 0 | S | |
| 350. | Et | Me | H | 1 | S | |
| 351. | Et | Me | H | 2 | S | |
| 352. | Et | Me | H | 0 | SO | |
| 353. | Et | Me | H | 1 | SO | |
| 354. | Et | Me | H | 2 | SO | |
| 355. | Et | Me | H | 0 | SO$_2$ | |
| 356. | Et | Me | H | 1 | SO$_2$ | |
| 357. | Et | Me | H | 2 | SO$_2$ | |
| 358. | Et | Me | H | 0 | NMe | |
| 359. | Et | Me | H | 1 | NMe | |
| 360. | Et | Me | H | 2 | NMe | |

TABLE 2

Inventive compounds of the general formula (I) in which Q is Q2, Y is S(O)$_m$, R$^5$ is hydrogen and n is 2

| Number | R$^1$ | R$^3$ | R$^4$ | m | X | 1H NMR |
|---|---|---|---|---|---|---|
| 361. | Me | Me | Me | 0 | CH$_2$ | |
| 362. | Me | Me | Me | 1 | CH$_2$ | |
| 363. | Me | Me | Me | 2 | CH$_2$ | |
| 364. | Me | Me | Me | 0 | CHMe | |
| 365. | Me | Me | Me | 1 | CHMe | |
| 366. | Me | Me | Me | 2 | CHMe | |
| 367. | Me | Me | Me | 0 | C(CH$_3$)$_2$ | |
| 368. | Me | Me | Me | 1 | C(CH$_3$)$_2$ | |
| 369. | Me | Me | Me | 2 | C(CH$_3$)$_2$ | |
| 370. | Me | Me | Me | 0 | C(OC$_2$H$_4$O) | |
| 371. | Me | Me | Me | 1 | C(OC$_2$H$_4$O) | |
| 372. | Me | Me | Me | 2 | C(OC$_2$H$_4$O) | |
| 373. | Me | Me | Me | 0 | C(SC$_2$H$_4$S) | |
| 374. | Me | Me | Me | 1 | C(SC$_2$H$_4$S) | |
| 375. | Me | Me | Me | 2 | C(SC$_2$H$_4$S) | |
| 376. | Me | Me | Me | 0 | CHOMe | |
| 377. | Me | Me | Me | 1 | CHOMe | |
| 378. | Me | Me | Me | 2 | CHOMe | |
| 379. | Me | Me | Me | 0 | CHOEt | |
| 380. | Me | Me | Me | 1 | CHOEt | |
| 381. | Me | Me | Me | 2 | CHOEt | |
| 382. | Me | Me | Me | 0 | CHOiPr | |
| 383. | Me | Me | Me | 1 | CHOiPr | |
| 384. | Me | Me | Me | 2 | CHOiPr | |
| 385. | Me | Me | Me | 0 | CHOCH$_2$cPr | |
| 386. | Me | Me | Me | 1 | CHOCH$_2$cPr | |
| 387. | Me | Me | Me | 2 | CHOCH$_2$cPr | |
| 388. | Me | Me | Me | 0 | CHOC$_2$H$_4$OMe | |
| 389. | Me | Me | Me | 1 | CHOC$_2$H$_4$OMe | |
| 390. | Me | Me | Me | 2 | CHOC$_2$H$_4$OMe | |
| 391. | Me | Me | Me | 0 | CHOCH$_2$CCH | |
| 392. | Me | Me | Me | 1 | CHOCH$_2$CCH | |
| 393. | Me | Me | Me | 2 | CHOCH$_2$CCH | |
| 394. | Me | Me | Me | 0 | CHOCH$_2$CH=CH$_2$ | |
| 395. | Me | Me | Me | 1 | CHOCH$_2$CH=CH$_2$ | |
| 396. | Me | Me | Me | 2 | CHOCH$_2$CH=CH$_2$ | |
| 397. | Me | Me | Me | 0 | CH–O–(4,6-dimethoxypyrimidin-2-yl) | |
| 398. | Me | Me | Me | 1 | CH–O–(4,6-dimethoxypyrimidin-2-yl) | |
| 399. | Me | Me | Me | 2 | CH–O–(4,6-dimethoxypyrimidin-2-yl) | |
| 400. | Me | Me | Me | 0 | CH–O–(pyrazin-2-yl) | |
| 401. | Me | Me | Me | 1 | CH–O–(pyrazin-2-yl) | |
| 402. | Me | Me | Me | 2 | CH–O–(pyrazin-2-yl) | |
| 403. | Me | Me | Me | 0 | CH–(1H-pyrazol-1-yl) | |
| 404. | Me | Me | Me | 1 | CH–(1H-pyrazol-1-yl) | |
| 405. | Me | Me | Me | 2 | CH–(1H-pyrazol-1-yl) | |
| 406. | Me | Me | Me | 0 | CH–(1H-1,2,3-triazol-1-yl) | |

TABLE 2-continued

Inventive compounds of the general formula (I) in which Q is Q2, Y is S(O)$_m$, R$^5$ is hydrogen and n is 2

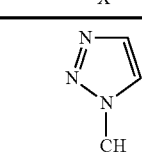

| Number | R$^1$ | R$^3$ | R$^4$ | m | X | 1H NMR |
|---|---|---|---|---|---|---|
| 407. | Me | Me | Me | 1 | 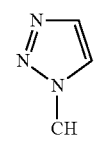 | |
| 408. | Me | Me | Me | 2 | 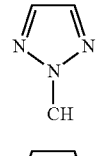 | |
| 409. | Me | Me | Me | 0 | 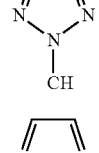 | |
| 410. | Me | Me | Me | 1 | 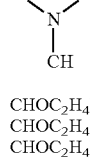 | |
| 411. | Me | Me | Me | 2 | 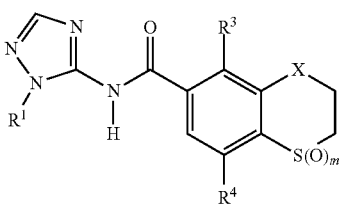 | |
| 412. | Me | Me | Me | 0 | CHOC$_2$H$_4$F | |
| 413. | Me | Me | Me | 1 | CHOC$_2$H$_4$F | |
| 414. | Me | Me | Me | 2 | CHOC$_2$H$_4$F | |
| 415. | Me | Me | Me | 0 | C=NOMe | |
| 416. | Me | Me | Me | 1 | C=NOMe | |
| 417. | Me | Me | Me | 2 | C=NOMe | |
| 418. | Me | Me | Me | 0 | C=NOCH$_2$CCH | |
| 419. | Me | Me | Me | 1 | C=NOCH$_2$CCH | |
| 420. | Me | Me | Me | 2 | C=NOCH$_2$CCH | |
| 421. | Me | Me | Me | 0 | C=NOCH$_2$CH=CH$_2$ | |
| 422. | Me | Me | Me | 1 | C=NOCH$_2$CH=CH$_2$ | |
| 423. | Me | Me | Me | 2 | C=NOCH$_2$CH=CH$_2$ | |
| 424. | Me | Me | Me | 0 | C=O | |
| 425. | Me | Me | Me | 1 | C=O | |
| 426. | Me | Me | Me | 2 | C=O | |
| 427. | Me | Me | Me | 0 | C=S | |
| 428. | Me | Me | Me | 1 | C=S | |
| 429. | Me | Me | Me | 2 | C=S | |
| 430. | Me | Me | Me | 0 | C=S | |
| 431. | Me | Me | Me | 1 | C=S | |
| 432. | Me | Me | Me | 2 | C=S | |
| 433. | Me | Me | Me | 0 | C=N—N(CH$_3$)$_2$ | |
| 434. | Me | Me | Me | 1 | C=N—N(CH$_3$)$_2$ | |
| 435. | Me | Me | Me | 2 | C=N—N(CH$_3$)$_2$ | |
| 436. | Me | Me | Me | 0 | O | |
| 437. | Me | Me | Me | 1 | O | |
| 438. | Me | Me | Me | 2 | O | |
| 439. | Me | Me | Me | 0 | S | |
| 440. | Me | Me | Me | 1 | S | |
| 441. | Me | Me | Me | 2 | S | |
| 442. | Me | Me | Me | 0 | SO | |
| 443. | Me | Me | Me | 1 | SO | |
| 444. | Me | Me | Me | 2 | SO | |
| 445. | Me | Me | Me | 0 | SO$_2$ | |
| 446. | Me | Me | Me | 1 | SO$_2$ | |
| 447. | Me | Me | Me | 2 | SO$_2$ | |
| 448. | Me | Me | Me | 0 | NMe | |
| 449. | Me | Me | Me | 1 | NMe | |
| 450. | Me | Me | Me | 2 | NMe | |
| 451. | Me | Me | H | 0 | CH$_2$ | |
| 452. | Me | Me | H | 1 | CH$_2$ | |
| 453. | Me | Me | H | 2 | CH$_2$ | |
| 454. | Me | Me | H | 0 | CHMe | |
| 455. | Me | Me | H | 1 | CHMe | |
| 456. | Me | Me | H | 2 | CHMe | |
| 457. | Me | Me | H | 0 | C(CH$_3$)$_2$ | |
| 458. | Me | Me | H | 1 | C(CH$_3$)$_2$ | |
| 459. | Me | Me | H | 2 | C(CH$_3$)$_2$ | |
| 460. | Me | Me | H | 0 | C(OC$_2$H$_4$O) | |
| 461. | Me | Me | H | 1 | C(OC$_2$H$_4$O) | |
| 462. | Me | Me | H | 2 | C(OC$_2$H$_4$O) | |
| 463. | Me | Me | H | 0 | C(SC$_2$H$_4$S) | |
| 464. | Me | Me | H | 1 | C(SC$_2$H$_4$S) | |
| 465. | Me | Me | H | 2 | C(SC$_2$H$_4$S) | |
| 466. | Me | Me | H | 0 | CHOMe | |
| 467. | Me | Me | H | 1 | CHOMe | |
| 468. | Me | Me | H | 2 | CHOMe | |
| 469. | Me | Me | H | 0 | CHOEt | |
| 470. | Me | Me | H | 1 | CHOEt | |
| 471. | Me | Me | H | 2 | CHOEt | |
| 472. | Me | Me | H | 0 | CHOiPr | |
| 473. | Me | Me | H | 1 | CHOiPr | |
| 474. | Me | Me | H | 2 | CHOiPr | |
| 475. | Me | Me | H | 0 | CHOCH$_2$cPr | |
| 476. | Me | Me | H | 1 | CHOCH$_2$cPr | |
| 477. | Me | Me | H | 2 | CHOCH$_2$cPr | |
| 478. | Me | Me | H | 0 | CHOC$_2$H$_4$OMe | |
| 479. | Me | Me | H | 1 | CHOC$_2$H$_4$OMe | |
| 480. | Me | Me | H | 2 | CHOC$_2$H$_4$OMe | |
| 481. | Me | Me | H | 0 | CHOCH$_2$CCH | |
| 482. | Me | Me | H | 1 | CHOCH$_2$CCH | |
| 483. | Me | Me | H | 2 | CHOCH$_2$CCH | |
| 484. | Me | Me | H | 0 | CHOCH$_2$CH=CH$_2$ | |
| 485. | Me | Me | H | 1 | CHOCH$_2$CH=CH$_2$ | |
| 486. | Me | Me | H | 2 | CHOCH$_2$CH=CH$_2$ | |
| 487. | Me | Me | H | 0 | 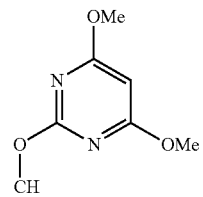 | |

TABLE 2-continued

Inventive compounds of the general formula (I) in which Q is Q2, Y is S(O)$_m$, R$^5$ is hydrogen and n is 2

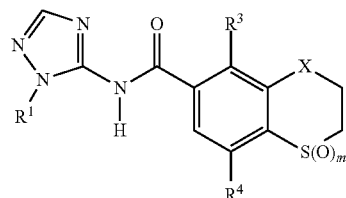

| Number | R$^1$ | R$^3$ | R$^4$ | m | X | 1H NMR |
|---|---|---|---|---|---|---|
| 488. | Me | Me | H | 1 | pyrimidine-OMe,OMe-O-CH | |
| 489. | Me | Me | H | 2 | pyrimidine-OMe,OMe-O-CH | |
| 490. | Me | Me | H | 0 | pyrazine-O-CH | |
| 491. | Me | Me | H | 1 | pyrazine-O-CH | |
| 492. | Me | Me | H | 2 | pyrazine-O-CH | |
| 493. | Me | Me | H | 0 | pyrazole-CH | |
| 494. | Me | Me | H | 1 | pyrazole-CH | |
| 495. | Me | Me | H | 2 | pyrazole-CH | |
| 496. | Me | Me | H | 0 | triazole-CH | |
| 497. | Me | Me | H | 1 | triazole-CH | |
| 498. | Me | Me | H | 2 | triazole-CH | |
| 499. | Me | Me | H | 0 | triazole-CH | |
| 500. | Me | Me | H | 1 | triazole-CH | |
| 501. | Me | Me | H | 2 | triazole-CH | |
| 502. | Me | Me | H | 0 | CHOC$_2$H$_4$F | |
| 503. | Me | Me | H | 1 | CHOC$_2$H$_4$F | |
| 504. | Me | Me | H | 2 | CHOC$_2$H$_4$F | |
| 505. | Me | Me | H | 0 | C=NOMe | |
| 506. | Me | Me | H | 1 | C=NOMe | |
| 507. | Me | Me | H | 2 | C=NOMe | |
| 508. | Me | Me | H | 0 | C=NOCH$_2$CCH | |
| 509. | Me | Me | H | 1 | C=NOCH$_2$CCH | |
| 510. | Me | Me | H | 2 | C=NOCH$_2$CCH | |
| 511. | Me | Me | H | 0 | C=NOCH$_2$CH=CH$_2$ | |
| 512. | Me | Me | H | 1 | C=NOCH$_2$CH=CH$_2$ | |
| 513. | Me | Me | H | 2 | C=NOCH$_2$CH=CH$_2$ | |
| 514. | Me | Me | H | 0 | C=O | |
| 515. | Me | Me | H | 1 | C=O | |
| 516. | Me | Me | H | 2 | C=O | |
| 517. | Me | Me | H | 0 | C=S | |
| 518. | Me | Me | H | 1 | C=S | |
| 519. | Me | Me | H | 2 | C=S | |
| 520. | Me | Me | H | 0 | C=S | |
| 521. | Me | Me | H | 1 | C=S | |
| 522. | Me | Me | H | 2 | C=S | |
| 523. | Me | Me | H | 0 | C=N—N(CH$_3$)$_2$ | |

TABLE 2-continued

Inventive compounds of the general formula (I) in which Q is Q2, Y is $S(O)_m$, $R^5$ is hydrogen and n is 2

| Number | $R^1$ | $R^3$ | $R^4$ | m | X | 1H NMR |
|---|---|---|---|---|---|---|
| 524. | Me | Me | H | 1 | C=N—N(CH$_3$)$_2$ | |
| 525. | Me | Me | H | 2 | C=N—N(CH$_3$)$_2$ | |
| 526. | Me | Me | H | 0 | O | |
| 527. | Me | Me | H | 1 | O | |
| 528. | Me | Me | H | 2 | O | |
| 529. | Me | Me | H | 0 | S | |
| 530. | Me | Me | H | 1 | S | |
| 531. | Me | Me | H | 2 | S | |
| 532. | Me | Me | H | 0 | SO | |
| 533. | Me | Me | H | 1 | SO | |
| 534. | Me | Me | H | 2 | SO | |
| 535. | Me | Me | H | 0 | SO$_2$ | |
| 536. | Me | Me | H | 1 | SO$_2$ | |
| 537. | Me | Me | H | 2 | SO$_2$ | |
| 538. | Me | Me | H | 0 | NMe | |
| 539. | Me | Me | H | 1 | NMe | |
| 540. | Me | Me | H | 2 | NMe | |
| 541. | Et | Me | Me | 0 | CH$_2$ | |
| 542. | Et | Me | Me | 1 | CH$_2$ | |
| 543. | Et | Me | Me | 2 | CH$_2$ | |
| 544. | Et | Me | Me | 0 | CHMe | |
| 545. | Et | Me | Me | 1 | CHMe | |
| 546. | Et | Me | Me | 2 | CHMe | |
| 547. | Et | Me | Me | 0 | C(CH$_3$)$_2$ | |
| 548. | Et | Me | Me | 1 | C(CH$_3$)$_2$ | |
| 549. | Et | Me | Me | 2 | C(CH$_3$)$_2$ | |
| 550. | Et | Me | Me | 0 | C(OC$_2$H$_4$O) | |
| 551. | Et | Me | Me | 1 | C(OC$_2$H$_4$O) | |
| 552. | Et | Me | Me | 2 | C(OC$_2$H$_4$O) | |
| 553. | Et | Me | Me | 0 | C(SC$_2$H$_4$S) | |
| 554. | Et | Me | Me | 1 | C(SC$_2$H$_4$S) | |
| 555. | Et | Me | Me | 2 | C(SC$_2$H$_4$S) | |
| 556. | Et | Me | Me | 0 | CHOMe | |
| 557. | Et | Me | Me | 1 | CHOMe | |
| 558. | Et | Me | Me | 2 | CHOMe | |
| 559. | Et | Me | Me | 0 | CHOEt | |
| 560. | Et | Me | Me | 1 | CHOEt | |
| 561. | Et | Me | Me | 2 | CHOEt | |
| 562. | Et | Me | Me | 0 | CHOiPr | |
| 563. | Et | Me | Me | 1 | CHOiPr | |
| 564. | Et | Me | Me | 2 | CHOiPr | |
| 565. | Et | Me | Me | 0 | CHOCH$_2$cPr | |
| 566. | Et | Me | Me | 1 | CHOCH$_2$cPr | |
| 567. | Et | Me | Me | 2 | CHOCH$_2$cPr | |
| 568. | Et | Me | Me | 0 | CHOC$_2$H$_4$OMe | |
| 569. | Et | Me | Me | 1 | CHOC$_2$H$_4$OMe | |
| 570. | Et | Me | Me | 2 | CHOC$_2$H$_4$OMe | |
| 571. | Et | Me | Me | 0 | CHOCH$_2$CCH | |
| 572. | Et | Me | Me | 1 | CHOCH$_2$CCH | |
| 573. | Et | Me | Me | 2 | CHOCH$_2$CCH | |
| 574. | Et | Me | Me | 0 | CHOCH$_2$CH=CH$_2$ | |
| 575. | Et | Me | Me | 1 | CHOCH$_2$CH=CH$_2$ | |
| 576. | Et | Me | Me | 2 | CHOCH$_2$CH=CH$_2$ | |
| 577. | Et | Me | Me | 0 | 2,6-dimethoxypyrimidin-4-yloxymethyl | |
| 578. | Et | Me | Me | 1 | 2,6-dimethoxypyrimidin-4-yloxymethyl | |
| 579. | Et | Me | Me | 2 | 2,6-dimethoxypyrimidin-4-yloxymethyl | |
| 580. | Et | Me | Me | 0 | pyrazin-2-yloxymethyl | |
| 581. | Et | Me | Me | 1 | pyrazin-2-yloxymethyl | |
| 582. | Et | Me | Me | 2 | pyrazin-2-yloxymethyl | |
| 583. | Et | Me | Me | 0 | pyrazol-1-ylmethyl | |
| 584. | Et | Me | Me | 1 | pyrazol-1-ylmethyl | |
| 585. | Et | Me | Me | 2 | pyrazol-1-ylmethyl | |

TABLE 2-continued

Inventive compounds of the general formula (I) in which Q is Q2, Y is S(O)$_m$, R$^5$ is hydrogen and n is 2

| Number | R$^1$ | R$^3$ | R$^4$ | m | X | 1H NMR |
|---|---|---|---|---|---|---|
| 586. | Et | Me | Me | 0 | (1,2,3-triazol-1-yl)CH | |
| 587. | Et | Me | Me | 1 | (1,2,3-triazol-1-yl)CH | |
| 588. | Et | Me | Me | 2 | (1,2,3-triazol-1-yl)CH | |
| 589. | Et | Me | Me | 0 | (1,2,3-triazol-2-yl)CH | |
| 590. | Et | Me | Me | 1 | (1,2,3-triazol-2-yl)CH | |
| 591. | Et | Me | Me | 2 | (1,2,3-triazol-2-yl)CH | |
| 592. | Et | Me | Me | 0 | CHOC$_2$H$_4$F | |
| 593. | Et | Me | Me | 1 | CHOC$_2$H$_4$F | |
| 594. | Et | Me | Me | 2 | CHOC$_2$H$_4$F | |
| 595. | Et | Me | Me | 0 | C=NOMe | |
| 596. | Et | Me | Me | 1 | C=NOMe | |
| 597. | Et | Me | Me | 2 | C=NOMe | |
| 598. | Et | Me | Me | 0 | C=NOCH$_2$CCH | |
| 599. | Et | Me | Me | 1 | C=NOCH$_2$CCH | |
| 600. | Et | Me | Me | 2 | C=NOCH$_2$CCH | |
| 601. | Et | Me | Me | 0 | C=NOCH$_2$CH=CH$_2$ | |
| 602. | Et | Me | Me | 1 | C=NOCH$_2$CH=CH$_2$ | |
| 603. | Et | Me | Me | 2 | C=NOCH$_2$CH=CH$_2$ | |
| 604. | Et | Me | Me | 0 | C=O | |
| 605. | Et | Me | Me | 1 | C=O | |
| 606. | Et | Me | Me | 2 | C=O | |
| 607. | Et | Me | Me | 0 | C=S | |
| 608. | Et | Me | Me | 1 | C=S | |
| 609. | Et | Me | Me | 2 | C=S | |
| 610. | Et | Me | Me | 0 | C=S | |
| 611. | Et | Me | Me | 1 | C=S | |
| 612. | Et | Me | Me | 2 | C=S | |
| 613. | Et | Me | Me | 0 | C=N—N(CH$_3$)$_2$ | |
| 614. | Et | Me | Me | 1 | C=N—N(CH$_3$)$_2$ | |
| 615. | Et | Me | Me | 2 | C=N—N(CH$_3$)$_2$ | |
| 616. | Et | Me | Me | 0 | O | |
| 617. | Et | Me | Me | 1 | O | |
| 618. | Et | Me | Me | 2 | O | |
| 619. | Et | Me | Me | 0 | S | |
| 620. | Et | Me | Me | 1 | S | |
| 621. | Et | Me | Me | 2 | S | |
| 622. | Et | Me | Me | 0 | SO | |
| 623. | Et | Me | Me | 1 | SO | |
| 624. | Et | Me | Me | 2 | SO | |
| 625. | Et | Me | Me | 0 | SO$_2$ | |
| 626. | Et | Me | Me | 1 | SO$_2$ | |
| 627. | Et | Me | Me | 2 | SO$_2$ | |
| 628. | Et | Me | Me | 0 | NMe | |
| 629. | Et | Me | Me | 1 | NMe | |
| 630. | Et | Me | Me | 2 | NMe | |
| 631. | Et | Me | H | 0 | CH$_2$ | |
| 632. | Et | Me | H | 1 | CH$_2$ | |
| 633. | Et | Me | H | 2 | CH$_2$ | |
| 634. | Et | Me | H | 0 | CHMe | |
| 635. | Et | Me | H | 1 | CHMe | |
| 636. | Et | Me | H | 2 | CHMe | |
| 637. | Et | Me | H | 0 | C(CH$_3$)$_2$ | |
| 638. | Et | Me | H | 1 | C(CH$_3$)$_2$ | |
| 639. | Et | Me | H | 2 | C(CH$_3$)$_2$ | |
| 640. | Et | Me | H | 0 | C(OC$_2$H$_4$O) | |
| 641. | Et | Me | H | 1 | C(OC$_2$H$_4$O) | |
| 642. | Et | Me | H | 2 | C(OC$_2$H$_4$O) | |
| 643. | Et | Me | H | 0 | C(SC$_2$H$_4$S) | |
| 644. | Et | Me | H | 1 | C(SC$_2$H$_4$S) | |
| 645. | Et | Me | H | 2 | C(SC$_2$H$_4$S) | |
| 646. | Et | Me | H | 0 | CHOMe | |
| 647. | Et | Me | H | 1 | CHOMe | |
| 648. | Et | Me | H | 2 | CHOMe | |
| 649. | Et | Me | H | 0 | CHOEt | |
| 650. | Et | Me | H | 1 | CHOEt | |
| 651. | Et | Me | H | 2 | CHOEt | |
| 652. | Et | Me | H | 0 | CHOiPr | |
| 653. | Et | Me | H | 1 | CHOiPr | |
| 654. | Et | Me | H | 2 | CHOiPr | |
| 655. | Et | Me | H | 0 | CHOCH$_2$cPr | |
| 656. | Et | Me | H | 1 | CHOCH$_2$cPr | |
| 657. | Et | Me | H | 2 | CHOCH$_2$cPr | |
| 658. | Et | Me | H | 0 | CHOC$_2$H$_4$OMe | |
| 659. | Et | Me | H | 1 | CHOC$_2$H$_4$OMe | |
| 660. | Et | Me | H | 2 | CHOC$_2$H$_4$OMe | |
| 661. | Et | Me | H | 0 | CHOCH$_2$CCH | |
| 662. | Et | Me | H | 1 | CHOCH$_2$CCH | |
| 663. | Et | Me | H | 2 | CHOCH$_2$CCH | |
| 664. | Et | Me | H | 0 | CHOCH$_2$CH=CH$_2$ | |
| 665. | Et | Me | H | 1 | CHOCH$_2$CH=CH$_2$ | |
| 666. | Et | Me | H | 2 | CHOCH$_2$CH=CH$_2$ | |
| 667. | Et | Me | H | 0 | 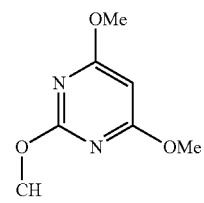 | |

TABLE 2-continued

Inventive compounds of the general formula (I) in which Q is Q2, Y is S(O)$_m$, R$^5$ is hydrogen and n is 2

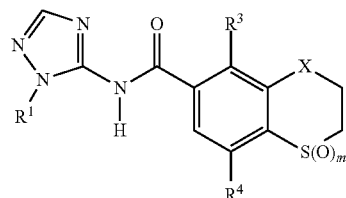

| Number | R$^1$ | R$^3$ | R$^4$ | m | X | 1H NMR |
|---|---|---|---|---|---|---|
| 668. | Et | Me | H | 1 | pyrimidine-2-yloxymethyl (4,6-diOMe) | |
| 669. | Et | Me | H | 2 | pyrimidine-2-yloxymethyl (4,6-diOMe) | |
| 670. | Et | Me | H | 0 | pyrazin-2-yloxymethyl | |
| 671. | Et | Me | H | 1 | pyrazin-2-yloxymethyl | |
| 672. | Et | Me | H | 2 | pyrazin-2-yloxymethyl | |
| 673. | Et | Me | H | 0 | pyrazol-1-ylmethyl | |
| 674. | Et | Me | H | 1 | pyrazol-1-ylmethyl | |
| 675. | Et | Me | H | 2 | pyrazol-1-ylmethyl | |

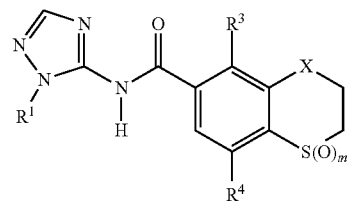

| Number | R$^1$ | R$^3$ | R$^4$ | m | X | 1H NMR |
|---|---|---|---|---|---|---|
| 676. | Et | Me | H | 0 | 1,2,3-triazol-1-ylmethyl | |
| 677. | Et | Me | H | 1 | 1,2,3-triazol-1-ylmethyl | |
| 678. | Et | Me | H | 2 | 1,2,3-triazol-1-ylmethyl | |
| 679. | Et | Me | H | 0 | 1,2,3-triazol-2-ylmethyl | |
| 680. | Et | Me | H | 1 | 1,2,3-triazol-2-ylmethyl | |
| 681. | Et | Me | H | 2 | 1,2,3-triazol-2-ylmethyl | |
| 682. | Et | Me | H | 0 | CHOC$_2$H$_4$F | |
| 683. | Et | Me | H | 1 | CHOC$_2$H$_4$F | |
| 684. | Et | Me | H | 2 | CHOC$_2$H$_4$F | |
| 685. | Et | Me | H | 0 | C=NOMe | |
| 686. | Et | Me | H | 1 | C=NOMe | |
| 687. | Et | Me | H | 2 | C=NOMe | |
| 688. | Et | Me | H | 0 | C=NOCH$_2$CCH | |
| 689. | Et | Me | H | 1 | C=NOCH$_2$CCH | |
| 690. | Et | Me | H | 2 | C=NOCH$_2$CCH | |
| 691. | Et | Me | H | 0 | C=NOCH$_2$CH=CH$_2$ | |
| 692. | Et | Me | H | 1 | C=NOCH$_2$CH=CH$_2$ | |
| 693. | Et | Me | H | 2 | C=NOCH$_2$CH=CH$_2$ | |
| 694. | Et | Me | H | 0 | C=O | |
| 695. | Et | Me | H | 1 | C=O | |
| 696. | Et | Me | H | 2 | C=O | |
| 697. | Et | Me | H | 0 | C=S | |
| 698. | Et | Me | H | 1 | C=S | |
| 699. | Et | Me | H | 2 | C=S | |
| 700. | Et | Me | H | 0 | C=S | |
| 701. | Et | Me | H | 1 | C=S | |
| 702. | Et | Me | H | 2 | C=S | |
| 703. | Et | Me | H | 0 | C=N—N(CH$_3$)$_2$ | |
| 704. | Et | Me | H | 1 | C=N—N(CH$_3$)$_2$ | |

TABLE 2-continued

Inventive compounds of the general formula (I) in which Q is Q2, Y is S(O)$_m$, R$^5$ is hydrogen and n is 2

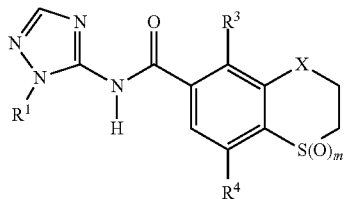

| Number | R$^1$ | R$^3$ | R$^4$ | m | X | 1H NMR |
|---|---|---|---|---|---|---|
| 705. | Et | Me | H | 2 | C=N—N(CH$_3$)$_2$ | |
| 706. | Et | Me | H | 0 | O | |
| 707. | Et | Me | H | 1 | O | |
| 708. | Et | Me | H | 2 | O | |
| 709. | Et | Me | H | 0 | S | |
| 710. | Et | Me | H | 1 | S | |
| 711. | Et | Me | H | 2 | S | |
| 712. | Et | Me | H | 0 | SO | |
| 713. | Et | Me | H | 1 | SO | |
| 714. | Et | Me | H | 2 | SO | |
| 715. | Et | Me | H | 0 | SO$_2$ | |
| 716. | Et | Me | H | 1 | SO$_2$ | |
| 717. | Et | Me | H | 2 | SO$_2$ | |
| 718. | Et | Me | H | 0 | NMe | |
| 719. | Et | Me | H | 1 | NMe | |
| 720. | Et | Me | H | 2 | NMe | |

TABLE 3

Inventive compounds of the general formula (I) in which Q is Q3, Y is S(O)$_m$, R$^5$ is hydrogen and n is 2

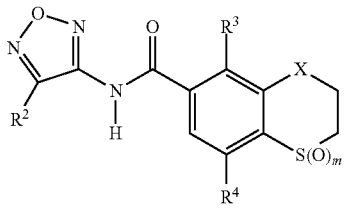

| No. | R$^2$ | R$^3$ | R$^4$ | m | X | 1H NMR |
|---|---|---|---|---|---|---|
| 721. | Me | Me | Me | 0 | CH$_2$ | |
| 722. | Me | Me | Me | 1 | CH$_2$ | |
| 723. | Me | Me | Me | 2 | CH$_2$ | |
| 724. | Me | Me | Me | 0 | CHMe | |
| 725. | Me | Me | Me | 1 | CHMe | |
| 726. | Me | Me | Me | 2 | CHMe | |
| 727. | Me | Me | Me | 0 | C(CH$_3$)$_2$ | |
| 728. | Me | Me | Me | 1 | C(CH$_3$)$_2$ | |
| 729. | Me | Me | Me | 2 | C(CH$_3$)$_2$ | |
| 730. | Me | Me | Me | 0 | C(OC$_2$H$_4$O) | |
| 731. | Me | Me | Me | 1 | C(OC$_2$H$_4$O) | |
| 732. | Me | Me | Me | 2 | C(OC$_2$H$_4$O) | |
| 733. | Me | Me | Me | 0 | C(SC$_2$H$_4$S) | |
| 734. | Me | Me | Me | 1 | C(SC$_2$H$_4$S) | |
| 735. | Me | Me | Me | 2 | C(SC$_2$H$_4$S) | |
| 736. | Me | Me | Me | 0 | CHOMe | |
| 737. | Me | Me | Me | 1 | CHOMe | |
| 738. | Me | Me | Me | 2 | CHOMe | |
| 739. | Me | Me | Me | 0 | CHOEt | |
| 740. | Me | Me | Me | 1 | CHOEt | |
| 741. | Me | Me | Me | 2 | CHOEt | |
| 742. | Me | Me | Me | 0 | CHOiPr | |
| 743. | Me | Me | Me | 1 | CHOiPr | |
| 744. | Me | Me | Me | 2 | CHOiPr | |
| 745. | Me | Me | Me | 0 | CHOCH$_2$cPr | |
| 746. | Me | Me | Me | 1 | CHOCH$_2$cPr | |
| 747. | Me | Me | Me | 2 | CHOCH$_2$cPr | |
| 748. | Me | Me | Me | 0 | CHOC$_2$H$_4$OMe | |

TABLE 3-continued

Inventive compounds of the general formula (I) in which Q is Q3, Y is S(O)$_m$, R$^5$ is hydrogen and n is 2

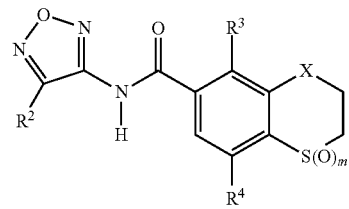

| No. | R$^2$ | R$^3$ | R$^4$ | m | X | 1H NMR |
|---|---|---|---|---|---|---|
| 749. | Me | Me | Me | 1 | CHOC$_2$H$_4$OMe | |
| 750. | Me | Me | Me | 2 | CHOC$_2$H$_4$OMe | |
| 751. | Me | Me | Me | 0 | CHOCH$_2$CCH | |
| 752. | Me | Me | Me | 1 | CHOCH$_2$CCH | |
| 753. | Me | Me | Me | 2 | CHOCH$_2$CCH | |
| 754. | Me | Me | Me | 0 | CHOCH$_2$CH=CH$_2$ | |
| 755. | Me | Me | Me | 1 | CHOCH$_2$CH=CH$_2$ | |
| 756. | Me | Me | Me | 2 | CHOCH$_2$CH=CH$_2$ | |
| 757. | Me | Me | Me | 0 | (4,6-dimethoxypyrimidin-2-yloxy)CH | |
| 758. | Me | Me | Me | 1 | (4,6-dimethoxypyrimidin-2-yloxy)CH | |
| 759. | Me | Me | Me | 2 | (4,6-dimethoxypyrimidin-2-yloxy)CH | |
| 760. | Me | Me | Me | 0 | (pyrazin-2-yloxy)CH | |
| 761. | Me | Me | Me | 1 | (pyrazin-2-yloxy)CH | |
| 762. | Me | Me | Me | 2 | (pyrazin-2-yloxy)CH | DMSO-d$_6$, 400 MHz: 11.42 (s, 1H), 8.39 (s, 1H), 8.35-8.30 (m, 2H), 7.70 (s, 1H), 6.52 (dd, 1H), 3.79-3.69 (m, 1H), 3.61-3.52 (m, 1H), 2.80-2.60 (m, 5H), 2.38 (s, 3H), 2.21 (s, 3H) |

TABLE 3-continued

Inventive compounds of the general formula (I) in which Q is Q3, Y is S(O)$_m$, R$^5$ is hydrogen and n is 2

| No. | R$^2$ | R$^3$ | R$^4$ | m | X | 1H NMR |
|---|---|---|---|---|---|---|
| 763. | Me | Me | Me | 0 | N-pyrazolyl-CH | |
| 764. | Me | Me | Me | 1 | N-pyrazolyl-CH | |
| 765. | Me | Me | Me | 2 | N-pyrazolyl-CH | |
| 766. | Me | Me | Me | 0 | N-triazolyl-CH | |
| 767. | Me | Me | Me | 1 | N-triazolyl-CH | |
| 768. | Me | Me | Me | 2 | N-triazolyl-CH | |
| 769. | Me | Me | Me | 0 | N-triazolyl-CH | |
| 770. | Me | Me | Me | 1 | N-triazolyl-CH | |
| 771. | Me | Me | Me | 2 | N-triazolyl-CH | |
| 772. | Me | Me | Me | 0 | CHOC$_2$H$_4$F | |
| 773. | Me | Me | Me | 1 | CHOC$_2$H$_4$F | |
| 774. | Me | Me | Me | 2 | CHOC$_2$H$_4$F | |
| 775. | Me | Me | Me | 0 | C=NOMe | |
| 776. | Me | Me | Me | 1 | C=NOMe | |
| 777. | Me | Me | Me | 2 | C=NOMe | |
| 778. | Me | Me | Me | 0 | C=NOCH$_2$CCH | |
| 779. | Me | Me | Me | 1 | C=NOCH$_2$CCH | |
| 780. | Me | Me | Me | 2 | C=NOCH$_2$CCH | |
| 781. | Me | Me | Me | 0 | C=NOCH$_2$CH=CH$_2$ | |
| 782. | Me | Me | Me | 1 | C=NOCH$_2$CH=CH$_2$ | |
| 783. | Me | Me | Me | 2 | C=NOCH$_2$CH=CH$_2$ | |
| 784. | Me | Me | Me | 0 | C=O | |
| 785. | Me | Me | Me | 1 | C=O | |
| 786. | Me | Me | Me | 2 | C=O | |
| 787. | Me | Me | Me | 0 | C=S | |
| 788. | Me | Me | Me | 1 | C=S | |
| 789. | Me | Me | Me | 2 | C=S | |
| 790. | Me | Me | Me | 0 | C=S | |
| 791. | Me | Me | Me | 1 | C=S | |
| 792. | Me | Me | Me | 2 | C=S | |
| 793. | Me | Me | Me | 0 | C=N—N(CH$_3$)$_2$ | |
| 794. | Me | Me | Me | 1 | C=N—N(CH$_3$)$_2$ | |
| 795. | Me | Me | Me | 2 | C=N—N(CH$_3$)$_2$ | |
| 796. | Me | Me | Me | 0 | O | |
| 797. | Me | Me | Me | 1 | O | |
| 798. | Me | Me | Me | 2 | O | |
| 799. | Me | Me | Me | 0 | S | |
| 800. | Me | Me | Me | 1 | S | |
| 801. | Me | Me | Me | 2 | S | |
| 802. | Me | Me | Me | 0 | SO | |
| 803. | Me | Me | Me | 1 | SO | |
| 804. | Me | Me | Me | 2 | SO | |
| 805. | Me | Me | Me | 0 | SO$_2$ | |
| 806. | Me | Me | Me | 1 | SO$_2$ | |
| 807. | Me | Me | Me | 2 | SO$_2$ | |
| 808. | Me | Me | Me | 0 | NMe | |
| 809. | Me | Me | Me | 1 | NMe | |
| 810. | Me | Me | Me | 2 | NMe | |
| 811. | Me | Me | H | 0 | CH$_2$ | |
| 812. | Me | Me | H | 1 | CH$_2$ | |
| 813. | Me | Me | H | 2 | CH$_2$ | |
| 814. | Me | Me | H | 0 | CHMe | |
| 815. | Me | Me | H | 1 | CHMe | |
| 816. | Me | Me | H | 2 | CHMe | |
| 817. | Me | Me | H | 0 | C(CH$_3$)$_2$ | |
| 818. | Me | Me | H | 1 | C(CH$_3$)$_2$ | |
| 819. | Me | Me | H | 2 | C(CH$_3$)$_2$ | |
| 820. | Me | Me | H | 0 | C(OC$_2$H$_4$O) | |
| 821. | Me | Me | H | 1 | C(OC$_2$H$_4$O) | |
| 822. | Me | Me | H | 2 | C(OC$_2$H$_4$O) | |
| 823. | Me | Me | H | 0 | C(SC$_2$H$_4$S) | |
| 824. | Me | Me | H | 1 | C(SC$_2$H$_4$S) | |
| 825. | Me | Me | H | 2 | C(SC$_2$H$_4$S) | |
| 826. | Me | Me | H | 0 | CHOMe | |
| 827. | Me | Me | H | 1 | CHOMe | |
| 828. | Me | Me | H | 2 | CHOMe | |
| 829. | Me | Me | H | 0 | CHOEt | |
| 830. | Me | Me | H | 1 | CHOEt | |
| 831. | Me | Me | H | 2 | CHOEt | |
| 832. | Me | Me | H | 0 | CHOiPr | |
| 833. | Me | Me | H | 1 | CHOiPr | |
| 834. | Me | Me | H | 2 | CHOiPr | |
| 835. | Me | Me | H | 0 | CHOCH$_2$cPr | |
| 836. | Me | Me | H | 1 | CHOCH$_2$cPr | |

TABLE 3-continued

Inventive compounds of the general formula (I) in which Q is Q3, Y is S(O)$_m$, R$^5$ is hydrogen and n is 2

| No. | R$^2$ | R$^3$ | R$^4$ | m | X | 1H NMR |
|---|---|---|---|---|---|---|
| 837. | Me | Me | H | 2 | CHOCH$_2$cPr | |
| 838. | Me | Me | H | 0 | CHOC$_2$H$_4$OMe | |
| 839. | Me | Me | H | 1 | CHOC$_2$H$_4$OMe | |
| 840. | Me | Me | H | 2 | CHOC$_2$H$_4$OMe | |
| 841. | Me | Me | H | 0 | CHOCH$_2$CCH | |
| 842. | Me | Me | H | 1 | CHOCH$_2$CCH | |
| 843. | Me | Me | H | 2 | CHOCH$_2$CCH | |
| 844. | Me | Me | H | 0 | CHOCH$_2$CH=CH$_2$ | |
| 845. | Me | Me | H | 1 | CHOCH$_2$CH=CH$_2$ | |
| 846. | Me | Me | H | 2 | CHOCH$_2$CH=CH$_2$ | |
| 847. | Me | Me | H | 0 | 4,6-dimethoxypyrimidin-2-yloxymethyl | |
| 848. | Me | Me | H | 1 | 4,6-dimethoxypyrimidin-2-yloxymethyl | |
| 849. | Me | Me | H | 2 | 4,6-dimethoxypyrimidin-2-yloxymethyl | |
| 850. | Me | Me | H | 0 | pyrazin-2-yloxymethyl | |
| 851. | Me | Me | H | 1 | pyrazin-2-yloxymethyl | |
| 852. | Me | Me | H | 2 | pyrazin-2-yloxymethyl | |
| 853. | Me | Me | H | 0 | pyrazol-1-ylmethyl | |
| 854. | Me | Me | H | 1 | pyrazol-1-ylmethyl | |
| 855. | Me | Me | H | 2 | pyrazol-1-ylmethyl | |
| 856. | Me | Me | H | 0 | 1,2,3-triazol-1-ylmethyl | |
| 857. | Me | Me | H | 1 | 1,2,3-triazol-1-ylmethyl | |
| 858. | Me | Me | H | 2 | 1,2,3-triazol-1-ylmethyl | |
| 859. | Me | Me | H | 0 | 1,2,3-triazol-2-ylmethyl | |
| 860. | Me | Me | H | 1 | 1,2,3-triazol-2-ylmethyl | |
| 861. | Me | Me | H | 2 | 1,2,3-triazol-2-ylmethyl | |
| 862. | Me | Me | H | 0 | CHOC$_2$H$_4$F | |

TABLE 3-continued

Inventive compounds of the general formula (I) in which Q is Q3, Y is $S(O)_m$, $R^5$ is hydrogen and n is 2

| No. | $R^2$ | $R^3$ | $R^4$ | m | X | 1H NMR |
|---|---|---|---|---|---|---|
| 863. | Me | Me | H | 1 | $CHOC_2H_4F$ | |
| 864. | Me | Me | H | 2 | $CHOC_2H_4F$ | |
| 865. | Me | Me | H | 0 | C=NOMe | |
| 866. | Me | Me | H | 1 | C=NOMe | |
| 867. | Me | Me | H | 2 | C=NOMe | |
| 868. | Me | Me | H | 0 | $C=NOCH_2CCH$ | |
| 869. | Me | Me | H | 1 | $C=NOCH_2CCH$ | |
| 870. | Me | Me | H | 2 | $C=NOCH_2CCH$ | |
| 871. | Me | Me | H | 0 | $C=NOCH_2CH=CH_2$ | |
| 872. | Me | Me | H | 1 | $C=NOCH_2CH=CH_2$ | |
| 873. | Me | Me | H | 2 | $C=NOCH_2CH=CH_2$ | |
| 874. | Me | Me | H | 0 | C=O | |
| 875. | Me | Me | H | 1 | C=O | |
| 876. | Me | Me | H | 2 | C=O | |
| 877. | Me | Me | H | 0 | C=S | |
| 878. | Me | Me | H | 1 | C=S | |
| 879. | Me | Me | H | 2 | C=S | |
| 880. | Me | Me | H | 0 | C=S | |
| 881. | Me | Me | H | 1 | C=S | |
| 882. | Me | Me | H | 2 | C=S | |
| 883. | Me | Me | H | 0 | $C=N-N(CH_3)_2$ | |
| 884. | Me | Me | H | 1 | $C=N-N(CH_3)_2$ | |
| 885. | Me | Me | H | 2 | $C=N-N(CH_3)_2$ | |
| 886. | Me | Me | H | 0 | O | |
| 887. | Me | Me | H | 1 | O | |
| 888. | Me | Me | H | 2 | O | |
| 889. | Me | Me | H | 0 | S | |
| 890. | Me | Me | H | 1 | S | |
| 891. | Me | Me | H | 2 | S | |
| 892. | Me | Me | H | 0 | SO | |
| 893. | Me | Me | H | 1 | SO | |
| 894. | Me | Me | H | 2 | SO | |
| 895. | Me | Me | H | 0 | $SO_2$ | |
| 896. | Me | Me | H | 1 | $SO_2$ | |
| 897. | Me | Me | H | 2 | $SO_2$ | |
| 898. | Me | Me | H | 0 | NMe | |
| 899. | Me | Me | H | 1 | NMe | |
| 900. | Me | Me | H | 2 | NMe | |
| 901. | Et | Me | Me | 0 | $CH_2$ | |
| 902. | Et | Me | Me | 1 | $CH_2$ | |
| 903. | Et | Me | Me | 2 | $CH_2$ | |
| 904. | Et | Me | Me | 0 | CHMe | |
| 905. | Et | Me | Me | 1 | CHMe | |
| 906. | Et | Me | Me | 2 | CHMe | |
| 907. | Et | Me | Me | 0 | $C(CH_3)_2$ | |
| 908. | Et | Me | Me | 1 | $C(CH_3)_2$ | |
| 909. | Et | Me | Me | 2 | $C(CH_3)_2$ | |
| 910. | Et | Me | Me | 0 | $C(OC_2H_4O)$ | |
| 911. | Et | Me | Me | 1 | $C(OC_2H_4O)$ | |
| 912. | Et | Me | Me | 2 | $C(OC_2H_4O)$ | |
| 913. | Et | Me | Me | 0 | $C(SC_2H_4S)$ | |
| 914. | Et | Me | Me | 1 | $C(SC_2H_4S)$ | |
| 915. | Et | Me | Me | 2 | $C(SC_2H_4S)$ | |
| 916. | Et | Me | Me | 0 | CHOMe | |
| 917. | Et | Me | Me | 1 | CHOMe | |
| 918. | Et | Me | Me | 2 | CHOMe | |
| 919. | Et | Me | Me | 0 | CHOEt | |
| 920. | Et | Me | Me | 1 | CHOEt | |
| 921. | Et | Me | Me | 2 | CHOEt | |
| 922. | Et | Me | Me | 0 | CHOiPr | |
| 923. | Et | Me | Me | 1 | CHOiPr | |
| 924. | Et | Me | Me | 2 | CHOiPr | |
| 925. | Et | Me | Me | 0 | $CHOCH_2cPr$ | |
| 926. | Et | Me | Me | 1 | $CHOCH_2cPr$ | |
| 927. | Et | Me | Me | 2 | $CHOCH_2cPr$ | |
| 928. | Et | Me | Me | 0 | $CHOC_2H_4OMe$ | |
| 929. | Et | Me | Me | 1 | $CHOC_2H_4OMe$ | |
| 930. | Et | Me | Me | 2 | $CHOC_2H_4OMe$ | |
| 931. | Et | Me | Me | 0 | $CHOCH_2CCH$ | |
| 932. | Et | Me | Me | 1 | $CHOCH_2CCH$ | |
| 933. | Et | Me | Me | 2 | $CHOCH_2CCH$ | |
| 934. | Et | Me | Me | 0 | $CHOCH_2CH=CH_2$ | |
| 935. | Et | Me | Me | 1 | $CHOCH_2CH=CH_2$ | |
| 936. | Et | Me | Me | 2 | $CHOCH_2CH=CH_2$ | |
| 937. | Et | Me | Me | 0 | (4,6-dimethoxypyrimidin-2-yloxy)CH | |
| 938. | Et | Me | Me | 1 | (4,6-dimethoxypyrimidin-2-yloxy)CH | |
| 939. | Et | Me | Me | 2 | (4,6-dimethoxypyrimidin-2-yloxy)CH | |
| 940. | Et | Me | Me | 0 | (pyrazin-2-yloxy)CH | |
| 941. | Et | Me | Me | 1 | (pyrazin-2-yloxy)CH | |

TABLE 3-continued

Inventive compounds of the general formula (I) in which Q is Q3, Y is S(O)$_m$, R$^5$ is hydrogen and n is 2

(Structure: furazan-carboxamide linked to benzo-fused ring with X bridge and S(O)$_m$, bearing R$^2$, R$^3$, R$^4$ substituents)

| No. | R$^2$ | R$^3$ | R$^4$ | m | X | 1H NMR |
|---|---|---|---|---|---|---|
| 942. | Et | Me | Me | 2 | pyrazinyl-O-CH | DMSO-d$_6$, 400 MHz: 11.35 (s, 1H), 8.39 (s, 1H), 8.34-8.30 (m, 2H), 7.67 (s, 1H), 6.52 (dd, 1H), 3.80-3.71 (m, 1H), 3.60-3.53 (m, 1H), 2.82-2.60 (m, 7H), 2.20 (s, 3H), 1.26 (t, 3H) |
| 943. | Et | Me | Me | 0 | pyrazol-1-yl-CH | |
| 944. | Et | Me | Me | 1 | pyrazol-1-yl-CH | |
| 945. | Et | Me | Me | 2 | pyrazol-1-yl-CH | |
| 946. | Et | Me | Me | 0 | 1,2,3-triazol-1-yl-CH | |
| 947. | Et | Me | Me | 1 | 1,2,3-triazol-1-yl-CH | |
| 948. | Et | Me | Me | 2 | 1,2,3-triazol-1-yl-CH | |
| 949. | Et | Me | Me | 0 | 1,2,3-triazol-2-yl-CH | |
| 950. | Et | Me | Me | 1 | 1,2,3-triazol-2-yl-CH | |
| 951. | Et | Me | Me | 2 | 1,2,3-triazol-2-yl-CH | |
| 952. | Et | Me | Me | 0 | CHOC$_2$H$_4$F | |
| 953. | Et | Me | Me | 1 | CHOC$_2$H$_4$F | |
| 954. | Et | Me | Me | 2 | CHOC$_2$H$_4$F | |
| 955. | Et | Me | Me | 0 | C=NOMe | |
| 956. | Et | Me | Me | 1 | C=NOMe | |
| 957. | Et | Me | Me | 2 | C=NOMe | |
| 958. | Et | Me | Me | 0 | C=NOCH$_2$CCH | |
| 959. | Et | Me | Me | 1 | C=NOCH$_2$CCH | |
| 960. | Et | Me | Me | 2 | C=NOCH$_2$CCH | |
| 961. | Et | Me | Me | 0 | C=NOCH$_2$CH=CH$_2$ | |
| 962. | Et | Me | Me | 1 | C=NOCH$_2$CH=CH$_2$ | |
| 963. | Et | Me | Me | 2 | C=NOCH$_2$CH=CH$_2$ | |
| 964. | Et | Me | Me | 0 | C=O | |
| 965. | Et | Me | Me | 1 | C=O | |
| 966. | Et | Me | Me | 2 | C=O | |
| 967. | Et | Me | Me | 0 | C=S | |
| 968. | Et | Me | Me | 1 | C=S | |
| 969. | Et | Me | Me | 2 | C=S | |
| 970. | Et | Me | Me | 0 | C=S | |
| 971. | Et | Me | Me | 1 | C=S | |
| 972. | Et | Me | Me | 2 | C=S | |
| 973. | Et | Me | Me | 0 | C=N—N(CH$_3$)$_2$ | |
| 974. | Et | Me | Me | 1 | C=N—N(CH$_3$)$_2$ | |
| 975. | Et | Me | Me | 2 | C=N—N(CH$_3$)$_2$ | |
| 976. | Et | Me | Me | 0 | O | |
| 977. | Et | Me | Me | 1 | O | |
| 978. | Et | Me | Me | 2 | O | |
| 979. | Et | Me | Me | 0 | S | |
| 980. | Et | Me | Me | 1 | S | |
| 981. | Et | Me | Me | 2 | S | |
| 982. | Et | Me | Me | 0 | SO | |
| 983. | Et | Me | Me | 1 | SO | |
| 984. | Et | Me | Me | 2 | SO | |
| 985. | Et | Me | Me | 0 | SO$_2$ | |
| 986. | Et | Me | Me | 1 | SO$_2$ | |
| 987. | Et | Me | Me | 2 | SO$_2$ | |
| 988. | Et | Me | Me | 0 | NMe | |
| 989. | Et | Me | Me | 1 | NMe | |
| 990. | Et | Me | Me | 2 | NMe | |
| 991. | Et | Me | H | 0 | CH$_2$ | |
| 992. | Et | Me | H | 1 | CH$_2$ | |
| 993. | Et | Me | H | 2 | CH$_2$ | |
| 994. | Et | Me | H | 0 | CHMe | |
| 995. | Et | Me | H | 1 | CHMe | |
| 996. | Et | Me | H | 2 | CHMe | |
| 997. | Et | Me | H | 0 | C(CH$_3$)$_2$ | |
| 998. | Et | Me | H | 1 | C(CH$_3$)$_2$ | |
| 999. | Et | Me | H | 2 | C(CH$_3$)$_2$ | |
| 1000 | Et | Me | H | 0 | C(OC$_2$H$_4$O) | |
| 1001 | Et | Me | H | 1 | C(OC$_2$H$_4$O) | |
| 1002 | Et | Me | H | 2 | C(OC$_2$H$_4$O) | |
| 1003 | Et | Me | H | 0 | C(SC$_2$H$_4$S) | |
| 1004 | Et | Me | H | 1 | C(SC$_2$H$_4$S) | |
| 1005 | Et | Me | H | 2 | C(SC$_2$H$_4$S) | |
| 1006 | Et | Me | H | 0 | CHOMe | |
| 1007 | Et | Me | H | 1 | CHOMe | |

TABLE 3-continued

Inventive compounds of the general formula (I) in which Q is Q3, Y is S(O)$_m$, R$^5$ is hydrogen and n is 2

Structure: furazan-NH-C(O)- attached to benzo-fused ring containing X and S(O)$_m$, with substituents R$^2$, R$^3$, R$^4$.

| No. | R$^2$ | R$^3$ | R$^4$ | m | X | 1H NMR |
|---|---|---|---|---|---|---|
| 1008 | Et | Me | H | 2 | CHOMe | |
| 1009 | Et | Me | H | 0 | CHOEt | |
| 1010 | Et | Me | H | 1 | CHOEt | |
| 1011 | Et | Me | H | 2 | CHOEt | |
| 1012 | Et | Me | H | 0 | CHOiPr | |
| 1013 | Et | Me | H | 1 | CHOiPr | |
| 1014 | Et | Me | H | 2 | CHOiPr | |
| 1015 | Et | Me | H | 0 | CHOCH$_2$cPr | |
| 1016 | Et | Me | H | 1 | CHOCH$_2$cPr | |
| 1017 | Et | Me | H | 2 | CHOCH$_2$cPr | |
| 1018 | Et | Me | H | 0 | CHOC$_2$H$_4$OMe | |
| 1019 | Et | Me | H | 1 | CHOC$_2$H$_4$OMe | |
| 1020 | Et | Me | H | 2 | CHOC$_2$H$_4$OMe | |
| 1021 | Et | Me | H | 0 | CHOCH$_2$CCH | |
| 1022 | Et | Me | H | 1 | CHOCH$_2$CCH | |
| 1023 | Et | Me | H | 2 | CHOCH$_2$CCH | |
| 1024 | Et | Me | H | 0 | CHOCH$_2$CH=CH$_2$ | |
| 1025 | Et | Me | H | 1 | CHOCH$_2$CH=CH$_2$ | |
| 1026 | Et | Me | H | 2 | CHOCH$_2$CH=CH$_2$ | |
| 1027 | Et | Me | H | 0 | CH–O–(4,6-dimethoxypyrimidin-2-yl) | |
| 1028 | Et | Me | H | 1 | CH–O–(4,6-dimethoxypyrimidin-2-yl) | |
| 1029 | Et | Me | H | 2 | CH–O–(4,6-dimethoxypyrimidin-2-yl) | |
| 1030 | Et | Me | H | 0 | CH–O–(pyrazin-2-yl) | |
| 1031 | Et | Me | H | 1 | CH–O–(pyrazin-2-yl) | |
| 1032 | Et | Me | H | 2 | CH–O–(pyrazin-2-yl) | |
| 1033 | Et | Me | H | 0 | CH–(pyrazol-1-yl) | |
| 1034 | Et | Me | H | 1 | CH–(pyrazol-1-yl) | |
| 1035 | Et | Me | H | 2 | CH–(pyrazol-1-yl) | |
| 1036 | Et | Me | H | 0 | CH–(1,2,3-triazol-1-yl) | |
| 1037 | Et | Me | H | 1 | CH–(1,2,3-triazol-1-yl) | |
| 1038 | Et | Me | H | 2 | CH–(1,2,3-triazol-1-yl) | |
| 1039 | Et | Me | H | 0 | CH–(1,2,3-triazol-2-yl) | |
| 1040 | Et | Me | H | 1 | CH–(1,2,3-triazol-2-yl) | |

TABLE 3-continued

Inventive compounds of the general formula (I) in which Q is Q3, Y is S(O)$_m$, R$^5$ is hydrogen and n is 2

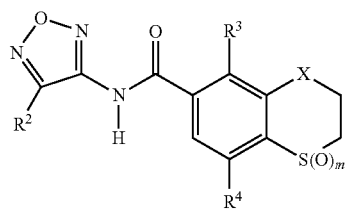

| No. | R$^2$ | R$^3$ | R$^4$ | m | X | 1H NMR |
|---|---|---|---|---|---|---|
| 1041 | Et | Me | H | 2 | ![triazole-CH] | |
| 1042 | Et | Me | H | 0 | CHOC$_2$H$_4$F | |
| 1043 | Et | Me | H | 1 | CHOC$_2$H$_4$F | |
| 1044 | Et | Me | H | 2 | CHOC$_2$H$_4$F | |
| 1045 | Et | Me | H | 0 | C=NOMe | |
| 1046 | Et | Me | H | 1 | C=NOMe | |
| 1047 | Et | Me | H | 2 | C=NOMe | |
| 1048 | Et | Me | H | 0 | C=NOCH$_2$CCH | |
| 1049 | Et | Me | H | 1 | C=NOCH$_2$CCH | |
| 1050 | Et | Me | H | 2 | C=NOCH$_2$CCH | |
| 1051 | Et | Me | H | 0 | C=NOCH$_2$CH=CH$_2$ | |
| 1052 | Et | Me | H | 1 | C=NOCH$_2$CH=CH$_2$ | |
| 1053 | Et | Me | H | 2 | C=NOCH$_2$CH=CH$_2$ | |
| 1054 | Et | Me | H | 0 | C=O | |
| 1055 | Et | Me | H | 1 | C=O | |
| 1056 | Et | Me | H | 2 | C=O | |
| 1057 | Et | Me | H | 0 | C=S | |
| 1058 | Et | Me | H | 1 | C=S | |
| 1059 | Et | Me | H | 2 | C=S | |
| 1060 | Et | Me | H | 0 | C=S | |
| 1061 | Et | Me | H | 1 | C=S | |
| 1062 | Et | Me | H | 2 | C=S | |
| 1063 | Et | Me | H | 0 | C=N—N(CH$_3$)$_2$ | |
| 1064 | Et | Me | H | 1 | C=N—N(CH$_3$)$_2$ | |
| 1065 | Et | Me | H | 2 | C=N—N(CH$_3$)$_2$ | |
| 1066 | Et | Me | H | 0 | O | |
| 1067 | Et | Me | H | 1 | O | |
| 1068 | Et | Me | H | 2 | O | |
| 1069 | Et | Me | H | 0 | S | |
| 1070 | Et | Me | H | 1 | S | |
| 1071 | Et | Me | H | 2 | S | |
| 1072 | Et | Me | H | 0 | SO | |
| 1073 | Et | Me | H | 1 | SO | |
| 1074 | Et | Me | H | 2 | SO | |
| 1075 | Et | Me | H | 0 | SO$_2$ | |
| 1076 | Et | Me | H | 1 | SO$_2$ | |
| 1077 | Et | Me | H | 2 | SO$_2$ | |
| 1078 | Et | Me | H | 0 | NMe | |
| 1079 | Et | Me | H | 1 | NMe | |
| 1080 | Et | Me | H | 2 | NMe | |

TABLE 4

Inventive compounds of the general formula (I) in which Q is Q1, R$^5$ is hydrogen and n is 1

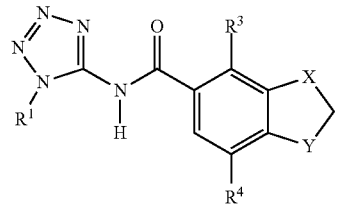

| No. | R$^1$ | R$^3$ | R$^4$ | Y | X | 1H NMR |
|---|---|---|---|---|---|---|
| 1081. | Me | Me | Me | S | CH$_2$ | |
| 1082. | Me | Me | Me | SO | CH$_2$ | |
| 1083. | Me | Me | Me | SO$_2$ | CH$_2$ | |
| 1084. | Me | Me | Me | S | CHMe | |
| 1085. | Me | Me | Me | SO | CHMe | |
| 1086. | Me | Me | Me | SO$_2$ | CHMe | |
| 1087. | Me | Me | Me | S | C(CH$_3$)$_2$ | |
| 1088. | Me | Me | Me | SO | C(CH$_3$)$_2$ | |
| 1089. | Me | Me | Me | SO$_2$ | C(CH$_3$)$_2$ | |
| 1090. | Me | Me | Me | S | C(OC$_2$H$_4$O) | |
| 1091. | Me | Me | Me | SO | C(OC$_2$H$_4$O) | |
| 1092. | Me | Me | Me | SO$_2$ | C(OC$_2$H$_4$O) | |
| 1093. | Me | Me | Me | S | C(SC$_2$H$_4$S) | |
| 1094. | Me | Me | Me | SO | C(SC$_2$H$_4$S) | |
| 1095. | Me | Me | Me | SO$_2$ | C(SC$_2$H$_4$S) | |
| 1096. | Me | Me | Me | S | CHOMe | |
| 1097. | Me | Me | Me | SO | CHOMe | |
| 1098. | Me | Me | Me | SO$_2$ | CHOMe | |
| 1099. | Me | Me | Me | S | CHOEt | |
| 1100. | Me | Me | Me | SO | CHOEt | |
| 1101. | Me | Me | Me | SO$_2$ | CHOEt | |
| 1102. | Me | Me | Me | S | CHOiPr | |
| 1103. | Me | Me | Me | SO | CHOiPr | |
| 1104. | Me | Me | Me | SO$_2$ | CHOiPr | |
| 1105. | Me | Me | Me | S | CHOCH$_2$cPr | |
| 1106. | Me | Me | Me | SO | CHOCH$_2$cPr | |
| 1107. | Me | Me | Me | SO$_2$ | CHOCH$_2$cPr | |
| 1108. | Me | Me | Me | S | CHOC$_2$H$_4$OMe | |
| 1109. | Me | Me | Me | SO | CHOC$_2$H$_4$OMe | |
| 1110. | Me | Me | Me | SO$_2$ | CHOC$_2$H$_4$OMe | |
| 1111. | Me | Me | Me | S | CHOCH$_2$CCH | |
| 1112. | Me | Me | Me | SO | CHOCH$_2$CCH | |
| 1113. | Me | Me | Me | SO$_2$ | CHOCH$_2$CCH | |
| 1114. | Me | Me | Me | S | CHOCH$_2$CH=CH$_2$ | |
| 1115. | Me | Me | Me | SO | CHOCH$_2$CH=CH$_2$ | |
| 1116. | Me | Me | Me | SO$_2$ | CHOCH$_2$CH=CH$_2$ | |
| 1117. | Me | Me | Me | S | (4,6-dimethoxypyrimidin-2-yloxy)CH | |
| 1118. | Me | Me | Me | SO | (4,6-dimethoxypyrimidin-2-yloxy)CH | |
| 1119. | Me | Me | Me | SO$_2$ | (4,6-dimethoxypyrimidin-2-yloxy)CH | |

TABLE 4-continued

Inventive compounds of the general formula (I) in which Q is Q1, R⁵ is hydrogen and n is 1

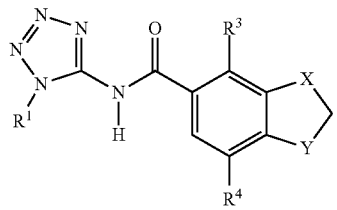

| No. | R¹ | R³ | R⁴ | Y | X | 1H NMR |
|---|---|---|---|---|---|---|
| 1120. | Me | Me | Me | S | 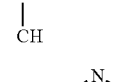 | |
| 1121. | Me | Me | Me | SO | 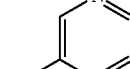 | |
| 1122. | Me | Me | Me | SO₂ | 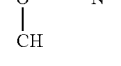 | |
| 1123. | Me | Me | Me | S | 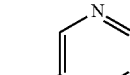 | |
| 1124. | Me | Me | Me | SO | 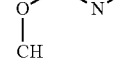 | |
| 1125. | Me | Me | Me | SO₂ | 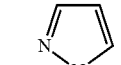 | |
| 1126. | Me | Me | Me | S |  | |
| 1127. | Me | Me | Me | SO | 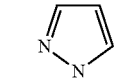 | |
| 1128. | Me | Me | Me | SO₂ |  | |

TABLE 4-continued

Inventive compounds of the general formula (I) in which Q is Q1, R⁵ is hydrogen and n is 1

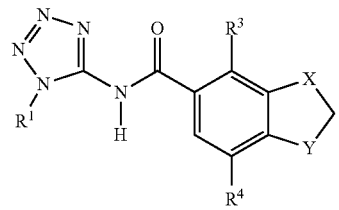

| No. | R¹ | R³ | R⁴ | Y | X | 1H NMR |
|---|---|---|---|---|---|---|
| 1129. | Me | Me | Me | S | 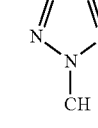 | |
| 1130. | Me | Me | Me | SO | 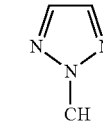 | |
| 1131. | Me | Me | Me | SO₂ | 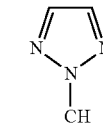 | |
| 1132. | Me | Me | Me | S | CHOC₂H₄F | |
| 1133. | Me | Me | Me | SO | CHOC₂H₄F | |
| 1134. | Me | Me | Me | SO₂ | CHOC₂H₄F | |
| 1135. | Me | Me | Me | S | C=NOMe | |
| 1136. | Me | Me | Me | SO | C=NOMe | |
| 1137. | Me | Me | Me | SO₂ | C=NOMe | |
| 1138. | Me | Me | Me | S | C=NOCH₂CCH | |
| 1139. | Me | Me | Me | SO | C=NOCH₂CCH | |
| 1140. | Me | Me | Me | SO₂ | C=NOCH₂CCH | |
| 1141. | Me | Me | Me | S | C=NOCH₂CH=CH₂ | |
| 1142. | Me | Me | Me | SO | C=NOCH₂CH=CH₂ | |
| 1143. | Me | Me | Me | SO₂ | C=NOCH₂CH=CH₂ | |
| 1144. | Me | Me | Me | S | C=O | |
| 1145. | Me | Me | Me | SO | C=O | |
| 1146. | Me | Me | Me | SO₂ | C=O | |
| 1147. | Me | Me | Me | S | C=S | |
| 1148. | Me | Me | Me | SO | C=S | |
| 1149. | Me | Me | Me | SO₂ | C=S | |
| 1150. | Me | Me | Me | S | C=S | |
| 1151. | Me | Me | Me | SO | C=S | |
| 1152. | Me | Me | Me | SO₂ | C=S | |
| 1153. | Me | Me | Me | S | C=N—N(CH₃)₂ | |
| 1154. | Me | Me | Me | SO | C=N—N(CH₃)₂ | |
| 1155. | Me | Me | Me | SO₂ | C=N—N(CH₃)₂ | |
| 1156. | Me | Me | Me | S | O | |
| 1157. | Me | Me | Me | SO | O | |
| 1158. | Me | Me | Me | SO₂ | O | |
| 1159. | Me | Me | Me | S | S | |
| 1160. | Me | Me | Me | SO | S | |
| 1161. | Me | Me | Me | SO₂ | S | |
| 1162. | Me | Me | Me | S | SO | |
| 1163. | Me | Me | Me | SO | SO | |
| 1164. | Me | Me | Me | SO₂ | SO | |
| 1165. | Me | Me | Me | S | SO₂ | |
| 1166. | Me | Me | Me | SO | SO₂ | |
| 1167. | Me | Me | Me | SO₂ | SO₂ | |
| 1168. | Me | Me | Me | S | NMe | |
| 1169. | Me | Me | Me | SO | NMe | |
| 1170. | Me | Me | Me | SO₂ | NMe | |
| 1171. | Me | Me | Me | O | O | |

TABLE 4-continued

Inventive compounds of the general formula (I) in which Q is Q1, $R^5$ is hydrogen and n is 1

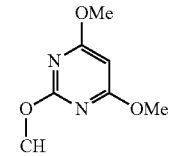

| No. | $R^1$ | $R^3$ | $R^4$ | Y | X | 1H NMR |
|---|---|---|---|---|---|---|
| 1172. | Me | Me | H | O | O | DMSO-d6, 400 MHz: 11.33 (s, 1H), 7.34 (d, 1H), 6.92 (d, 1H), 6.12 (s, 2H), 3.93 (s, 3H), 2.30 (s, 3H) |
| 1173. | Me | SMe | H | O | O | DMSO-d6, 400 MHz: 11.50 (bs, 1H), 7.21 (d, 1H), 6.99 (d, 1H), 6.18 (s, 2H), 3.96 (s, 3H), 2.44 (s, 3H) |
| 1174. | Me | Cl | H | O | O | |
| 1175. | Me | Cl | H | S | $CH_2$ | |
| 1176. | Me | Cl | H | SO | $CH_2$ | |
| 1177. | Me | Cl | H | $SO_2$ | $CH_2$ | DMSO, 400 MHz: 3.41 (t, 2H), 3.76 (t, 2H), 4.02 (s, 3H), 7.94 (s, 2H), 11.95 (s, 1H) |
| 1178. | Me | Cl | H | S | CHMe | |
| 1179. | Me | Cl | H | SO | CHMe | |
| 1180. | Me | Cl | H | $SO_2$ | CHMe | |
| 1181. | Me | Cl | H | S | $C(CH_3)_2$ | |
| 1182. | Me | Cl | H | SO | $C(CH_3)_2$ | |
| 1183. | Me | Cl | H | $SO_2$ | $C(CH_3)_2$ | |
| 1184. | Me | Cl | H | S | $C(OC_2H_4O)$ | |
| 1185. | Me | Cl | H | SO | $C(OC_2H_4O)$ | |
| 1186. | Me | Cl | H | $SO_2$ | $C(OC_2H_4O)$ | |
| 1187. | Me | Cl | H | S | $C(SC_2H_4S)$ | |
| 1188. | Me | Cl | H | SO | $C(SC_2H_4S)$ | |
| 1189. | Me | Cl | H | $SO_2$ | $C(SC_2H_4S)$ | |
| 1190. | Me | Cl | H | S | CHOMe | |
| 1191. | Me | Cl | H | SO | CHOMe | |
| 1192. | Me | Cl | H | $SO_2$ | CHOMe | CDCl3, 400 MHz: 3.57 (s, 3H), 3.68 (dd, 1H), 3.81 (d, 1H), 4.13 (s, 3H), 5.25 (d, 1H), 7.80 (d, 1H), 7.98 (d, 1H), 9.85 (s, 1H) |
| 1193. | Me | Cl | H | S | CHOEt | |
| 1194. | Me | Cl | H | SO | CHOEt | |
| 1195. | Me | Cl | H | $SO_2$ | CHOEt | |
| 1196. | Me | Cl | H | S | CHOiPr | |
| 1197. | Me | Cl | H | SO | CHOiPr | |
| 1198. | Me | Cl | H | $SO_2$ | CHOiPr | |
| 1199. | Me | Cl | H | S | $CHOCH_2cPr$ | |
| 1200. | Me | Cl | H | SO | $CHOCH_2cPr$ | |
| 1201. | Me | Cl | H | $SO_2$ | $CHOCH_2cPr$ | |
| 1202. | Me | Cl | H | S | $CHOC_2H_4OMe$ | |
| 1203. | Me | Cl | H | SO | $CHOC_2H_4OMe$ | |
| 1204. | Me | Cl | H | $SO_2$ | $CHOC_2H_4OMe$ | |
| 1205. | Me | Cl | H | S | $CHOCH_2CCH$ | |
| 1206. | Me | Cl | H | SO | $CHOCH_2CCH$ | |
| 1207. | Me | Cl | H | $SO_2$ | $CHOCH_2CCH$ | |
| 1208. | Me | Cl | H | S | $CHOCH_2CH=CH_2$ | |
| 1209. | Me | Cl | H | SO | $CHOCH_2CH=CH_2$ | |
| 1210. | Me | Cl | H | $SO_2$ | $CHOCH_2CH=CH_2$ | |
| 1211. | Me | Cl | H | S | 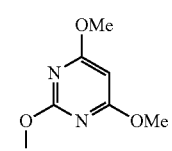 | |
| 1212. | Me | Cl | H | SO | 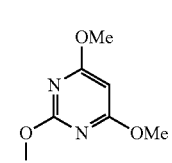 | |
| 1213. | Me | Cl | H | $SO_2$ | 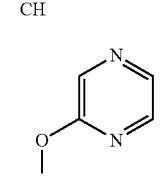 | |
| 1214. | Me | Cl | H | S | 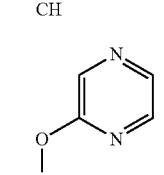 | |
| 1215. | Me | Cl | H | SO | 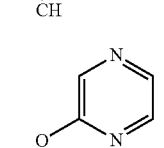 | |
| 1216. | Me | Cl | H | $SO_2$ | | |
| 1217. | Me | Cl | H | S | 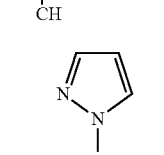 | |
| 1218. | Me | Cl | H | SO | 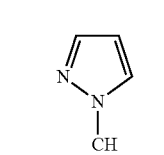 | |

TABLE 4-continued

Inventive compounds of the general formula (I) in which Q is Q1, $R^5$ is hydrogen and n is 1

| No. | $R^1$ | $R^3$ | $R^4$ | Y | X | 1H NMR |
|---|---|---|---|---|---|---|
| 1219. | Me | Cl | H | $SO_2$ | pyrazol-1-yl (CH) | |
| 1220. | Me | Cl | H | S | 1,2,3-triazol-1-yl (CH) | |
| 1221. | Me | Cl | H | SO | 1,2,3-triazol-1-yl (CH) | |
| 1222. | Me | Cl | H | $SO_2$ | 1,2,3-triazol-1-yl (CH) | |
| 1223. | Me | Cl | H | S | 2H-1,2,3-triazol-2-yl (CH) | |
| 1224. | Me | Cl | H | SO | 2H-1,2,3-triazol-2-yl (CH) | |
| 1225. | Me | Cl | H | $SO_2$ | 2H-1,2,3-triazol-2-yl (CH) | |
| 1226. | Me | Cl | H | S | $CHOC_2H_4F$ | |
| 1227. | Me | Cl | H | SO | $CHOC_2H_4F$ | |
| 1228. | Me | Cl | H | $SO_2$ | $CHOC_2H_4F$ | |
| 1229. | Me | Cl | H | S | C=NOMe | |
| 1230. | Me | Cl | H | SO | C=NOMe | |
| 1231. | Me | Cl | H | $SO_2$ | C=NOMe | |
| 1232. | Me | Cl | H | S | $C=NOCH_2CCH$ | |
| 1233. | Me | Cl | H | SO | $C=NOCH_2CCH$ | |
| 1234. | Me | Cl | H | $SO_2$ | $C=NOCH_2CCH$ | |
| 1235. | Me | Cl | H | S | $C=NOCH_2CH=CH_2$ | |
| 1236. | Me | Cl | H | SO | $C=NOCH_2CH=CH_2$ | |
| 1237. | Me | Cl | H | $SO_2$ | $C=NOCH_2CH=CH_2$ | |
| 1238. | Me | Cl | H | S | C=O | |
| 1239. | Me | Cl | H | SO | C=O | |
| 1240. | Me | Cl | H | $SO_2$ | C=O | |
| 1241. | Me | Cl | H | S | C=S | |
| 1242. | Me | Cl | H | SO | C=S | |
| 1243. | Me | Cl | H | $SO_2$ | C=S | |
| 1244. | Me | Cl | H | S | C=S | |
| 1245. | Me | Cl | H | SO | C=S | |
| 1246. | Me | Cl | H | $SO_2$ | C=S | |
| 1247. | Me | Cl | H | S | $C=N-N(CH_3)_2$ | |
| 1248. | Me | Cl | H | SO | $C=N-N(CH_3)_2$ | |
| 1249. | Me | Cl | H | $SO_2$ | $C=N-N(CH_3)_2$ | |
| 1250. | Me | Cl | H | S | O | |
| 1251. | Me | Cl | H | SO | O | |
| 1252. | Me | Cl | H | $SO_2$ | O | |
| 1253. | Me | Cl | H | S | S | |
| 1254. | Me | Cl | H | SO | S | |
| 1255. | Me | Cl | H | $SO_2$ | S | |
| 1256. | Me | Cl | H | S | SO | |
| 1257. | Me | Cl | H | SO | SO | |
| 1258. | Me | Cl | H | $SO_2$ | SO | |
| 1259. | Me | Cl | H | S | $SO_2$ | |
| 1260. | Me | Cl | H | SO | $SO_2$ | |
| 1261. | Me | Cl | H | $SO_2$ | $SO_2$ | |
| 1262. | Me | Cl | H | S | NMe | |
| 1263. | Me | Cl | H | SO | NMe | |
| 1264. | Me | Cl | H | $SO_2$ | NMe | |
| 1265. | Et | Me | Me | S | $CH_2$ | |
| 1266. | Et | Me | Me | SO | $CH_2$ | |
| 1267. | Et | Me | Me | $SO_2$ | $CH_2$ | |
| 1268. | Et | Me | Me | S | CHMe | |
| 1269. | Et | Me | Me | SO | CHMe | |
| 1270. | Et | Me | Me | $SO_2$ | CHMe | |
| 1271. | Et | Me | Me | S | $C(CH_3)_2$ | |
| 1272. | Et | Me | Me | SO | $C(CH_3)_2$ | |
| 1273. | Et | Me | Me | $SO_2$ | $C(CH_3)_2$ | |
| 1274. | Et | Me | Me | S | $C(OC_2H_4O)$ | |
| 1275. | Et | Me | Me | SO | $C(OC_2H_4O)$ | |
| 1276. | Et | Me | Me | $SO_2$ | $C(OC_2H_4O)$ | |
| 1277. | Et | Me | Me | S | $C(SC_2H_4S)$ | |
| 1278. | Et | Me | Me | SO | $C(SC_2H_4S)$ | |
| 1279. | Et | Me | Me | $SO_2$ | $C(SC_2H_4S)$ | |
| 1280. | Et | Me | Me | S | CHOMe | |
| 1281. | Et | Me | Me | SO | CHOMe | |
| 1282. | Et | Me | Me | $SO_2$ | CHOMe | |
| 1283. | Et | Me | Me | S | CHOEt | |
| 1284. | Et | Me | Me | SO | CHOEt | |
| 1285. | Et | Me | Me | $SO_2$ | CHOEt | |
| 1286. | Et | Me | Me | S | CHOiPr | |
| 1287. | Et | Me | Me | SO | CHOiPr | |
| 1288. | Et | Me | Me | $SO_2$ | CHOiPr | |
| 1289. | Et | Me | Me | S | $CHOCH_2cPr$ | |
| 1290. | Et | Me | Me | SO | $CHOCH_2cPr$ | |
| 1291. | Et | Me | Me | $SO_2$ | $CHOCH_2cPr$ | |
| 1292. | Et | Me | Me | S | $CHOC_2H_4OMe$ | |
| 1293. | Et | Me | Me | SO | $CHOC_2H_4OMe$ | |
| 1294. | Et | Me | Me | $SO_2$ | $CHOC_2H_4OMe$ | |
| 1295. | Et | Me | Me | S | $CHOCH_2CCH$ | |
| 1296. | Et | Me | Me | SO | $CHOCH_2CCH$ | |
| 1297. | Et | Me | Me | $SO_2$ | $CHOCH_2CCH$ | |
| 1298. | Et | Me | Me | S | $CHOCH_2CH=CH_2$ | |
| 1299. | Et | Me | Me | SO | $CHOCH_2CH=CH_2$ | |
| 1300. | Et | Me | Me | $SO_2$ | $CHOCH_2CH=CH_2$ | |

TABLE 4-continued

Inventive compounds of the general formula (I) in which Q is Q1, R⁵ is hydrogen and n is 1

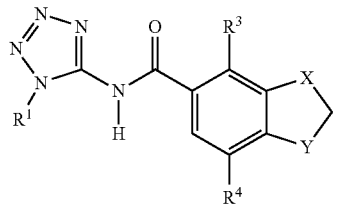

| No. | R¹ | R³ | R⁴ | Y | X | 1H NMR |
|---|---|---|---|---|---|---|
| 1301. | Et | Me | Me | S | 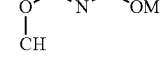 | |
| 1302. | Et | Me | Me | SO | 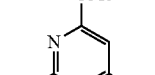 | |
| 1303. | Et | Me | Me | $SO_2$ | 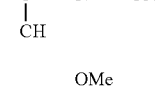 | |
| 1304. | Et | Me | Me | S | 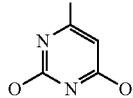 | |
| 1305. | Et | Me | Me | SO |  | |
| 1306. | Et | Me | Me | $SO_2$ | 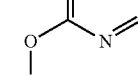 | |
| 1307. | Et | Me | Me | S |  | |
| 1308. | Et | Me | Me | SO |  | |

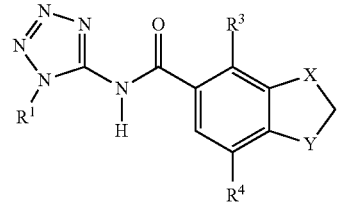

| No. | R¹ | R³ | R⁴ | Y | X | 1H NMR |
|---|---|---|---|---|---|---|
| 1309. | Et | Me | Me | $SO_2$ | 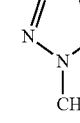 | |
| 1310. | Et | Me | Me | S | 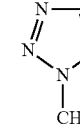 | |
| 1311. | Et | Me | Me | SO | 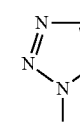 | |
| 1312. | Et | Me | Me | $SO_2$ | 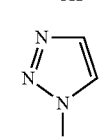 | |
| 1313. | Et | Me | Me | S | 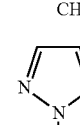 | |
| 1314. | Et | Me | Me | SO | 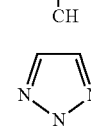 | |
| 1315. | Et | Me | Me | $SO_2$ | 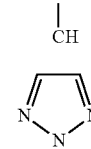 | |
| 1316. | Et | Me | Me | S | $CHOC_2H_4F$ | |
| 1317. | Et | Me | Me | SO | $CHOC_2H_4F$ | |
| 1318. | Et | Me | Me | $SO_2$ | $CHOC_2H_4F$ | |
| 1319. | Et | Me | Me | S | C=NOMe | |
| 1320. | Et | Me | Me | SO | C=NOMe | |
| 1321. | Et | Me | Me | $SO_2$ | C=NOMe | |
| 1322. | Et | Me | Me | S | $C=NOCH_2CCH$ | |
| 1323. | Et | Me | Me | SO | $C=NOCH_2CCH$ | |
| 1324. | Et | Me | Me | $SO_2$ | $C=NOCH_2CCH$ | |
| 1325. | Et | Me | Me | S | $C=NOCH_2CH=CH_2$ | |
| 1326. | Et | Me | Me | SO | $C=NOCH_2CH=CH_2$ | |
| 1327. | Et | Me | Me | $SO_2$ | $C=NOCH_2CH=CH_2$ | |
| 1328. | Et | Me | Me | S | C=O | |
| 1329. | Et | Me | Me | SO | C=O | |
| 1330. | Et | Me | Me | $SO_2$ | C=O | |

TABLE 4-continued

Inventive compounds of the general formula (I) in which Q is Q1, $R^5$ is hydrogen and n is 1

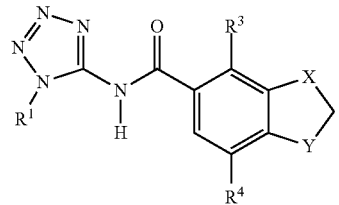

| No. | $R^1$ | $R^3$ | $R^4$ | Y | X | 1H NMR |
|---|---|---|---|---|---|---|
| 1331. | Et | Me | Me | S | C=S | |
| 1332. | Et | Me | Me | SO | C=S | |
| 1333. | Et | Me | Me | $SO_2$ | C=S | |
| 1334. | Et | Me | Me | S | C=S | |
| 1335. | Et | Me | Me | SO | C=S | |
| 1336. | Et | Me | Me | $SO_2$ | C=S | |
| 1337. | Et | Me | Me | S | C=N—N(CH_3)_2 | |
| 1338. | Et | Me | Me | SO | C=N—N(CH_3)_2 | |
| 1339. | Et | Me | Me | $SO_2$ | C=N—N(CH_3)_2 | |
| 1340. | Et | Me | Me | S | O | |
| 1341. | Et | Me | Me | SO | O | |
| 1342. | Et | Me | Me | $SO_2$ | O | |
| 1343. | Et | Me | Me | S | S | |
| 1344. | Et | Me | Me | SO | S | |
| 1345. | Et | Me | Me | $SO_2$ | S | |
| 1346. | Et | Me | Me | S | SO | |
| 1347. | Et | Me | Me | SO | SO | |
| 1348. | Et | Me | Me | $SO_2$ | SO | |
| 1349. | Et | Me | Me | S | $SO_2$ | |
| 1350. | Et | Me | Me | SO | $SO_2$ | |
| 1351. | Et | Me | Me | $SO_2$ | $SO_2$ | |
| 1352. | Et | Me | Me | S | NMe | |
| 1353. | Et | Me | Me | SO | NMe | |
| 1354. | Et | Me | Me | $SO_2$ | NMe | |
| 1355. | Et | Me | Me | O | O | |
| 1356. | Et | Me | H | O | O | CDCl3, 400 MHz: 9.65 (s, 1H), 7.42 (d, 1H), 6.79 (d, 1H), 6.06 (s, 2H), 4.43 (q, 2H), 2.41 (s, 3H), 1.60 (t, 3H) |
| 1357. | Et | SMe | H | O | O | |
| 1358. | Et | Cl | H | O | O | |
| 1359. | Et | Cl | H | S | $CH_2$ | |
| 1360. | Et | Cl | H | SO | $CH_2$ | |
| 1361. | Et | Cl | H | $SO_2$ | $CH_2$ | DMSO, 400 MHz: 1.48 (t, 3H), 3.42 (t, 2H), 3.75 (t, 2H), 4.38 (q, 2H), 7.93 (s, 2H), 11.86 (s, 1H) |
| 1362. | Et | Cl | H | S | CHMe | |
| 1363. | Et | Cl | H | SO | CHMe | |
| 1364. | Et | Cl | H | $SO_2$ | CHMe | |
| 1365. | Et | Cl | H | S | $C(CH_3)_2$ | |
| 1366. | Et | Cl | H | SO | $C(CH_3)_2$ | |
| 1367. | Et | Cl | H | $SO_2$ | $C(CH_3)_2$ | |
| 1368. | Et | Cl | H | S | $C(OC_2H_4O)$ | |
| 1369. | Et | Cl | H | SO | $C(OC_2H_4O)$ | |
| 1370. | Et | Cl | H | $SO_2$ | $C(OC_2H_4O)$ | |
| 1371. | Et | Cl | H | S | $C(SC_2H_4S)$ | |
| 1372. | Et | Cl | H | SO | $C(SC_2H_4S)$ | |
| 1373. | Et | Cl | H | $SO_2$ | $C(SC_2H_4S)$ | |
| 1374. | Et | Cl | H | S | CHOMe | |
| 1375. | Et | Cl | H | SO | CHOMe | |
| 1376. | Et | Cl | H | $SO_2$ | CHOMe | CDCl3, 400 MHz: 1.62 (t, 3H), 3.55 (s, 3H), 3.66 (dd, 1H), 3.81 (d, 1H), 4.47 (q, 2H), 5.23 (d, 1H), 7.75 (d, 1H), 7.94 (d, 1H), 10.6 (s, 1H) |
| 1377. | Et | Cl | H | S | CHOEt | |
| 1378. | Et | Cl | H | SO | CHOEt | |
| 1379. | Et | Cl | H | $SO_2$ | CHOEt | |
| 1380. | Et | Cl | H | S | CHOiPr | |
| 1381. | Et | Cl | H | SO | CHOiPr | |
| 1382. | Et | Cl | H | $SO_2$ | CHOiPr | |
| 1383. | Et | Cl | H | S | $CHOCH_2cPr$ | |
| 1384. | Et | Cl | H | SO | $CHOCH_2cPr$ | |
| 1385. | Et | Cl | H | $SO_2$ | $CHOCH_2cPr$ | |
| 1386. | Et | Cl | H | S | $CHOC_2H_4OMe$ | |
| 1387. | Et | Cl | H | SO | $CHOC_2H_4OMe$ | |
| 1388. | Et | Cl | H | $SO_2$ | $CHOC_2H_4OMe$ | |
| 1389. | Et | Cl | H | S | $CHOCH_2CCH$ | |
| 1390. | Et | Cl | H | SO | $CHOCH_2CCH$ | |
| 1391. | Et | Cl | H | $SO_2$ | $CHOCH_2CCH$ | |
| 1392. | Et | Cl | H | S | $CHOCH_2CH=CH_2$ | |
| 1393. | Et | Cl | H | SO | $CHOCH_2CH=CH_2$ | |
| 1394. | Et | Cl | H | $SO_2$ | $CHOCH_2CH=CH_2$ | |
| 1395. | Et | Cl | H | S | 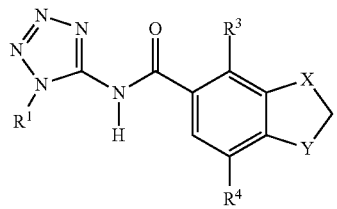 OMe pyrimidine-OCH | |
| 1396. | Et | Cl | H | SO | OMe pyrimidine-OCH | |
| 1397. | Et | Cl | H | $SO_2$ | OMe pyrimidine-OCH | |
| 1398. | Et | Cl | H | S | pyrazine-OCH | |
| 1399. | Et | Cl | H | SO | pyrazine-OCH | |

TABLE 4-continued

Inventive compounds of the general formula (I) in which Q is Q1, R⁵ is hydrogen and n is 1

[Structure: tetrazole-N(R¹)-C(=O)NH-benzene(R³,R⁴)-fused ring with X and Y]

| No. | R¹ | R³ | R⁴ | Y | X | 1H NMR |
|---|---|---|---|---|---|---|
| 1400. | Et | Cl | H | SO₂ | CH-O-pyrazine (3-oxypyrazinyl via CH) | |
| 1401. | Et | Cl | H | S | CH-(1-pyrazolyl) | |
| 1402. | Et | Cl | H | SO | CH-(1-pyrazolyl) | |
| 1403. | Et | Cl | H | SO₂ | CH-(1-pyrazolyl) | |
| 1404. | Et | Cl | H | S | CH-(1-(1,2,3-triazolyl)) | |
| 1405. | Et | Cl | H | SO | CH-(1-(1,2,3-triazolyl)) | |
| 1406. | Et | Cl | H | SO₂ | CH-(1-(1,2,3-triazolyl)) | |
| 1407. | Et | Cl | H | S | CH-(2-(1,2,3-triazolyl)) | |
| 1408. | Et | Cl | H | SO | CH-(2-(1,2,3-triazolyl)) | |
| 1409. | Et | Cl | H | SO₂ | CH-(2-(1,2,3-triazolyl)) | |
| 1410. | Et | Cl | H | S | CHOC₂H₄F | |
| 1411. | Et | Cl | H | SO | CHOC₂H₄F | |
| 1412. | Et | Cl | H | SO₂ | CHOC₂H₄F | |
| 1413. | Et | Cl | H | S | C=NOMe | |
| 1414. | Et | Cl | H | SO | C=NOMe | |
| 1415. | Et | Cl | H | SO₂ | C=NOMe | |
| 1416. | Et | Cl | H | S | C=NOCH₂CCH | |
| 1417. | Et | Cl | H | SO | C=NOCH₂CCH | |
| 1418. | Et | Cl | H | SO₂ | C=NOCH₂CCH | |
| 1419. | Et | Cl | H | S | C=NOCH₂CH=CH₂ | |
| 1420. | Et | Cl | H | SO | C=NOCH₂CH=CH₂ | |
| 1421. | Et | Cl | H | SO₂ | C=NOCH₂CH=CH₂ | |
| 1422. | Et | Cl | H | S | C=O | |
| 1423. | Et | Cl | H | SO | C=O | |
| 1424. | Et | Cl | H | SO₂ | C=O | |
| 1425. | Et | Cl | H | S | C=S | |
| 1426. | Et | Cl | H | SO | C=S | |
| 1427. | Et | Cl | H | SO₂ | C=S | |
| 1428. | Et | Cl | H | S | C=S | |
| 1429. | Et | Cl | H | SO | C=S | |
| 1430. | Et | Cl | H | SO₂ | C=S | |
| 1431. | Et | Cl | H | S | C=N—N(CH₃)₂ | |
| 1432. | Et | Cl | H | SO | C=N—N(CH₃)₂ | |
| 1433. | Et | Cl | H | SO₂ | C=N—N(CH₃)₂ | |
| 1434. | Et | Cl | H | S | O | |
| 1435. | Et | Cl | H | SO | O | |
| 1436. | Et | Cl | H | SO₂ | O | |
| 1437. | Et | Cl | H | S | S | |
| 1438. | Et | Cl | H | SO | S | |
| 1439. | Et | Cl | H | SO₂ | S | |
| 1440. | Et | Cl | H | S | SO | |
| 1441. | Et | Cl | H | SO | SO | |
| 1442. | Et | Cl | H | SO₂ | SO | |
| 1443. | Et | Cl | H | S | SO₂ | |
| 1444. | Et | Cl | H | SO | SO₂ | |
| 1445. | Et | Cl | H | SO₂ | SO₂ | |
| 1446. | Et | Cl | H | S | NMe | |
| 1447. | Et | Cl | H | SO | NMe | |
| 1448. | Et | Cl | H | SO₂ | NMe | |

TABLE 5

Inventive compounds of the general formula (I) in which Q is Q2, R⁵ is hydrogen and n is 1

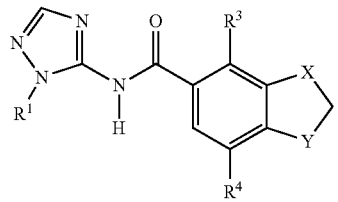

| No. | R¹ | R³ | R⁴ | Y | X | 1H NMR |
|---|---|---|---|---|---|---|
| 1449. | Me | Me | Me | S | $CH_2$ | |
| 1450. | Me | Me | Me | SO | $CH_2$ | |
| 1451. | Me | Me | Me | $SO_2$ | $CH_2$ | |
| 1452. | Me | Me | Me | S | CHMe | |
| 1453. | Me | Me | Me | SO | CHMe | |
| 1454. | Me | Me | Me | $SO_2$ | CHMe | |
| 1455. | Me | Me | Me | S | $C(CH_3)_2$ | |
| 1456. | Me | Me | Me | SO | $C(CH_3)_2$ | |
| 1457. | Me | Me | Me | $SO_2$ | $C(CH_3)_2$ | |
| 1458. | Me | Me | Me | S | $C(OC_2H_4O)$ | |
| 1459. | Me | Me | Me | SO | $C(OC_2H_4O)$ | |
| 1460. | Me | Me | Me | $SO_2$ | $C(OC_2H_4O)$ | |
| 1461. | Me | Me | Me | S | $C(SC_2H_4S)$ | |
| 1462. | Me | Me | Me | SO | $C(SC_2H_4S)$ | |
| 1463. | Me | Me | Me | $SO_2$ | $C(SC_2H_4S)$ | |
| 1464. | Me | Me | Me | S | CHOMe | |
| 1465. | Me | Me | Me | SO | CHOMe | |
| 1466. | Me | Me | Me | $SO_2$ | CHOMe | |
| 1467. | Me | Me | Me | S | CHOEt | |
| 1468. | Me | Me | Me | SO | CHOEt | |
| 1469. | Me | Me | Me | $SO_2$ | CHOEt | |
| 1470. | Me | Me | Me | S | CHOiPr | |
| 1471. | Me | Me | Me | SO | CHOiPr | |
| 1472. | Me | Me | Me | $SO_2$ | CHOiPr | |
| 1473. | Me | Me | Me | S | $CHOCH_2cPr$ | |
| 1474. | Me | Me | Me | SO | $CHOCH_2cPr$ | |
| 1475. | Me | Me | Me | $SO_2$ | $CHOCH_2cPr$ | |
| 1476. | Me | Me | Me | S | $CHOC_2H_4OMe$ | |
| 1477. | Me | Me | Me | SO | $CHOC_2H_4OMe$ | |
| 1478. | Me | Me | Me | $SO_2$ | $CHOC_2H_4OMe$ | |
| 1479. | Me | Me | Me | S | $CHOCH_2CCH$ | |
| 1480. | Me | Me | Me | SO | $CHOCH_2CCH$ | |
| 1481. | Me | Me | Me | $SO_2$ | $CHOCH_2CCH$ | |
| 1482. | Me | Me | Me | S | $CHOCH_2CH=CH_2$ | |
| 1483. | Me | Me | Me | SO | $CHOCH_2CH=CH_2$ | |
| 1484. | Me | Me | Me | $SO_2$ | $CHOCH_2CH=CH_2$ | |
| 1485. | Me | Me | Me | S | 2,6-di(OMe)pyrimidin-4-yloxy-CH | |
| 1486. | Me | Me | Me | SO | 2,6-di(OMe)pyrimidin-4-yloxy-CH | |
| 1487. | Me | Me | Me | $SO_2$ | 2,6-di(OMe)pyrimidin-4-yloxy-CH | |
| 1488. | Me | Me | Me | S | pyrazin-2-yloxy-CH | |
| 1489. | Me | Me | Me | SO | pyrazin-2-yloxy-CH | |
| 1490. | Me | Me | Me | $SO_2$ | pyrazin-2-yloxy-CH | |
| 1491. | Me | Me | Me | S | pyrazol-1-yl-CH | |
| 1492. | Me | Me | Me | SO | pyrazol-1-yl-CH | |
| 1493. | Me | Me | Me | $SO_2$ | pyrazol-1-yl-CH | |
| 1494. | Me | Me | Me | S | 1,2,3-triazol-1-yl-CH | |

TABLE 5-continued

Inventive compounds of the general formula (I) in which Q is Q2, $R^5$ is hydrogen and n is 1

| No. | $R^1$ | $R^3$ | $R^4$ | Y | X | 1H NMR |
|---|---|---|---|---|---|---|
| 1495. | Me | Me | Me | SO | N-N-N-CH (1-triazol-1-yl) | |
| 1496. | Me | Me | Me | $SO_2$ | N-N-N-CH (1-triazol-1-yl) | |
| 1497. | Me | Me | Me | S | N-N-N-CH (2-triazol-2-yl) | |
| 1498. | Me | Me | Me | SO | N-N-N-CH (2-triazol-2-yl) | |
| 1499. | Me | Me | Me | $SO_2$ | N-N-N-CH (2-triazol-2-yl) | |
| 1500. | Me | Me | Me | S | $CHOC_2H_4F$ | |
| 1501. | Me | Me | Me | SO | $CHOC_2H_4F$ | |
| 1502. | Me | Me | Me | $SO_2$ | $CHOC_2H_4F$ | |
| 1503. | Me | Me | Me | S | C=NOMe | |
| 1504. | Me | Me | Me | SO | C=NOMe | |
| 1505. | Me | Me | Me | $SO_2$ | C=NOMe | |
| 1506. | Me | Me | Me | S | $C=NOCH_2CCH$ | |
| 1507. | Me | Me | Me | SO | $C=NOCH_2CCH$ | |
| 1508. | Me | Me | Me | $SO_2$ | $C=NOCH_2CCH$ | |
| 1509. | Me | Me | Me | S | $C=NOCH_2CH=CH_2$ | |
| 1510. | Me | Me | Me | SO | $C=NOCH_2CH=CH_2$ | |
| 1511. | Me | Me | Me | $SO_2$ | $C=NOCH_2CH=CH_2$ | |
| 1512. | Me | Me | Me | S | C=O | |
| 1513. | Me | Me | Me | SO | C=O | |
| 1514. | Me | Me | Me | $SO_2$ | C=O | |
| 1515. | Me | Me | Me | S | C=S | |
| 1516. | Me | Me | Me | SO | C=S | |
| 1517. | Me | Me | Me | $SO_2$ | C=S | |
| 1518. | Me | Me | Me | S | C=S | |
| 1519. | Me | Me | Me | SO | C=S | |
| 1520. | Me | Me | Me | $SO_2$ | C=S | |
| 1521. | Me | Me | Me | S | $C=N-N(CH_3)_2$ | |
| 1522. | Me | Me | Me | SO | $C=N-N(CH_3)_2$ | |
| 1523. | Me | Me | Me | $SO_2$ | $C=N-N(CH_3)_2$ | |
| 1524. | Me | Me | Me | S | O | |
| 1525. | Me | Me | Me | SO | O | |
| 1526. | Me | Me | Me | $SO_2$ | O | |
| 1527. | Me | Me | Me | S | S | |
| 1528. | Me | Me | Me | SO | S | |
| 1529. | Me | Me | Me | $SO_2$ | S | |
| 1530. | Me | Me | Me | S | SO | |
| 1531. | Me | Me | Me | SO | SO | |
| 1532. | Me | Me | Me | $SO_2$ | SO | |
| 1533. | Me | Me | Me | S | $SO_2$ | |
| 1534. | Me | Me | Me | SO | $SO_2$ | |
| 1535. | Me | Me | Me | $SO_2$ | $SO_2$ | |
| 1536. | Me | Me | Me | S | NMe | |
| 1537. | Me | Me | Me | SO | NMe | |
| 1538. | Me | Me | Me | $SO_2$ | NMe | |
| 1539. | Me | Me | Me | O | O | |
| 1540. | Me | Me | H | O | O | |
| 1541. | Me | SMe | H | O | O | |
| 1542. | Me | Cl | H | O | O | |
| 1543. | Me | Cl | H | S | $CH_2$ | |
| 1544. | Me | Cl | H | SO | $CH_2$ | |
| 1545. | Me | Cl | H | $SO_2$ | $CH_2$ | DMSO, 400 MHz: 3.40 (t, 2H), 3.74 (t, 2H), 3.79 (s, 3H), 7.89 (br, 3H), 11.39 (s, 1H) |
| 1546. | Me | Cl | H | S | CHMe | |
| 1547. | Me | Cl | H | SO | CHMe | |
| 1548. | Me | Cl | H | $SO_2$ | CHMe | |
| 1549. | Me | Cl | H | S | $C(CH_3)_2$ | |
| 1550. | Me | Cl | H | SO | $C(CH_3)_2$ | |
| 1551. | Me | Cl | H | $SO_2$ | $C(CH_3)_2$ | |
| 1552. | Me | Cl | H | S | $C(OC_2H_4O)$ | |
| 1553. | Me | Cl | H | SO | $C(OC_2H_4O)$ | |
| 1554. | Me | Cl | H | $SO_2$ | $C(OC_2H_4O)$ | |
| 1555. | Me | Cl | H | S | $C(SC_2H_4S)$ | |
| 1556. | Me | Cl | H | SO | $C(SC_2H_4S)$ | |
| 1557. | Me | Cl | H | $SO_2$ | $C(SC_2H_4S)$ | |
| 1558. | Me | Cl | H | S | CHOMe | |
| 1559. | Me | Cl | H | SO | CHOMe | |
| 1560. | Me | Cl | H | $SO_2$ | CHOMe | CDCl3, 400 MHz: 3.56 (s, 3H), 3.68 (dd, 1H), 3.71 (d, 1H), 3.87 (s, 3H), 5.21 (d, 1H), 7.64 (s, 1H), 7.73 (d, 1H), 7.91 (d, 1H), 9.85 (s, 1H) |
| 1561. | Me | Cl | H | S | CHOEt | |
| 1562. | Me | Cl | H | SO | CHOEt | |
| 1563. | Me | Cl | H | $SO_2$ | CHOEt | |
| 1564. | Me | Cl | H | S | CHOiPr | |
| 1565. | Me | Cl | H | SO | CHOiPr | |
| 1566. | Me | Cl | H | $SO_2$ | CHOiPr | |
| 1567. | Me | Cl | H | S | $CHOCH_2cPr$ | |
| 1568. | Me | Cl | H | SO | $CHOCH_2cPr$ | |
| 1569. | Me | Cl | H | $SO_2$ | $CHOCH_2cPr$ | |
| 1570. | Me | Cl | H | S | $CHOC_2H_4OMe$ | |
| 1571. | Me | Cl | H | SO | $CHOC_2H_4OMe$ | |
| 1572. | Me | Cl | H | $SO_2$ | $CHOC_2H_4OMe$ | |
| 1573. | Me | Cl | H | S | $CHOCH_2CCH$ | |
| 1574. | Me | Cl | H | SO | $CHOCH_2CCH$ | |
| 1575. | Me | Cl | H | $SO_2$ | $CHOCH_2CCH$ | |
| 1576. | Me | Cl | H | S | $CHOCH_2CH=CH_2$ | |
| 1577. | Me | Cl | H | SO | $CHOCH_2CH=CH_2$ | |

TABLE 5-continued

Inventive compounds of the general formula (I) in which Q is Q2, $R^5$ is hydrogen and n is 1

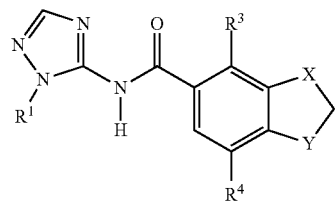

| No. | $R^1$ | $R^3$ | $R^4$ | Y | X | 1H NMR |
|---|---|---|---|---|---|---|
| 1578. | Me | Cl | H | $SO_2$ | CHOCH$_2$CH=CH$_2$ | |
| 1579. | Me | Cl | H | S | 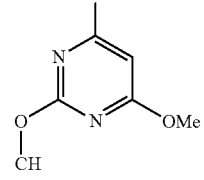 | |
| 1580. | Me | Cl | H | SO | 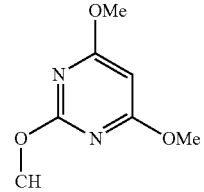 | |
| 1581. | Me | Cl | H | $SO_2$ | 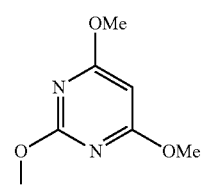 | |
| 1582. | Me | Cl | H | S | 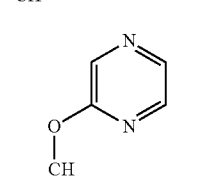 | |
| 1583. | Me | Cl | H | SO | 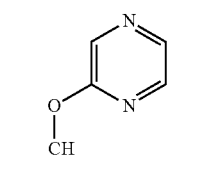 | |
| 1584. | Me | Cl | H | $SO_2$ | 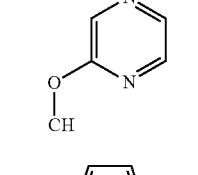 | |
| 1585. | Me | Cl | H | S | 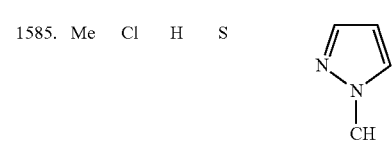 | |

TABLE 5-continued

Inventive compounds of the general formula (I) in which Q is Q2, $R^5$ is hydrogen and n is 1

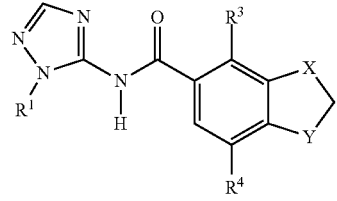

| No. | $R^1$ | $R^3$ | $R^4$ | Y | X | 1H NMR |
|---|---|---|---|---|---|---|
| 1586. | Me | Cl | H | SO | 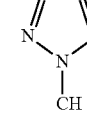 | |
| 1587. | Me | Cl | H | $SO_2$ | 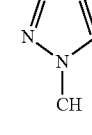 | |
| 1588. | Me | Cl | H | S | 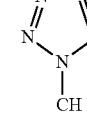 | |
| 1589. | Me | Cl | H | SO | 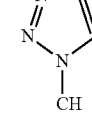 | |
| 1590. | Me | Cl | H | $SO_2$ | 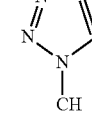 | |
| 1591. | Me | Cl | H | S | 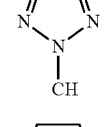 | |
| 1592. | Me | Cl | H | SO | 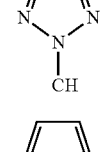 | |
| 1593. | Me | Cl | H | $SO_2$ | 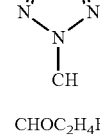 | |
| 1594. | Me | Cl | H | S | CHOC$_2$H$_4$F | |
| 1595. | Me | Cl | H | SO | CHOC$_2$H$_4$F | |
| 1596. | Me | Cl | H | $SO_2$ | CHOC$_2$H$_4$F | |
| 1597. | Me | Cl | H | S | C=NOMe | |
| 1598. | Me | Cl | H | SO | C=NOMe | |
| 1599. | Me | Cl | H | $SO_2$ | C=NOMe | |
| 1600. | Me | Cl | H | S | C=NOCH$_2$CCH | |
| 1601. | Me | Cl | H | SO | C=NOCH$_2$CCH | |
| 1602. | Me | Cl | H | $SO_2$ | C=NOCH$_2$CCH | |
| 1603. | Me | Cl | H | S | C=NOCH$_2$CH=CH$_2$ | |

TABLE 5-continued

Inventive compounds of the general formula (I) in which Q is Q2, $R^5$ is hydrogen and n is 1

| No. | $R^1$ | $R^3$ | $R^4$ | Y | X | 1H NMR |
|---|---|---|---|---|---|---|
| 1604. | Me | Cl | H | SO | C=NOCH$_2$CH=CH$_2$ | |
| 1605. | Me | Cl | H | SO$_2$ | C=NOCH$_2$CH=CH$_2$ | |
| 1606. | Me | Cl | H | S | C=O | |
| 1607. | Me | Cl | H | SO | C=O | |
| 1608. | Me | Cl | H | SO$_2$ | C=O | |
| 1609. | Me | Cl | H | S | C=S | |
| 1610. | Me | Cl | H | SO | C=S | |
| 1611. | Me | Cl | H | SO$_2$ | C=S | |
| 1612. | Me | Cl | H | S | C=S | |
| 1613. | Me | Cl | H | SO | C=S | |
| 1614. | Me | Cl | H | SO$_2$ | C=S | |
| 1615. | Me | Cl | H | S | C=N—N(CH$_3$)$_2$ | |
| 1616. | Me | Cl | H | SO | C=N—N(CH$_3$)$_2$ | |
| 1617. | Me | Cl | H | SO$_2$ | C=N—N(CH$_3$)$_2$ | |
| 1618. | Me | Cl | H | S | O | |
| 1619. | Me | Cl | H | SO | O | |
| 1620. | Me | Cl | H | SO$_2$ | O | |
| 1621. | Me | Cl | H | S | S | |
| 1622. | Me | Cl | H | SO | S | |
| 1623. | Me | Cl | H | SO$_2$ | S | |
| 1624. | Me | Cl | H | S | SO | |
| 1625. | Me | Cl | H | SO | SO | |
| 1626. | Me | Cl | H | SO$_2$ | SO | |
| 1627. | Me | Cl | H | S | SO$_2$ | |
| 1628. | Me | Cl | H | SO | SO$_2$ | |
| 1629. | Me | Cl | H | SO$_2$ | SO$_2$ | |
| 1630. | Me | Cl | H | S | NMe | |
| 1631. | Me | Cl | H | SO | NMe | |
| 1632. | Me | Cl | H | SO$_2$ | NMe | |
| 1633. | Et | Me | Me | S | CH$_2$ | |
| 1634. | Et | Me | Me | SO | CH$_2$ | |
| 1635. | Et | Me | Me | SO$_2$ | CH$_2$ | |
| 1636. | Et | Me | Me | S | CHMe | |
| 1637. | Et | Me | Me | SO | CHMe | |
| 1638. | Et | Me | Me | SO$_2$ | CHMe | |
| 1639. | Et | Me | Me | S | C(CH$_3$)$_2$ | |
| 1640. | Et | Me | Me | SO | C(CH$_3$)$_2$ | |
| 1641. | Et | Me | Me | SO$_2$ | C(CH$_3$)$_2$ | |
| 1642. | Et | Me | Me | S | C(OC$_2$H$_4$O) | |
| 1643. | Et | Me | Me | SO | C(OC$_2$H$_4$O) | |
| 1644. | Et | Me | Me | SO$_2$ | C(OC$_2$H$_4$O) | |
| 1645. | Et | Me | Me | S | C(SC$_2$H$_4$S) | |
| 1646. | Et | Me | Me | SO | C(SC$_2$H$_4$S) | |
| 1647. | Et | Me | Me | SO$_2$ | C(SC$_2$H$_4$S) | |
| 1648. | Et | Me | Me | S | CHOMe | |
| 1649. | Et | Me | Me | SO | CHOMe | |
| 1650. | Et | Me | Me | SO$_2$ | CHOMe | |
| 1651. | Et | Me | Me | S | CHOEt | |
| 1652. | Et | Me | Me | SO | CHOEt | |
| 1653. | Et | Me | Me | SO$_2$ | CHOEt | |
| 1654. | Et | Me | Me | S | CHOiPr | |
| 1655. | Et | Me | Me | SO | CHOiPr | |
| 1656. | Et | Me | Me | SO$_2$ | CHOiPr | |
| 1657. | Et | Me | Me | S | CHOCH$_2$cPr | |
| 1658. | Et | Me | Me | SO | CHOCH$_2$cPr | |
| 1659. | Et | Me | Me | SO$_2$ | CHOCH$_2$cPr | |
| 1660. | Et | Me | Me | S | CHOC$_2$H$_4$OMe | |
| 1661. | Et | Me | Me | SO | CHOC$_2$H$_4$OMe | |
| 1662. | Et | Me | Me | SO$_2$ | CHOC$_2$H$_4$OMe | |
| 1663. | Et | Me | Me | S | CHOCH$_2$CCH | |
| 1664. | Et | Me | Me | SO | CHOCH$_2$CCH | |
| 1665. | Et | Me | Me | SO$_2$ | CHOCH$_2$CCH | |
| 1666. | Et | Me | Me | S | CHOCH$_2$CH=CH$_2$ | |
| 1667. | Et | Me | Me | SO | CHOCH$_2$CH=CH$_2$ | |
| 1668. | Et | Me | Me | SO$_2$ | CHOCH$_2$CH=CH$_2$ | |
| 1669. | Et | Me | Me | S | (4,6-dimethoxypyrimidin-2-yloxy)CH | |
| 1670. | Et | Me | Me | SO | (4,6-dimethoxypyrimidin-2-yloxy)CH | |
| 1671. | Et | Me | Me | SO$_2$ | (4,6-dimethoxypyrimidin-2-yloxy)CH | |
| 1672. | Et | Me | Me | S | (pyrazin-2-yloxy)CH | |
| 1673. | Et | Me | Me | SO | (pyrazin-2-yloxy)CH | |
| 1674. | Et | Me | Me | SO$_2$ | (pyrazin-2-yloxy)CH | |
| 1675. | Et | Me | Me | S | (pyrazol-1-yl)CH | |

TABLE 5-continued

Inventive compounds of the general formula (I) in which Q is Q2, R⁵ is hydrogen and n is 1

[Structure: N-(1-R¹-1H-1,2,4-triazol-5-yl)benzamide with R³, R⁴ substituents and fused X-Y ring]

| No. | R¹ | R³ | R⁴ | Y | X | 1H NMR |
|---|---|---|---|---|---|---|
| 1676. | Et | Me | Me | SO | N-pyrazolyl-CH | |
| 1677. | Et | Me | Me | SO₂ | N-pyrazolyl-CH | |
| 1678. | Et | Me | Me | S | N-1,2,3-triazolyl-CH | |
| 1679. | Et | Me | Me | SO | N-1,2,3-triazolyl-CH | |
| 1680. | Et | Me | Me | SO₂ | N-1,2,3-triazolyl-CH | |
| 1681. | Et | Me | Me | S | N-1,2,3-triazolyl-CH | |
| 1682. | Et | Me | Me | SO | N-1,2,3-triazolyl-CH | |
| 1683. | Et | Me | Me | SO₂ | N-1,2,3-triazolyl-CH | |
| 1684. | Et | Me | Me | S | CHOC₂H₄F | |
| 1685. | Et | Me | Me | SO | CHOC₂H₄F | |
| 1686. | Et | Me | Me | SO₂ | CHOC₂H₄F | |
| 1687. | Et | Me | Me | S | C=NOMe | |
| 1688. | Et | Me | Me | SO | C=NOMe | |
| 1689. | Et | Me | Me | SO₂ | C=NOMe | |
| 1690. | Et | Me | Me | S | C=NOCH₂CCH | |
| 1691. | Et | Me | Me | SO | C=NOCH₂CCH | |
| 1692. | Et | Me | Me | SO₂ | C=NOCH₂CCH | |
| 1693. | Et | Me | Me | S | C=NOCH₂CH=CH₂ | |
| 1694. | Et | Me | Me | SO | C=NOCH₂CH=CH₂ | |
| 1695. | Et | Me | Me | SO₂ | C=NOCH₂CH=CH₂ | |
| 1696. | Et | Me | Me | S | C=O | |
| 1697. | Et | Me | Me | SO | C=O | |
| 1698. | Et | Me | Me | SO₂ | C=O | |
| 1699. | Et | Me | Me | S | C=S | |
| 1700. | Et | Me | Me | SO | C=S | |
| 1701. | Et | Me | Me | SO₂ | C=S | |
| 1702. | Et | Me | Me | S | C=S | |
| 1703. | Et | Me | Me | SO | C=S | |
| 1704. | Et | Me | Me | SO₂ | C=S | |
| 1705. | Et | Me | Me | S | C=N—N(CH₃)₂ | |
| 1706. | Et | Me | Me | SO | C=N—N(CH₃)₂ | |
| 1707. | Et | Me | Me | SO₂ | C=N—N(CH₃)₂ | |
| 1708. | Et | Me | Me | S | O | |
| 1709. | Et | Me | Me | SO | O | |
| 1710. | Et | Me | Me | SO₂ | O | |
| 1711. | Et | Me | Me | S | S | |
| 1712. | Et | Me | Me | SO | S | |
| 1713. | Et | Me | Me | SO₂ | S | |
| 1714. | Et | Me | Me | S | SO | |
| 1715. | Et | Me | Me | SO | SO | |
| 1716. | Et | Me | Me | SO₂ | SO | |
| 1717. | Et | Me | Me | S | SO₂ | |
| 1718. | Et | Me | Me | SO | SO₂ | |
| 1719. | Et | Me | Me | SO₂ | SO₂ | |
| 1720. | Et | Me | Me | S | NMe | |
| 1721. | Et | Me | Me | SO | NMe | |
| 1722. | Et | Me | Me | SO₂ | NMe | |
| 1723. | Et | Me | Me | O | O | |
| 1724. | Et | Me | H | O | O | |
| 1725. | Et | SMe | H | O | O | |
| 1726. | Et | Cl | H | O | O | |
| 1727. | Et | Cl | H | S | CH₂ | |
| 1728. | Et | Cl | H | SO | CH₂ | |
| 1729. | Et | Cl | H | SO₂ | CH₂ | |
| 1730. | Et | Cl | H | S | CHMe | |
| 1731. | Et | Cl | H | SO | CHMe | |
| 1732. | Et | Cl | H | SO₂ | CHMe | |
| 1733. | Et | Cl | H | S | C(CH₃)₂ | |
| 1734. | Et | Cl | H | SO | C(CH₃)₂ | |
| 1735. | Et | Cl | H | SO₂ | C(CH₃)₂ | |
| 1736. | Et | Cl | H | S | C(OC₂H₄O) | |
| 1737. | Et | Cl | H | SO | C(OC₂H₄O) | |
| 1738. | Et | Cl | H | SO₂ | C(OC₂H₄O) | |
| 1739. | Et | Cl | H | S | C(SC₂H₄S) | |
| 1740. | Et | Cl | H | SO | C(SC₂H₄S) | |
| 1741. | Et | Cl | H | SO₂ | C(SC₂H₄S) | |
| 1742. | Et | Cl | H | S | CHOMe | |
| 1743. | Et | Cl | H | SO | CHOMe | |
| 1744. | Et | Cl | H | SO₂ | CHOMe | |
| 1745. | Et | Cl | H | S | CHOEt | |
| 1746. | Et | Cl | H | SO | CHOEt | |
| 1747. | Et | Cl | H | SO₂ | CHOEt | |
| 1748. | Et | Cl | H | S | CHOiPr | |
| 1749. | Et | Cl | H | SO | CHOiPr | |
| 1750. | Et | Cl | H | SO₂ | CHOiPr | |
| 1751. | Et | Cl | H | S | CHOCH₂cPr | |
| 1752. | Et | Cl | H | SO | CHOCH₂cPr | |
| 1753. | Et | Cl | H | SO₂ | CHOCH₂cPr | |
| 1754. | Et | Cl | H | S | CHOC₂H₄OMe | |
| 1755. | Et | Cl | H | SO | CHOC₂H₄OMe | |
| 1756. | Et | Cl | H | SO₂ | CHOC₂H₄OMe | |
| 1757. | Et | Cl | H | S | CHOCH₂CCH | |

TABLE 5-continued

Inventive compounds of the general formula (I) in which Q is Q2, R⁵ is hydrogen and n is 1

| No. | R¹ | R³ | R⁴ | Y | X | 1H NMR |
|---|---|---|---|---|---|---|
| 1758. | Et | Cl | H | SO | CHOCH₂CCH | |
| 1759. | Et | Cl | H | SO₂ | CHOCH₂CCH | |
| 1760. | Et | Cl | H | S | CHOCH₂CH=CH₂ | |
| 1761. | Et | Cl | H | SO | CHOCH₂CH=CH₂ | |
| 1762. | Et | Cl | H | SO₂ | CHOCH₂CH=CH₂ | |
| 1763. | Et | Cl | H | S | CH-O-(2,6-dimethoxypyrimidin-4-yl) | |
| 1764. | Et | Cl | H | SO | CH-O-(2,6-dimethoxypyrimidin-4-yl) | |
| 1765. | Et | Cl | H | SO₂ | CH-O-(2,6-dimethoxypyrimidin-4-yl) | |
| 1766. | Et | Cl | H | S | CH-O-(pyrazin-2-yl) | |
| 1767. | Et | Cl | H | SO | CH-O-(pyrazin-2-yl) | |
| 1768. | Et | Cl | H | SO₂ | CH-O-(pyrazin-2-yl) | |
| 1769. | Et | Cl | H | S | CH-(pyrazol-1-yl) | |
| 1770. | Et | Cl | H | SO | CH-(pyrazol-1-yl) | |
| 1771. | Et | Cl | H | SO₂ | CH-(pyrazol-1-yl) | |
| 1772. | Et | Cl | H | S | CH-(1,2,3-triazol-1-yl) | |
| 1773. | Et | Cl | H | SO | CH-(1,2,3-triazol-1-yl) | |
| 1774. | Et | Cl | H | SO₂ | CH-(1,2,3-triazol-1-yl) | |
| 1775. | Et | Cl | H | S | CH-(1,2,3-triazol-2-yl) | |
| 1776. | Et | Cl | H | SO | CH-(1,2,3-triazol-2-yl) | |
| 1777. | Et | Cl | H | SO₂ | CH-(1,2,3-triazol-2-yl) | |
| 1778. | Et | Cl | H | S | CHOC₂H₄F | |
| 1779. | Et | Cl | H | SO | CHOC₂H₄F | |
| 1780. | Et | Cl | H | SO₂ | CHOC₂H₄F | |

TABLE 5-continued

Inventive compounds of the general formula (I) in which Q is Q2, R⁵ is hydrogen and n is 1

| No. | R¹ | R³ | R⁴ | Y | X | 1H NMR |
|---|---|---|---|---|---|---|
| 1781. | Et | Cl | H | S | C=NOMe | |
| 1782. | Et | Cl | H | SO | C=NOMe | |
| 1783. | Et | Cl | H | SO₂ | C=NOMe | |
| 1784. | Et | Cl | H | S | C=NOCH₂CCH | |
| 1785. | Et | Cl | H | SO | C=NOCH₂CCH | |
| 1786. | Et | Cl | H | SO₂ | C=NOCH₂CCH | |
| 1787. | Et | Cl | H | S | C=NOCH₂CH=CH₂ | |
| 1788. | Et | Cl | H | SO | C=NOCH₂CH=CH₂ | |
| 1789. | Et | Cl | H | SO₂ | C=NOCH₂CH=CH₂ | |
| 1790. | Et | Cl | H | S | C=O | |
| 1791. | Et | Cl | H | SO | C=O | |
| 1792. | Et | Cl | H | SO₂ | C=O | |
| 1793. | Et | Cl | H | S | C=S | |
| 1794. | Et | Cl | H | SO | C=S | |
| 1795. | Et | Cl | H | SO₂ | C=S | |
| 1796. | Et | Cl | H | S | C=S | |
| 1797. | Et | Cl | H | SO | C=S | |
| 1798. | Et | Cl | H | SO₂ | C=S | |
| 1799. | Et | Cl | H | S | C=N—N(CH₃)₂ | |
| 1800. | Et | Cl | H | SO | C=N—N(CH₃)₂ | |
| 1801. | Et | Cl | H | SO₂ | C=N—N(CH₃)₂ | |
| 1802. | Et | Cl | H | S | O | |
| 1803. | Et | Cl | H | SO | O | |
| 1804. | Et | Cl | H | SO₂ | O | |
| 1805. | Et | Cl | H | S | S | |
| 1806. | Et | Cl | H | SO | S | |
| 1807. | Et | Cl | H | SO₂ | S | |
| 1808. | Et | Cl | H | S | SO | |
| 1809. | Et | Cl | H | SO | SO | |
| 1810. | Et | Cl | H | SO₂ | SO | |
| 1811. | Et | Cl | H | S | SO₂ | |
| 1812. | Et | Cl | H | SO | SO₂ | |
| 1813. | Et | Cl | H | SO₂ | SO₂ | |
| 1814. | Et | Cl | H | S | NMe | |
| 1815. | Et | Cl | H | SO | NMe | |
| 1816. | Et | Cl | H | SO₂ | NMe | |

TABLE 6

Inventive compounds of the general formula (I) in which Q is Q3, R⁵ is hydrogen and n is 1

| No. | R² | R³ | R⁴ | Y | X | 1H NMR |
|---|---|---|---|---|---|---|
| 1817. | Me | Me | Me | S | CH₂ | |
| 1818. | Me | Me | Me | SO | CH₂ | |
| 1819. | Me | Me | Me | SO₂ | CH₂ | |
| 1820. | Me | Me | Me | S | CHMe | |
| 1821. | Me | Me | Me | SO | CHMe | |
| 1822. | Me | Me | Me | SO₂ | CHMe | |
| 1823. | Me | Me | Me | S | C(CH₃)₂ | |
| 1824. | Me | Me | Me | SO | C(CH₃)₂ | |
| 1825. | Me | Me | Me | SO₂ | C(CH₃)₂ | |
| 1826. | Me | Me | Me | S | C(OC₂H₄O) | |
| 1827. | Me | Me | Me | SO | C(OC₂H₄O) | |
| 1828. | Me | Me | Me | SO₂ | C(OC₂H₄O) | |
| 1829. | Me | Me | Me | S | C(SC₂H₄S) | |
| 1830. | Me | Me | Me | SO | C(SC₂H₄S) | |
| 1831. | Me | Me | Me | SO₂ | C(SC₂H₄S) | |
| 1832. | Me | Me | Me | S | CHOMe | |
| 1833. | Me | Me | Me | SO | CHOMe | |
| 1834. | Me | Me | Me | SO₂ | CHOMe | |
| 1835. | Me | Me | Me | S | CHOEt | |
| 1836. | Me | Me | Me | SO | CHOEt | |
| 1837. | Me | Me | Me | SO₂ | CHOEt | |
| 1838. | Me | Me | Me | S | CHOiPr | |
| 1839. | Me | Me | Me | SO | CHOiPr | |
| 1840. | Me | Me | Me | SO₂ | CHOiPr | |
| 1841. | Me | Me | Me | S | CHOCH₂cPr | |
| 1842. | Me | Me | Me | SO | CHOCH₂cPr | |
| 1843. | Me | Me | Me | SO₂ | CHOCH₂cPr | |
| 1844. | Me | Me | Me | S | CHOC₂H₄OMe | |
| 1845. | Me | Me | Me | SO | CHOC₂H₄OMe | |
| 1846. | Me | Me | Me | SO₂ | CHOC₂H₄OMe | |
| 1847. | Me | Me | Me | S | CHOCH₂CCH | |
| 1848. | Me | Me | Me | SO | CHOCH₂CCH | |
| 1849. | Me | Me | Me | SO₂ | CHOCH₂CCH | |
| 1850. | Me | Me | Me | S | CHOCH₂CH=CH₂ | |
| 1851. | Me | Me | Me | SO | CHOCH₂CH=CH₂ | |
| 1852. | Me | Me | Me | SO₂ | CHOCH₂CH=CH₂ | |
| 1853. | Me | Me | Me | S | pyrimidinyl-OMe₂-OCH | |
| 1854. | Me | Me | Me | SO | pyrimidinyl-OMe₂-OCH | |
| 1855. | Me | Me | Me | SO₂ | pyrimidinyl-OMe₂-OCH | |

TABLE 6-continued

Inventive compounds of the general formula (I) in which Q is Q3, R⁵ is hydrogen and n is 1

| No. | R² | R³ | R⁴ | Y | X | 1H NMR |
|---|---|---|---|---|---|---|
| 1856. | Me | Me | Me | S | 3-(pyrazin-2-yloxy)methyl | |
| 1857. | Me | Me | Me | SO | 3-(pyrazin-2-yloxy)methyl | |
| 1858. | Me | Me | Me | SO₂ | 3-(pyrazin-2-yloxy)methyl | |
| 1859. | Me | Me | Me | S | (pyrazol-1-yl)methyl | |
| 1860. | Me | Me | Me | SO | (pyrazol-1-yl)methyl | |
| 1861. | Me | Me | Me | SO₂ | (pyrazol-1-yl)methyl | |
| 1862. | Me | Me | Me | S | (1,2,3-triazol-1-yl)methyl | |
| 1863. | Me | Me | Me | SO | (1,2,3-triazol-1-yl)methyl | |
| 1864. | Me | Me | Me | SO₂ | (1,2,3-triazol-1-yl)methyl | |
| 1865. | Me | Me | Me | S | (1,2,3-triazol-2-yl)methyl | |
| 1866. | Me | Me | Me | SO | (1,2,3-triazol-2-yl)methyl | |
| 1867. | Me | Me | Me | SO₂ | (1,2,3-triazol-2-yl)methyl | |
| 1868. | Me | Me | Me | S | CHOC₂H₄F | |
| 1869. | Me | Me | Me | SO | CHOC₂H₄F | |
| 1870. | Me | Me | Me | SO₂ | CHOC₂H₄F | |
| 1871. | Me | Me | Me | S | C=NOMe | |
| 1872. | Me | Me | Me | SO | C=NOMe | |
| 1873. | Me | Me | Me | SO₂ | C=NOMe | |
| 1874. | Me | Me | Me | S | C=NOCH₂CCH | |
| 1875. | Me | Me | Me | SO | C=NOCH₂CCH | |
| 1876. | Me | Me | Me | SO₂ | C=NOCH₂CCH | |
| 1877. | Me | Me | Me | S | C=NOCH₂CH=CH₂ | |
| 1878. | Me | Me | Me | SO | C=NOCH₂CH=CH₂ | |
| 1879. | Me | Me | Me | SO₂ | C=NOCH₂CH=CH₂ | |
| 1880. | Me | Me | Me | S | C=O | |
| 1881. | Me | Me | Me | SO | C=O | |
| 1882. | Me | Me | Me | SO₂ | C=O | |
| 1883. | Me | Me | Me | S | C=S | |
| 1884. | Me | Me | Me | SO | C=S | |
| 1885. | Me | Me | Me | SO₂ | C=S | |
| 1886. | Me | Me | Me | S | C=S | |
| 1887. | Me | Me | Me | SO | C=S | |
| 1888. | Me | Me | Me | SO₂ | C=S | |
| 1889. | Me | Me | Me | S | C=N—N(CH₃)₂ | |
| 1890. | Me | Me | Me | SO | C=N—N(CH₃)₂ | |
| 1891. | Me | Me | Me | SO₂ | C=N—N(CH₃)₂ | |
| 1892. | Me | Me | Me | S | O | |
| 1893. | Me | Me | Me | SO | O | |
| 1894. | Me | Me | Me | SO₂ | O | |
| 1895. | Me | Me | Me | S | S | |
| 1896. | Me | Me | Me | SO | S | |
| 1897. | Me | Me | Me | SO₂ | S | |
| 1898. | Me | Me | Me | S | SO | |
| 1899. | Me | Me | Me | SO | SO | |
| 1900. | Me | Me | Me | SO₂ | SO | |
| 1901. | Me | Me | Me | S | SO₂ | |
| 1902. | Me | Me | Me | SO | SO₂ | |
| 1903. | Me | Me | Me | SO₂ | SO₂ | |
| 1904. | Me | Me | Me | S | NMe | |
| 1905. | Me | Me | Me | SO | NMe | |
| 1906. | Me | Me | Me | SO₂ | NMe | |
| 1907. | Me | Me | Me | O | O | |
| 1908. | Me | Me | H | O | O | |
| 1909. | Me | SMe | H | O | O | |
| 1910. | Me | Cl | H | O | O | |

TABLE 6-continued

Inventive compounds of the general formula (I) in which Q is Q3, $R^5$ is hydrogen and n is 1

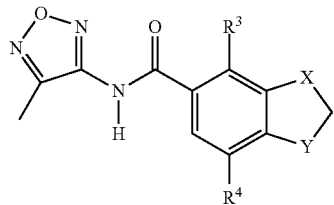

| No. | $R^2$ | $R^3$ | $R^4$ | Y | X | 1H NMR |
|---|---|---|---|---|---|---|
| 1911. | Me | Cl | H | S | $CH_2$ | |
| 1912. | Me | Cl | H | SO | $CH_2$ | |
| 1913. | Me | Cl | H | $SO_2$ | $CH_2$ | CDCl3, 400 MHz: 2.52 (s, 3H), 3.47 (t, 2H), 3.62 (t, 2H), 3.79 (s, 3H), 7.80 (d, 1H), 7.88 (d, 1H), 8.14 (s, 1H) |
| 1914. | Me | Cl | H | S | CHMe | |
| 1915. | Me | Cl | H | SO | CHMe | |
| 1916. | Me | Cl | H | $SO_2$ | CHMe | |
| 1917. | Me | Cl | H | S | $C(CH_3)_2$ | |
| 1918. | Me | Cl | H | SO | $C(CH_3)_2$ | |
| 1919. | Me | Cl | H | $SO_2$ | $C(CH_3)_2$ | |
| 1920. | Me | Cl | H | S | $C(OC_2H_4O)$ | |
| 1921. | Me | Cl | H | SO | $C(OC_2H_4O)$ | |
| 1922. | Me | Cl | H | $SO_2$ | $C(OC_2H_4O)$ | |
| 1923. | Me | Cl | H | S | $C(SC_2H_4S)$ | |
| 1924. | Me | Cl | H | SO | $C(SC_2H_4S)$ | |
| 1925. | Me | Cl | H | $SO_2$ | $C(SC_2H_4S)$ | |
| 1926. | Me | Cl | H | S | CHOMe | |
| 1927. | Me | Cl | H | SO | CHOMe | |
| 1928. | Me | Cl | H | $SO_2$ | CHOMe | CDCl3, 400 MHz: 2.44 (s, 3H), 3.53 (s, 3H), 3.57 (dd, 1H), 3.71 (d, 1H), 5.15 (d, 1H), 7.55 (d, 1H), 7.74 (d, 1H), 9.40 (s, 1H) |
| 1929. | Me | Cl | H | S | CHOEt | |
| 1930. | Me | Cl | H | SO | CHOEt | |
| 1931. | Me | Cl | H | $SO_2$ | CHOEt | |
| 1932. | Me | Cl | H | S | CHOiPr | |
| 1933. | Me | Cl | H | SO | CHOiPr | |
| 1934. | Me | Cl | H | $SO_2$ | CHOiPr | |
| 1935. | Me | Cl | H | S | $CHOCH_2cPr$ | |
| 1936. | Me | Cl | H | SO | $CHOCH_2cPr$ | |
| 1937. | Me | Cl | H | $SO_2$ | $CHOCH_2cPr$ | |
| 1938. | Me | Cl | H | S | $CHOC_2H_4OMe$ | |
| 1939. | Me | Cl | H | SO | $CHOC_2H_4OMe$ | |
| 1940. | Me | Cl | H | $SO_2$ | $CHOC_2H_4OMe$ | |
| 1941. | Me | Cl | H | S | $CHOCH_2CCH$ | |
| 1942. | Me | Cl | H | SO | $CHOCH_2CCH$ | |
| 1943. | Me | Cl | H | $SO_2$ | $CHOCH_2CCH$ | |
| 1944. | Me | Cl | H | S | $CHOCH_2CH=CH_2$ | |
| 1945. | Me | Cl | H | SO | $CHOCH_2CH=CH_2$ | |
| 1946. | Me | Cl | H | $SO_2$ | $CHOCH_2CH=CH_2$ | |

TABLE 6-continued

Inventive compounds of the general formula (I) in which Q is Q3, $R^5$ is hydrogen and n is 1

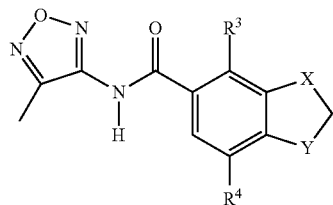

| No. | $R^2$ | $R^3$ | $R^4$ | Y | X | 1H NMR |
|---|---|---|---|---|---|---|
| 1947. | Me | Cl | H | S | 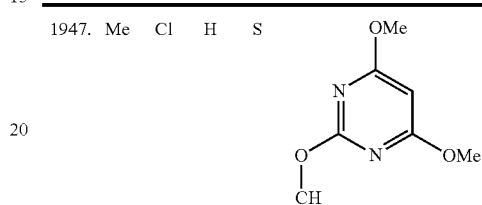 | |
| 1948. | Me | Cl | H | SO | 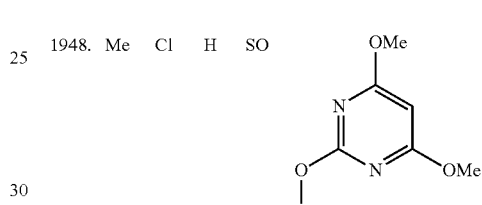 | |
| 1949. | Me | Cl | H | $SO_2$ | 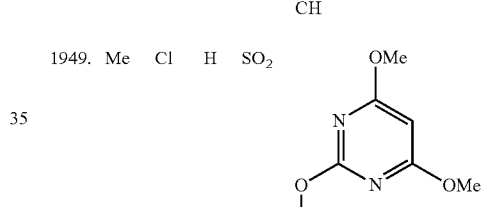 | |
| 1950. | Me | Cl | H | S | 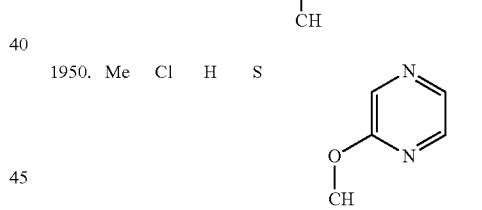 | |
| 1951. | Me | Cl | H | SO | 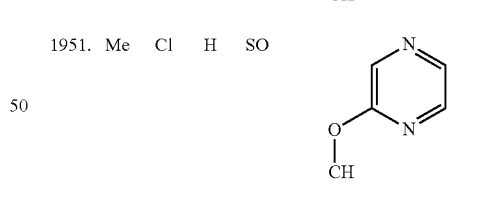 | |
| 1952. | Me | Cl | H | $SO_2$ | 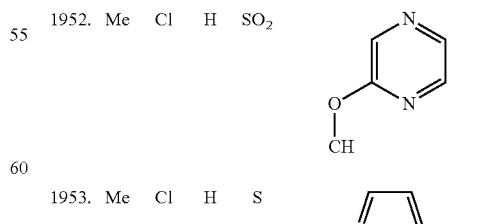 | |
| 1953. | Me | Cl | H | S |  | |

TABLE 6-continued

Inventive compounds of the general formula (I) in which Q is Q3, R⁵ is hydrogen and n is 1

| No. | R² | R³ | R⁴ | Y | X | 1H NMR |
|---|---|---|---|---|---|---|
| 1954. | Me | Cl | H | SO | N-pyrazol-1-yl-CH | |
| 1955. | Me | Cl | H | SO$_2$ | N-pyrazol-1-yl-CH | |
| 1956. | Me | Cl | H | S | 1,2,3-triazol-1-yl-CH | |
| 1957. | Me | Cl | H | SO | 1,2,3-triazol-1-yl-CH | |
| 1958. | Me | Cl | H | SO$_2$ | 1,2,3-triazol-1-yl-CH | |
| 1959. | Me | Cl | H | S | 1,2,3-triazol-2-yl-CH | |
| 1960. | Me | Cl | H | SO | 1,2,3-triazol-2-yl-CH | |
| 1961. | Me | Cl | H | SO$_2$ | 1,2,3-triazol-2-yl-CH | |
| 1962. | Me | Cl | H | S | CHOC$_2$H$_4$F | |
| 1963. | Me | Cl | H | SO | CHOC$_2$H$_4$F | |
| 1964. | Me | Cl | H | SO$_2$ | CHOC$_2$H$_4$F | |
| 1965. | Me | Cl | H | S | C=NOMe | |
| 1966. | Me | Cl | H | SO | C=NOMe | |
| 1967. | Me | Cl | H | SO$_2$ | C=NOMe | |
| 1968. | Me | Cl | H | S | C=NOCH$_2$CCH | |
| 1969. | Me | Cl | H | SO | C=NOCH$_2$CCH | |
| 1970. | Me | Cl | H | SO$_2$ | C=NOCH$_2$CCH | |
| 1971. | Me | Cl | H | S | C=NOCH$_2$CH=CH$_2$ | |
| 1972. | Me | Cl | H | SO | C=NOCH$_2$CH=CH$_2$ | |
| 1973. | Me | Cl | H | SO$_2$ | C=NOCH$_2$CH=CH$_2$ | |
| 1974. | Me | Cl | H | S | C=O | |
| 1975. | Me | Cl | H | SO | C=O | |
| 1976. | Me | Cl | H | SO$_2$ | C=O | |
| 1977. | Me | Cl | H | S | C=S | |
| 1978. | Me | Cl | H | SO | C=S | |
| 1979. | Me | Cl | H | SO$_2$ | C=S | |
| 1980. | Me | Cl | H | S | C=S | |
| 1981. | Me | Cl | H | SO | C=S | |
| 1982. | Me | Cl | H | SO$_2$ | C=S | |
| 1983. | Me | Cl | H | S | C=N—N(CH$_3$)$_2$ | |
| 1984. | Me | Cl | H | SO | C=N—N(CH$_3$)$_2$ | |
| 1985. | Me | Cl | H | SO$_2$ | C=N—N(CH$_3$)$_2$ | |
| 1986. | Me | Cl | H | S | O | |
| 1987. | Me | Cl | H | SO | O | |
| 1988. | Me | Cl | H | SO$_2$ | O | |
| 1989. | Me | Cl | H | S | S | |
| 1990. | Me | Cl | H | SO | S | |
| 1991. | Me | Cl | H | SO$_2$ | S | |
| 1992. | Me | Cl | H | S | SO | |
| 1993. | Me | Cl | H | SO | SO | |
| 1994. | Me | Cl | H | SO$_2$ | SO | |
| 1995. | Me | Cl | H | S | SO$_2$ | |
| 1996. | Me | Cl | H | SO | SO$_2$ | |
| 1997. | Me | Cl | H | SO$_2$ | SO$_2$ | |
| 1998. | Me | Cl | H | S | NMe | |
| 1999. | Me | Cl | H | SO | NMe | |
| 2000. | Me | Cl | H | SO$_2$ | NMe | |
| 2001. | Et | Me | Me | S | CH$_2$ | |
| 2002. | Et | Me | Me | SO | CH$_2$ | |
| 2003. | Et | Me | Me | SO$_2$ | CH$_2$ | |
| 2004. | Et | Me | Me | S | CHMe | |
| 2005. | Et | Me | Me | SO | CHMe | |
| 2006. | Et | Me | Me | SO$_2$ | CHMe | |
| 2007. | Et | Me | Me | S | C(CH$_3$)$_2$ | |
| 2008. | Et | Me | Me | SO | C(CH$_3$)$_2$ | |
| 2009. | Et | Me | Me | SO$_2$ | C(CH$_3$)$_2$ | |
| 2010. | Et | Me | Me | S | C(OC$_2$H$_4$O) | |
| 2011. | Et | Me | Me | SO | C(OC$_2$H$_4$O) | |
| 2012. | Et | Me | Me | SO$_2$ | C(OC$_2$H$_4$O) | |
| 2013. | Et | Me | Me | S | C(SC$_2$H$_4$S) | |
| 2014. | Et | Me | Me | SO | C(SC$_2$H$_4$S) | |
| 2015. | Et | Me | Me | SO$_2$ | C(SC$_2$H$_4$S) | |
| 2016. | Et | Me | Me | S | CHOMe | |
| 2017. | Et | Me | Me | SO | CHOMe | |
| 2018. | Et | Me | Me | SO$_2$ | CHOMe | |
| 2019. | Et | Me | Me | S | CHOEt | |
| 2020. | Et | Me | Me | SO | CHOEt | |
| 2021. | Et | Me | Me | SO$_2$ | CHOEt | |
| 2022. | Et | Me | Me | S | CHOiPr | |
| 2023. | Et | Me | Me | SO | CHOiPr | |
| 2024. | Et | Me | Me | SO$_2$ | CHOiPr | |
| 2025. | Et | Me | Me | S | CHOCH$_2$cPr | |
| 2026. | Et | Me | Me | SO | CHOCH$_2$cPr | |
| 2027. | Et | Me | Me | SO$_2$ | CHOCH$_2$cPr | |
| 2028. | Et | Me | Me | S | CHOC$_2$H$_4$OMe | |
| 2029. | Et | Me | Me | SO | CHOC$_2$H$_4$OMe | |
| 2030. | Et | Me | Me | SO$_2$ | CHOC$_2$H$_4$OMe | |
| 2031. | Et | Me | Me | S | CHOCH$_2$CCH | |
| 2032. | Et | Me | Me | SO | CHOCH$_2$CCH | |
| 2033. | Et | Me | Me | SO$_2$ | CHOCH$_2$CCH | |
| 2034. | Et | Me | Me | S | CHOCH$_2$CH=CH$_2$ | |

TABLE 6-continued

Inventive compounds of the general formula (I) in which Q is Q3, $R^5$ is hydrogen and n is 1

| No. | $R^2$ | $R^3$ | $R^4$ | Y | X | 1H NMR |
|---|---|---|---|---|---|---|
| 2035. | Et | Me | Me | SO | CHOCH$_2$CH=CH$_2$ | |
| 2036. | Et | Me | Me | SO$_2$ | CHOCH$_2$CH=CH$_2$ | |
| 2037. | Et | Me | Me | S | 2,4-dimethoxypyrimidin-6-yl-oxy-CH | |
| 2038. | Et | Me | Me | SO | 2,4-dimethoxypyrimidin-6-yl-oxy-CH | |
| 2039. | Et | Me | Me | SO$_2$ | 2,4-dimethoxypyrimidin-6-yl-oxy-CH | |
| 2040. | Et | Me | Me | S | pyrazin-2-yl-oxy-CH | |
| 2041. | Et | Me | Me | SO | pyrazin-2-yl-oxy-CH | |
| 2042. | Et | Me | Me | SO$_2$ | pyrazin-2-yl-oxy-CH | |
| 2043. | Et | Me | Me | S | pyrazol-1-yl-CH | |
| 2044. | Et | Me | Me | SO | pyrazol-1-yl-CH | |
| 2045. | Et | Me | Me | SO$_2$ | pyrazol-1-yl-CH | |
| 2046. | Et | Me | Me | S | 1,2,3-triazol-1-yl-CH | |
| 2047. | Et | Me | Me | SO | 1,2,3-triazol-1-yl-CH | |
| 2048. | Et | Me | Me | SO$_2$ | 1,2,3-triazol-1-yl-CH | |
| 2049. | Et | Me | Me | S | 1,2,3-triazol-2-yl-CH | |
| 2050. | Et | Me | Me | SO | 1,2,3-triazol-2-yl-CH | |
| 2051. | Et | Me | Me | SO$_2$ | 1,2,3-triazol-2-yl-CH | |
| 2052. | Et | Me | Me | S | CHOC$_2$H$_4$F | |
| 2053. | Et | Me | Me | SO | CHOC$_2$H$_4$F | |
| 2054. | Et | Me | Me | SO$_2$ | CHOC$_2$H$_4$F | |
| 2055. | Et | Me | Me | S | C=NOMe | |
| 2056. | Et | Me | Me | SO | C=NOMe | |
| 2057. | Et | Me | Me | SO$_2$ | C=NOMe | |
| 2058. | Et | Me | Me | S | C=NOCH$_2$CCH | |
| 2059. | Et | Me | Me | SO | C=NOCH$_2$CCH | |
| 2060. | Et | Me | Me | SO$_2$ | C=NOCH$_2$CCH | |

TABLE 6-continued

Inventive compounds of the general formula (I) in which Q is Q3, $R^5$ is hydrogen and n is 1

| No. | $R^2$ | $R^3$ | $R^4$ | Y | X | 1H NMR |
|---|---|---|---|---|---|---|
| 2061. | Et | Me | Me | S | C=NOCH$_2$CH=CH$_2$ | |
| 2062. | Et | Me | Me | SO | C=NOCH$_2$CH=CH$_2$ | |
| 2063. | Et | Me | Me | SO$_2$ | C=NOCH$_2$CH=CH$_2$ | |
| 2064. | Et | Me | Me | S | C=O | |
| 2065. | Et | Me | Me | SO | C=O | |
| 2066. | Et | Me | Me | SO$_2$ | C=O | |
| 2067. | Et | Me | Me | S | C=S | |
| 2068. | Et | Me | Me | SO | C=S | |
| 2069. | Et | Me | Me | SO$_2$ | C=S | |
| 2070. | Et | Me | Me | S | C=S | |
| 2071. | Et | Me | Me | SO | C=S | |
| 2072. | Et | Me | Me | SO$_2$ | C=S | |
| 2073. | Et | Me | Me | S | C=N—N(CH$_3$)$_2$ | |
| 2074. | Et | Me | Me | SO | C=N—N(CH$_3$)$_2$ | |
| 2075. | Et | Me | Me | SO$_2$ | C=N—N(CH$_3$)$_2$ | |
| 2076. | Et | Me | Me | S | O | |
| 2077. | Et | Me | Me | SO | O | |
| 2078. | Et | Me | Me | SO$_2$ | O | |
| 2079. | Et | Me | Me | S | S | |
| 2080. | Et | Me | Me | SO | S | |
| 2081. | Et | Me | Me | SO$_2$ | S | |
| 2082. | Et | Me | Me | S | SO | |
| 2083. | Et | Me | Me | SO | SO | |
| 2084. | Et | Me | Me | SO$_2$ | SO | |
| 2085. | Et | Me | Me | S | SO$_2$ | |
| 2086. | Et | Me | Me | SO | SO$_2$ | |
| 2087. | Et | Me | Me | SO$_2$ | SO$_2$ | |
| 2088. | Et | Me | Me | S | NMe | |
| 2089. | Et | Me | Me | SO | NMe | |
| 2090. | Et | Me | Me | SO$_2$ | NMe | |
| 2091. | Et | Me | Me | O | O | |
| 2092. | Et | Me | H | O | O | |
| 2093. | Et | SMe | H | O | O | |
| 2094. | Et | Cl | H | O | O | |
| 2095. | Et | Cl | H | S | CH$_2$ | |
| 2096. | Et | Cl | H | SO | CH$_2$ | |
| 2097. | Et | Cl | H | SO$_2$ | CH$_2$ | |
| 2098. | Et | Cl | H | S | CHMe | |
| 2099. | Et | Cl | H | SO | CHMe | |
| 2100. | Et | Cl | H | SO$_2$ | CHMe | |
| 2101. | Et | Cl | H | S | C(CH$_3$)$_2$ | |
| 2102. | Et | Cl | H | SO | C(CH$_3$)$_2$ | |
| 2103. | Et | Cl | H | SO$_2$ | C(CH$_3$)$_2$ | |
| 2104. | Et | Cl | H | S | C(OC$_2$H$_4$O) | |
| 2105. | Et | Cl | H | SO | C(OC$_2$H$_4$O) | |
| 2106. | Et | Cl | H | SO$_2$ | C(OC$_2$H$_4$O) | |
| 2107. | Et | Cl | H | S | C(SC$_2$H$_4$S) | |
| 2108. | Et | Cl | H | SO | C(SC$_2$H$_4$S) | |
| 2109. | Et | Cl | H | SO$_2$ | C(SC$_2$H$_4$S) | |
| 2110. | Et | Cl | H | S | CHOMe | |
| 2111. | Et | Cl | H | SO | CHOMe | |
| 2112. | Et | Cl | H | SO$_2$ | CHOMe | |
| 2113. | Et | Cl | H | S | CHOEt | |
| 2114. | Et | Cl | H | SO | CHOEt | |
| 2115. | Et | Cl | H | SO$_2$ | CHOEt | |
| 2116. | Et | Cl | H | S | CHOiPr | |
| 2117. | Et | Cl | H | SO | CHOiPr | |
| 2118. | Et | Cl | H | SO$_2$ | CHOiPr | |
| 2119. | Et | Cl | H | S | CHOCH$_2$cPr | |
| 2120. | Et | Cl | H | SO | CHOCH$_2$cPr | |
| 2121. | Et | Cl | H | SO$_2$ | CHOCH$_2$cPr | |
| 2122. | Et | Cl | H | S | CHOC$_2$H$_4$OMe | |
| 2123. | Et | Cl | H | SO | CHOC$_2$H$_4$OMe | |
| 2124. | Et | Cl | H | SO$_2$ | CHOC$_2$H$_4$OMe | |
| 2125. | Et | Cl | H | S | CHOCH$_2$CCH | |
| 2126. | Et | Cl | H | SO | CHOCH$_2$CCH | |
| 2127. | Et | Cl | H | SO$_2$ | CHOCH$_2$CCH | |
| 2128. | Et | Cl | H | S | CHOCH$_2$CH=CH$_2$ | |
| 2129. | Et | Cl | H | SO | CHOCH$_2$CH=CH$_2$ | |
| 2130. | Et | Cl | H | SO$_2$ | CHOCH$_2$CH=CH$_2$ | |
| 2131. | Et | Cl | H | S | 4,6-dimethoxypyrimidin-2-yloxy-CH | |
| 2132. | Et | Cl | H | SO | 4,6-dimethoxypyrimidin-2-yloxy-CH | |
| 2133. | Et | Cl | H | SO$_2$ | 4,6-dimethoxypyrimidin-2-yloxy-CH | |
| 2134. | Et | Cl | H | S | pyrazin-2-yloxy-CH | |
| 2135. | Et | Cl | H | SO | pyrazin-2-yloxy-CH | |
| 2136. | Et | Cl | H | SO$_2$ | pyrazin-2-yloxy-CH | |

TABLE 6-continued

Inventive compounds of the general formula (I) in which Q is Q3, $R^5$ is hydrogen and n is 1

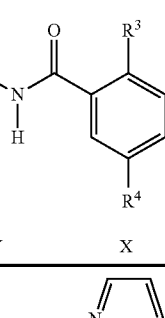

| No. | $R^2$ | $R^3$ | $R^4$ | Y | X | 1H NMR |
|---|---|---|---|---|---|---|
| 2137. | Et | Cl | H | S | pyrazol-1-yl-CH | |
| 2138. | Et | Cl | H | SO | pyrazol-1-yl-CH | |
| 2139. | Et | Cl | H | SO$_2$ | pyrazol-1-yl-CH | |
| 2140. | Et | Cl | H | S | 1,2,3-triazol-2-yl-CH | |
| 2141. | Et | Cl | H | SO | 1,2,3-triazol-2-yl-CH | |
| 2142. | Et | Cl | H | SO$_2$ | 1,2,3-triazol-2-yl-CH | |
| 2143. | Et | Cl | H | S | 1,2,3-triazol-1-yl-CH | |
| 2144. | Et | Cl | H | SO | 1,2,3-triazol-1-yl-CH | |
| 2145. | Et | Cl | H | SO$_2$ | 1,2,3-triazol-1-yl-CH | |
| 2146. | Et | Cl | H | S | CHOC$_2$H$_4$F | |
| 2147. | Et | Cl | H | SO | CHOC$_2$H$_4$F | |
| 2148. | Et | Cl | H | SO$_2$ | CHOC$_2$H$_4$F | |

TABLE 6-continued

Inventive compounds of the general formula (I) in which Q is Q3, $R^5$ is hydrogen and n is 1

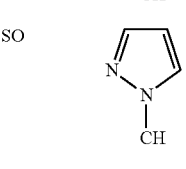

| No. | $R^2$ | $R^3$ | $R^4$ | Y | X | 1H NMR |
|---|---|---|---|---|---|---|
| 2149. | Et | Cl | H | S | C=NOMe | |
| 2150. | Et | Cl | H | SO | C=NOMe | |
| 2151. | Et | Cl | H | SO$_2$ | C=NOMe | |
| 2152. | Et | Cl | H | S | C=NOCH$_2$CCH | |
| 2153. | Et | Cl | H | SO | C=NOCH$_2$CCH | |
| 2154. | Et | Cl | H | SO$_2$ | C=NOCH$_2$CCH | |
| 2155. | Et | Cl | H | S | C=NOCH$_2$CH=CH$_2$ | |
| 2156. | Et | Cl | H | SO | C=NOCH$_2$CH=CH$_2$ | |
| 2157. | Et | Cl | H | SO$_2$ | C=NOCH$_2$CH=CH$_2$ | |
| 2158. | Et | Cl | H | S | C=O | |
| 2159. | Et | Cl | H | SO | C=O | |
| 2160. | Et | Cl | H | SO$_2$ | C=O | |
| 2161. | Et | Cl | H | S | C=S | |
| 2162. | Et | Cl | H | SO | C=S | |
| 2163. | Et | Cl | H | SO$_2$ | C=S | |
| 2164. | Et | Cl | H | S | C=S | |
| 2165. | Et | Cl | H | SO | C=S | |
| 2166. | Et | Cl | H | SO$_2$ | C=S | |
| 2167. | Et | Cl | H | S | C=N—N(CH$_3$)$_2$ | |
| 2168. | Et | Cl | H | SO | C=N—N(CH$_3$)$_2$ | |
| 2169. | Et | Cl | H | SO$_2$ | C=N—N(CH$_3$)$_2$ | |
| 2170. | Et | Cl | H | S | O | |
| 2171. | Et | Cl | H | SO | O | |
| 2172. | Et | Cl | H | SO$_2$ | O | |
| 2173. | Et | Cl | H | S | S | |
| 2174. | Et | Cl | H | SO | S | |
| 2175. | Et | Cl | H | SO$_2$ | S | |
| 2176. | Et | Cl | H | S | SO | |
| 2177. | Et | Cl | H | SO | SO | |
| 2178. | Et | Cl | H | SO$_2$ | SO | |
| 2179. | Et | Cl | H | S | SO$_2$ | |
| 2180. | Et | Cl | H | SO | SO$_2$ | |
| 2181. | Et | Cl | H | SO$_2$ | SO$_2$ | |
| 2182. | Et | Cl | H | S | NMe | |
| 2183. | Et | Cl | H | SO | NMe | |
| 2184. | Et | Cl | H | SO$_2$ | NMe | |

TABLE 7

Inventive compounds of the general formula (I) in which Q is Q1, X and Y are each oxygen, $R^5$ is fluorine and n is 1

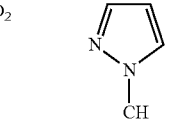

| No. | $R^1$ | $R^3$ | $R^4$ | 1H NMR |
|---|---|---|---|---|
| 2185. | Me | Me | Me | |
| 2186. | Me | Me | H | DMSO-d6, 400 MHz: 7.62 (d, 1H), 7.40 (d, 1H), 3.90 (s, 3H), 2.39 (s, 3H) |
| 2187. | Me | Cl | H | |

TABLE 7-continued

Inventive compounds of the general formula (I) in which Q is Q1, X and Y are each oxygen, $R^5$ is fluorine and n is 1

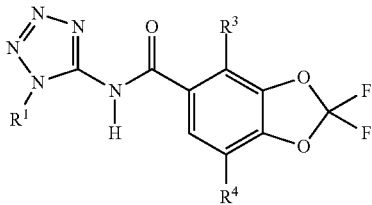

| No. | $R^1$ | $R^3$ | $R^4$ | 1H NMR |
|---|---|---|---|---|
| 2188. | Me | SMe | H | |
| 2189. | Me | Me | Me | |
| 2190. | Me | Me | H | |
| 2191. | Me | Cl | H | |
| 2192. | Me | SMe | H | |
| 2193. | Et | Me | Me | |
| 2194. | Et | Me | H | |
| 2195. | Et | Cl | H | |
| 2196. | Et | SMe | H | |
| 2197. | Et | Me | Me | |
| 2198. | Et | Me | H | |
| 2199. | Et | Cl | H | |
| 2200. | Et | SMe | H | |

TABLE 8

Inventive compounds of the general formula (I) in which Q is Q3, X is 2-(1,4-pyrazinyl)oxymethyl, Y is $SO_2$, $R^5$ is hydrogen and n is 2

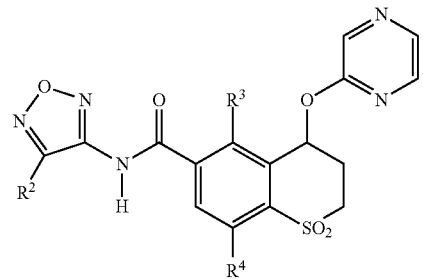

| No. | $R^2$ | $R^3$ | $R^4$ | 1H NMR |
|---|---|---|---|---|
| 2201. | Cl | Me | Me | |
| 2202. | Cl | Me | H | |
| 2203. | Cl | Cl | H | |
| 2204. | OMe | Me | Me | DMSO-$d_6$, 400 MHz: 11.36 (s, 1H), 8.38 (s, 1H), 8.33-8.31 (m, 2H), 7.60 (s, 1H), 6.51 (dd, 1H), 4.07 (s, 3H), 3.77-3.70 (m, 1H), 3.58-3.53 (m, 1H), 2.76-2.60 (m, 5H), 2.18 (s, 3H) |
| 2205. | OMe | Me | H | |
| 2206. | OMe | Cl | H | |
| 2207. | NHAc | Me | Me | |
| 2208. | NHAc | Me | H | |
| 2209. | NHAc | Cl | H | |

TABLE 9

Inventive compounds of the general formula (I) in which Q is Q1, Y is $SO_2$, $R^5$ is hydrogen and n is 1

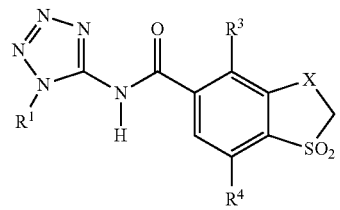

| No. | $R^1$ | $R^3$ | $R^4$ | X | 1H NMR |
|---|---|---|---|---|---|
| 2210. | nPr | Me | Me | $CH_2$ | |
| 2211. | nPr | Me | H | $CH_2$ | |
| 2212. | nPr | Cl | H | $CH_2$ | DMSO-$d_6$, 400 MHz: 0.89 (t, 3H), 1.89 (m, 2H), 3.42 (t, 2H), 3.76 (t, 2H), 4.33 (t, 2H), 7.90 (d, 1H), 7.94 (d, 1H), 11.84 (s, 1H) |
| 2213. | $C_2H_4$OMe | Me | Me | $CH_2$ | |
| 2214. | $C_2H_4$OMe | Me | H | $CH_2$ | |
| 2215. | $C_2H_4$OMe | Cl | H | $CH_2$ | |
| 2216. | $CH_2CF_3$ | Me | Me | $CH_2$ | |
| 2217. | $CH_2CF_3$ | Me | H | $CH_2$ | |
| 2218. | $CH_2CF_3$ | Cl | H | $CH_2$ | |
| 2219. | nPr | Me | Me | CHOMe | |
| 2220. | nPr | Me | H | CHOMe | |
| 2221. | nPr | Cl | H | CHOMe | DMSO-$d_6$, 400 MHz: 0.99 (t, 3H), 2.01 (m, 2H), 3.53 (s, 3H), 3.63 (dd, 1H), 3.80 (d, 1H), 4.40 (t, 2H), 5.22 (d, 1H), 7.72 (d, 1H), 7.92 (d, 1H), 10.80 (s, 1H) |
| 2222. | $C_2H_4$OMe | Me | Me | CHOMe | |
| 2223. | $C_2H_4$OMe | Me | H | CHOMe | |
| 2224. | $C_2H_4$OMe | Cl | H | CHOMe | |
| 2225. | $CH_2CF_3$ | Me | Me | CHOMe | |
| 2226. | $CH_2CF_3$ | Me | H | CHOMe | |
| 2227. | $CH_2CF_3$ | Cl | H | CHOMe | |

TABLE 10

Inventive compounds of the general formula (I) in which Q is Q1 and R⁵ is hydrogen and n is 1

| No. | R¹ | R³ | R⁴ | X | Y | 1H NMR |
|---|---|---|---|---|---|---|
| 2228. | Me | Me | Me | S | C=O | |
| 2229. | Me | Me | Me | SO | C=O | |
| 2230. | Me | Me | Me | SO₂ | C=O | |
| 2231. | Me | Me | Me | S | CHOMe | |
| 2232. | Me | Me | Me | SO | CHOMe | |
| 2233. | Me | Me | Me | SO₂ | CHOMe | |
| 2234. | Me | Me | Me | S | CHOEt | |
| 2235. | Me | Me | Me | SO | CHOEt | |
| 2236. | Me | Me | Me | SO₂ | CHOEt | |
| 2237. | Me | Me | Me | S | C=NOMe | |
| 2238. | Me | Me | Me | SO | C=NOMe | |
| 2239. | Me | Me | Me | SO₂ | C=NOMe | |
| 2240. | Me | Me | Me | S | C=NOEt | |
| 2241. | Me | Me | Me | SO | C=NOEt | |
| 2242. | Me | Me | Me | SO₂ | C=NOEt | |
| 2243. | Me | Me | Me | S | O | |
| 2244. | Me | Me | Me | SO | O | |
| 2245. | Me | Me | Me | SO₂ | O | |
| 2246. | Me | Me | Me | S | S | |
| 2247. | Me | Me | Me | SO | S | |
| 2248. | Me | Me | Me | SO₂ | S | |
| 2249. | Me | Me | Me | S | SO₂ | |
| 2250. | Me | Me | Me | SO | SO₂ | |
| 2251. | Me | Me | Me | SO₂ | SO₂ | |
| 2252. | Me | Me | H | S | C=O | |
| 2253. | Me | Me | H | SO | C=O | |
| 2254. | Me | Me | H | SO₂ | C=O | |
| 2255. | Me | Me | H | S | CHOMe | |
| 2256. | Me | Me | H | SO | CHOMe | |
| 2257. | Me | Me | H | SO₂ | CHOMe | |
| 2258. | Me | Me | H | S | CHOEt | |
| 2259. | Me | Me | H | SO | CHOEt | |
| 2260. | Me | Me | H | SO₂ | CHOEt | |
| 2261. | Me | Me | H | S | C=NOMe | |
| 2262. | Me | Me | H | SO | C=NOMe | |
| 2263. | Me | Me | H | SO₂ | C=NOMe | |
| 2264. | Me | Me | H | S | C=NOEt | |
| 2265. | Me | Me | H | SO | C=NOEt | |
| 2266. | Me | Me | H | SO₂ | C=NOEt | |
| 2267. | Me | Me | H | S | O | |
| 2268. | Me | Me | H | SO | O | |
| 2269. | Me | Me | H | SO₂ | O | |
| 2270. | Me | Me | H | S | S | |
| 2271. | Me | Me | H | SO | S | |
| 2272. | Me | Me | H | SO₂ | S | |
| 2273. | Me | Me | H | S | SO₂ | |
| 2274. | Me | Me | H | SO | SO₂ | |
| 2275. | Me | Me | H | SO₂ | SO₂ | |

TABLE 11

Inventive compounds of the general formula (I) in which Q is Q2, R⁵ is hydrogen and n is 1

| No. | R¹ | R³ | R⁴ | X | Y | 1H NMR |
|---|---|---|---|---|---|---|
| 2276. | Me | Me | Me | S | C=O | |
| 2277. | Me | Me | Me | SO | C=O | |
| 2278. | Me | Me | Me | SO₂ | C=O | |
| 2279. | Me | Me | Me | S | CHOMe | |
| 2280. | Me | Me | Me | SO | CHOMe | |
| 2281. | Me | Me | Me | SO₂ | CHOMe | |
| 2282. | Me | Me | Me | S | CHOEt | |
| 2283. | Me | Me | Me | SO | CHOEt | |
| 2284. | Me | Me | Me | SO₂ | CHOEt | |
| 2285. | Me | Me | Me | S | C=NOMe | |
| 2286. | Me | Me | Me | SO | C=NOMe | |
| 2287. | Me | Me | Me | SO₂ | C=NOMe | |
| 2288. | Me | Me | Me | S | C=NOEt | |
| 2289. | Me | Me | Me | SO | C=NOEt | |
| 2290. | Me | Me | Me | SO₂ | C=NOEt | |
| 2291. | Me | Me | Me | S | O | |
| 2292. | Me | Me | Me | SO | O | |
| 2293. | Me | Me | Me | SO₂ | O | |
| 2294. | Me | Me | Me | S | S | |
| 2295. | Me | Me | Me | SO | S | |
| 2296. | Me | Me | Me | SO₂ | S | |
| 2297. | Me | Me | Me | S | SO₂ | |
| 2298. | Me | Me | Me | SO | SO₂ | |
| 2299. | Me | Me | Me | SO₂ | SO₂ | |
| 2300. | Me | Me | H | S | C=O | |
| 2301. | Me | Me | H | SO | C=O | |
| 2302. | Me | Me | H | SO₂ | C=O | |
| 2303. | Me | Me | H | S | CHOMe | |
| 2304. | Me | Me | H | SO | CHOMe | |
| 2305. | Me | Me | H | SO₂ | CHOMe | |
| 2306. | Me | Me | H | S | CHOEt | |
| 2307. | Me | Me | H | SO | CHOEt | |
| 2308. | Me | Me | H | SO₂ | CHOEt | |
| 2309. | Me | Me | H | S | C=NOMe | |
| 2310. | Me | Me | H | SO | C=NOMe | |
| 2311. | Me | Me | H | SO₂ | C=NOMe | |
| 2312. | Me | Me | H | S | C=NOEt | |
| 2313. | Me | Me | H | SO | C=NOEt | |
| 2314. | Me | Me | H | SO₂ | C=NOEt | |
| 2315. | Me | Me | H | S | O | |
| 2316. | Me | Me | H | SO | O | |
| 2317. | Me | Me | H | SO₂ | O | |
| 2318. | Me | Me | H | S | S | |
| 2319. | Me | Me | H | SO | S | |
| 2320. | Me | Me | H | SO₂ | S | |
| 2321. | Me | Me | H | S | SO₂ | |
| 2322. | Me | Me | H | SO | SO₂ | |
| 2323. | Me | Me | H | SO₂ | SO₂ | |

TABLE 12

Inventive compounds of the general formula (I) in which Q is Q3, $R^5$ is hydrogen and n is 1

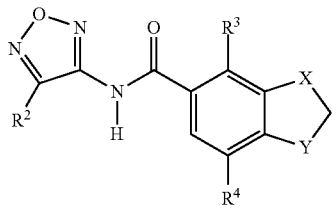

| No. | $R^2$ | $R^3$ | $R^4$ | X | Y | 1H NMR |
|---|---|---|---|---|---|---|
| 2324. | Me | Me | Me | S | C=O | |
| 2325. | Me | Me | Me | SO | C=O | |
| 2326. | Me | Me | Me | $SO_2$ | C=O | |
| 2327. | Me | Me | Me | S | CHOMe | |
| 2328. | Me | Me | Me | SO | CHOMe | |
| 2329. | Me | Me | Me | $SO_2$ | CHOMe | |
| 2330. | Me | Me | Me | S | CHOEt | |
| 2331. | Me | Me | Me | SO | CHOEt | |
| 2332. | Me | Me | Me | $SO_2$ | CHOEt | |
| 2333. | Me | Me | Me | S | C=NOMe | |
| 2334. | Me | Me | Me | SO | C=NOMe | |
| 2335. | Me | Me | Me | $SO_2$ | C=NOMe | |
| 2336. | Me | Me | Me | S | C=NOEt | |
| 2337. | Me | Me | Me | SO | C=NOEt | |
| 2338. | Me | Me | Me | $SO_2$ | C=NOEt | |
| 2339. | Me | Me | Me | S | O | |
| 2340. | Me | Me | Me | SO | O | |
| 2341. | Me | Me | Me | $SO_2$ | O | |
| 2342. | Me | Me | Me | S | S | |
| 2343. | Me | Me | Me | SO | S | |
| 2344. | Me | Me | Me | $SO_2$ | S | |
| 2345. | Me | Me | Me | S | $SO_2$ | |
| 2346. | Me | Me | Me | SO | $SO_2$ | |
| 2347. | Me | Me | Me | $SO_2$ | $SO_2$ | |
| 2348. | Me | Me | H | S | C=O | |
| 2349. | Me | Me | H | SO | C=O | |
| 2350. | Me | Me | H | $SO_2$ | C=O | |
| 2351. | Me | Me | H | S | CHOMe | |
| 2352. | Me | Me | H | SO | CHOMe | |
| 2353. | Me | Me | H | $SO_2$ | CHOMe | |
| 2354. | Me | Me | H | S | CHOEt | |
| 2355. | Me | Me | H | SO | CHOEt | |
| 2356. | Me | Me | H | $SO_2$ | CHOEt | |
| 2357. | Me | Me | H | S | C=NOMe | |
| 2358. | Me | Me | H | SO | C=NOMe | |
| 2359. | Me | Me | H | $SO_2$ | C=NOMe | |
| 2360. | Me | Me | H | S | C=NOEt | |
| 2361. | Me | Me | H | SO | C=NOEt | |
| 2362. | Me | Me | H | $SO_2$ | C=NOEt | |
| 2363. | Me | Me | H | S | O | |
| 2364. | Me | Me | H | SO | O | |
| 2365. | Me | Me | H | $SO_2$ | O | |
| 2366. | Me | Me | H | S | S | |
| 2367. | Me | Me | H | SO | S | |
| 2368. | Me | Me | H | $SO_2$ | S | |
| 2369. | Me | Me | H | S | $SO_2$ | |
| 2370. | Me | Me | H | SO | $SO_2$ | |
| 2371. | Me | Me | H | $SO_2$ | $SO_2$ | |

TABLE 13

Inventive compounds of the general formula (I) in which Q is Q1, $R^5$ is hydrogen and n is 2

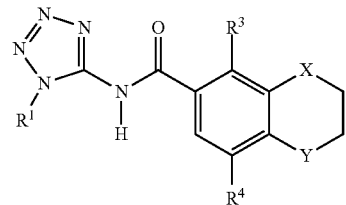

| No. | $R^1$ | $R^3$ | $R^4$ | X | Y | 1H NMR |
|---|---|---|---|---|---|---|
| 2372. | Me | Me | Me | S | C=O | |
| 2373. | Me | Me | Me | SO | C=O | |
| 2374. | Me | Me | Me | $SO_2$ | C=O | |
| 2375. | Me | Me | Me | S | CHOMe | |
| 2376. | Me | Me | Me | SO | CHOMe | |
| 2377. | Me | Me | Me | $SO_2$ | CHOMe | |
| 2378. | Me | Me | Me | S | CHOEt | |
| 2379. | Me | Me | Me | SO | CHOEt | |
| 2380. | Me | Me | Me | $SO_2$ | CHOEt | |
| 2381. | Me | Me | Me | S | C=NOMe | |
| 2382. | Me | Me | Me | SO | C=NOMe | |
| 2383. | Me | Me | Me | $SO_2$ | C=NOMe | |
| 2384. | Me | Me | Me | S | C=NOEt | |
| 2385. | Me | Me | Me | SO | C=NOEt | |
| 2386. | Me | Me | Me | $SO_2$ | C=NOEt | |
| 2387. | Me | Me | Me | S | O | |
| 2388. | Me | Me | Me | SO | O | |
| 2389. | Me | Me | Me | $SO_2$ | O | |
| 2390. | Me | Me | Me | S | S | |
| 2391. | Me | Me | Me | SO | S | |
| 2392. | Me | Me | Me | $SO_2$ | S | |
| 2393. | Me | Me | Me | S | $SO_2$ | |
| 2394. | Me | Me | Me | SO | $SO_2$ | |
| 2395. | Me | Me | Me | $SO_2$ | $SO_2$ | |
| 2396. | Me | Me | H | S | C=O | |
| 2397. | Me | Me | H | SO | C=O | |
| 2398. | Me | Me | H | $SO_2$ | C=O | |
| 2399. | Me | Me | H | S | CHOMe | |
| 2400. | Me | Me | H | SO | CHOMe | |
| 2401. | Me | Me | H | $SO_2$ | CHOMe | |
| 2402. | Me | Me | H | S | CHOEt | |
| 2403. | Me | Me | H | SO | CHOEt | |
| 2404. | Me | Me | H | $SO_2$ | CHOEt | |
| 2405. | Me | Me | H | S | C=NOMe | |
| 2406. | Me | Me | H | SO | C=NOMe | |
| 2407. | Me | Me | H | $SO_2$ | C=NOMe | |
| 2408. | Me | Me | H | S | C=NOEt | |
| 2409. | Me | Me | H | SO | C=NOEt | |
| 2410. | Me | Me | H | $SO_2$ | C=NOEt | |
| 2411. | Me | Me | H | S | O | |
| 2412. | Me | Me | H | SO | O | |
| 2413. | Me | Me | H | $SO_2$ | O | |
| 2414. | Me | Me | H | S | S | |
| 2415. | Me | Me | H | SO | S | |
| 2416. | Me | Me | H | $SO_2$ | S | |
| 2417. | Me | Me | H | S | $SO_2$ | |
| 2418. | Me | Me | H | SO | $SO_2$ | |
| 2419. | Me | Me | H | $SO_2$ | $SO_2$ | |

TABLE 14

Inventive compounds of the general formula (I) in which Q is Q2, $R^5$ is hydrogen and n is 2

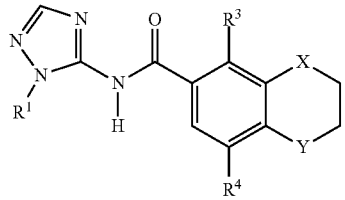

| No. | $R^1$ | $R^3$ | $R^4$ | X | Y | 1H NMR |
|---|---|---|---|---|---|---|
| 2420. | Me | Me | Me | S | C=O | |
| 2421. | Me | Me | Me | SO | C=O | |
| 2422. | Me | Me | Me | $SO_2$ | C=O | |
| 2423. | Me | Me | Me | S | CHOMe | |
| 2424. | Me | Me | Me | SO | CHOMe | |
| 2425. | Me | Me | Me | $SO_2$ | CHOMe | |
| 2426. | Me | Me | Me | S | CHOEt | |
| 2427. | Me | Me | Me | SO | CHOEt | |
| 2428. | Me | Me | Me | $SO_2$ | CHOEt | |
| 2429. | Me | Me | Me | S | C=NOMe | |
| 2430. | Me | Me | Me | SO | C=NOMe | |
| 2431. | Me | Me | Me | $SO_2$ | C=NOMe | |
| 2432. | Me | Me | Me | S | C=NOEt | |
| 2433. | Me | Me | Me | SO | C=NOEt | |
| 2434. | Me | Me | Me | $SO_2$ | C=NOEt | |
| 2435. | Me | Me | Me | S | O | |
| 2436. | Me | Me | Me | SO | O | |
| 2437. | Me | Me | Me | $SO_2$ | O | |
| 2438. | Me | Me | Me | S | S | |
| 2439. | Me | Me | Me | SO | S | |
| 2440. | Me | Me | Me | $SO_2$ | S | |
| 2441. | Me | Me | Me | S | $SO_2$ | |
| 2442. | Me | Me | Me | SO | $SO_2$ | |
| 2443. | Me | Me | Me | $SO_2$ | $SO_2$ | |
| 2444. | Me | Me | H | S | C=O | |
| 2445. | Me | Me | H | SO | C=O | |
| 2446. | Me | Me | H | $SO_2$ | C=O | |
| 2447. | Me | Me | H | S | CHOMe | |
| 2448. | Me | Me | H | SO | CHOMe | |
| 2449. | Me | Me | H | $SO_2$ | CHOMe | |
| 2450. | Me | Me | H | S | CHOEt | |
| 2451. | Me | Me | H | SO | CHOEt | |
| 2452. | Me | Me | H | $SO_2$ | CHOEt | |
| 2453. | Me | Me | H | S | C=NOMe | |
| 2454. | Me | Me | H | SO | C=NOMe | |
| 2455. | Me | Me | H | $SO_2$ | C=NOMe | |
| 2456. | Me | Me | H | S | C=NOEt | |
| 2457. | Me | Me | H | SO | C=NOEt | |
| 2458. | Me | Me | H | $SO_2$ | C=NOEt | |
| 2459. | Me | Me | H | S | O | |
| 2460. | Me | Me | H | SO | O | |
| 2461. | Me | Me | H | $SO_2$ | O | |
| 2462. | Me | Me | H | S | S | |
| 2463. | Me | Me | H | SO | S | |
| 2464. | Me | Me | H | $SO_2$ | S | |
| 2465. | Me | Me | H | S | $SO_2$ | |
| 2466. | Me | Me | H | SO | $SO_2$ | |
| 2467. | Me | Me | H | $SO_2$ | $SO_2$ | |

TABLE 15

Inventive compounds of the general formula (I) in which Q is Q3, $R^5$ is hydrogen and n is 2

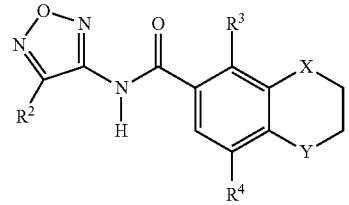

| No. | $R^1$ | $R^3$ | $R^4$ | X | Y | 1H NMR |
|---|---|---|---|---|---|---|
| 2468. | Me | Me | Me | S | C=O | |
| 2469. | Me | Me | Me | SO | C=O | |
| 2470. | Me | Me | Me | $SO_2$ | C=O | |
| 2471. | Me | Me | Me | S | CHOMe | |
| 2472. | Me | Me | Me | SO | CHOMe | |
| 2473. | Me | Me | Me | $SO_2$ | CHOMe | |
| 2474. | Me | Me | Me | S | CHOEt | |
| 2475. | Me | Me | Me | SO | CHOEt | |
| 2476. | Me | Me | Me | $SO_2$ | CHOEt | |
| 2477. | Me | Me | Me | S | C=NOMe | |
| 2478. | Me | Me | Me | SO | C=NOMe | |
| 2479. | Me | Me | Me | $SO_2$ | C=NOMe | |
| 2480. | Me | Me | Me | S | C=NOEt | |
| 2481. | Me | Me | Me | SO | C=NOEt | |
| 2482. | Me | Me | Me | $SO_2$ | C=NOEt | |
| 2483. | Me | Me | Me | S | O | |
| 2484. | Me | Me | Me | SO | O | |
| 2485. | Me | Me | Me | $SO_2$ | O | |
| 2486. | Me | Me | Me | S | S | |
| 2487. | Me | Me | Me | SO | S | |
| 2488. | Me | Me | Me | $SO_2$ | S | |
| 2489. | Me | Me | Me | S | $SO_2$ | |
| 2490. | Me | Me | Me | SO | $SO_2$ | |
| 2491. | Me | Me | Me | $SO_2$ | $SO_2$ | |
| 2492. | Me | Me | H | S | C=O | |
| 2493. | Me | Me | H | SO | C=O | |
| 2494. | Me | Me | H | $SO_2$ | C=O | |
| 2495. | Me | Me | H | S | CHOMe | |
| 2496. | Me | Me | H | SO | CHOMe | |
| 2497. | Me | Me | H | $SO_2$ | CHOMe | |
| 2498. | Me | Me | H | S | CHOEt | |
| 2499. | Me | Me | H | SO | CHOEt | |
| 2500. | Me | Me | H | $SO_2$ | CHOEt | |
| 2501. | Me | Me | H | S | C=NOMe | |
| 2502. | Me | Me | H | SO | C=NOMe | |
| 2503. | Me | Me | H | $SO_2$ | C=NOMe | |
| 2504. | Me | Me | H | S | C=NOEt | |
| 2505. | Me | Me | H | SO | C=NOEt | |
| 2506. | Me | Me | H | $SO_2$ | C=NOEt | |
| 2507. | Me | Me | H | S | O | |
| 2508. | Me | Me | H | SO | O | |
| 2509. | Me | Me | H | $SO_2$ | O | |
| 2510. | Me | Me | H | S | S | |
| 2511. | Me | Me | H | SO | S | |
| 2512. | Me | Me | H | $SO_2$ | S | |
| 2513. | Me | Me | H | S | $SO_2$ | |
| 2514. | Me | Me | H | SO | $SO_2$ | |
| 2515. | Me | Me | H | $SO_2$ | $SO_2$ | |

B. FORMULATION EXAMPLES a) A dusting product is obtained by mixing 10 parts by weight of a compound of the formula (I) and/or a salt thereof and 90 parts by weight of talc as an inert substance, and comminuting the mixture in a hammer mill.

b) A readily water-dispersible wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
75 parts by weight of a compound of the formula (I) and/or salts thereof,
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill and granulating the powder in a fluidized bed by spraying on water as a granulating liquid.

f) Water-dispersible granules are also obtained by homogenizing and precomminuting
25 parts by weight of a compound of the formula (I) and/or salts thereof,
5 parts by weight of sodium 2,2'-dinaphthylmethane-6,6'-disulfonate,
2 parts by weight of sodium oleylmethyltaurate,
1 part by weight of polyvinyl alcohol,
17 parts by weight of calcium carbonate and
50 parts by weight of water
in a colloid mill, then grinding the mixture in a bead mill and atomizing and drying the resulting suspension in a spray tower by means of a one-substance nozzle.

C. BIOLOGICAL EXAMPLES

1. Pre-Emergence Herbicidal Action Against Harmful Plants

Seeds of monocotyledonous and dicotyledonous weed plants and crop plants are placed in wood-fiber pots in sandy loam and covered with soil. The inventive compounds formulated in the form of wettable powders (WP) or as emulsion concentrates (EC) are then applied to the surface of the covering soil as an aqueous suspension or emulsion at a water application rate of 600 to 800 l/ha (converted) with addition of 0.2% wetting agent. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). For example, compounds No. 7, 9, 40, 187 and 189 at an application rate of 320 g/ha each show at least 80% efficacy against *Abutilon* theophrasti and *Amaranthus* retroflexus. Compounds No. 9, 40, 187, 189 and 2204 at an application rate of 320 g/ha each show at least 80% efficacy against *Matricaria* inodora, *Stellaria* media and *Veronica persica*.

2. Post-Emergence Herbicidal Action Against Harmful Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The inventive compounds formulated in the form of wettable powders (WP) or as emulsion concentrates (EC) are then sprayed onto the green parts of the plants as an aqueous suspension or emulsion at a water application rate of 600 to 800 l/ha (converted) with addition of 0.2% wetting agent. After the test plants have been left to stand in the greenhouse under optimal growth conditions for about 3 weeks, the action of the formulations is scored visually in comparison to untreated controls (herbicidal action in percent (%): 100% action=the plants have died, 0% action=like control plants).

Examples of good post-emergence efficacy (PO). For example, compounds No. 7 and 2204 at an application rate of 80 g/ha each show at least 80% efficacy against *Abutilon* theophrasti and *Viola tricolor*. Compounds No. 9, 187 and 189 at an application rate of 80 g/ha each show at least 80% efficacy against *Abutilon* theophrasti and *Amaranthus* retroflexus. Compounds No. 40, 187 and 189 at an application rate of 80 g/ha each show at least 80% efficacy against *Matricaria* inodora, *Stellaria* media and *Veronica Persica*.

The invention claimed is:

1. An N-(1,2,5-oxadiazol-3-yl)-, N-(tetrazol-5-yl)- or N-(triazol-5-yl)bicycloarylcarboxamide of the formula (I) or a salt thereof

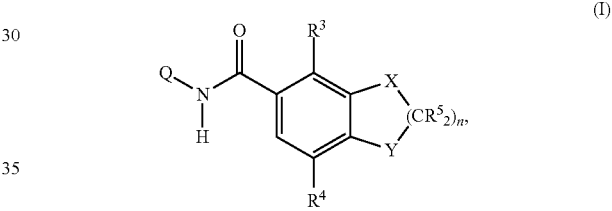

in which

Q is a Q1, Q2 or Q3 radical,

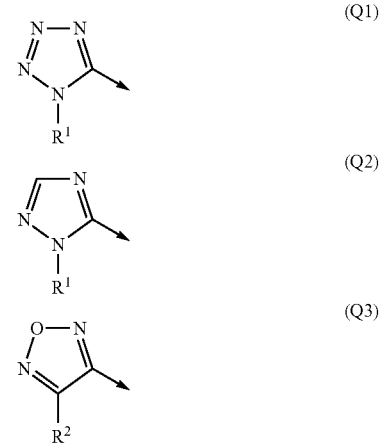

$R^1$ is $(C_1-C_6)$-alkyl, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_1-C_6)$-alkoxy-$(C_1-C_6)$-alkyl, $(C_1-C_6)$- alkoxy-$(C_2-C_6)$-alkenyl, $(C_1-C_6)$-alkoxy-$(C_2-C_6)$-alkynyl, $CH_2R^6$, heteroaryl, heterocyclyl or phenyl, where the three latter radicals are each substituted by u radicals from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkylthio, $(C_1-C_6)$-alkylsulfinyl, $(C_1-C_6)$-alkylsulfonyl, $(C_1-C_6)$-alkoxy, halo-$(C_1-C_6)$-alkoxy and $(C_1-C_6)$-alkoxy-$(C_1-C_4)$-alkyl;

$R^2$ is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, halo-$(C_2-C_6)$-alkenyl, $(C_2-C_6)$-alkynyl, $(C_2-C_6)$-alkynyloxy, halo-$(C_2-C_6)$-alkynyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl each substituted by u radicals selected from the group consisting of methyl, ethyl, methoxy, trifluoromethyl and halogen;

$R^3$ and $R^4$ are each independently hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, $(C_3-C_7)$-halocycloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_1-C_6)$-alkoxy-$(C_1-C_4)$-alkyl, halogen, nitro or cyano;

$R^5$ is hydrogen or fluorine;

$R^6$ is acetoxy, acetamido, N-methylacetamido, benzoyloxy, benzamido, N-methylbenz-amido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_3-C_6)$-cycloalkyl, or heteroaryl, heterocyclyl or phenyl each substituted by u radicals selected from the group consisting of methyl, ethyl, methoxy, trifluoromethyl and halogen;

$R^7$ and $R^8$ are each independently hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, halo-$(C_3-C_7)$-cycloalkyl, $-OR^9$, $S(O)_m R^9$, $(C_1-C_6)$-alkylthio, halo-$(C_1-C_6)$-alkylthio, $(C_1-C_6)$-alkylsulfinyl, halo-$(C_1-C_6)$-alkylsulfinyl, $(C_1-C_6)$-alkylsulfonyl, halo-$(C_1-C_6)$-alkyl-sulfonyl, $(C_1-C_6)$-alkoxy-$(C_1-C_4)$-alkyl, halogen, nitro, cyano, heteroaryl, heterocyclyl or phenyl, where the three latter radicals are each substituted by u radicals selected from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkylthio, $(C_1-C_6)$-alkylsulfinyl, $(C_1-C_6)$-alkylsulfonyl, $(C_1-C_6)$-alkoxy, halo-$(C_1-C_6)$-alkoxy and $(C_1-C_6)$-alkoxy-$(C_1-C_4)$-alkyl, or $R^7$ and $R^8$ together with the carbon atom to which they are bonded form a $-X^1-(CH_2)_r-X^2-$, $-(CH_2)_s-X^3-$, $-(CH_2)_t-X^3-CH_2-$, $-(CH_2)_v-X^3-CH_2CH_2-$ or $-(CH_2)_w-$ unit in which each of the $(CH_2)$ groups is substituted by m radicals selected from the group consisting of halogen, methyl and $(C_1-C_3)$-alkoxy, or $R^7$ and $R^8$ together with the carbon atom to which they are bonded form the $-O-N((C_1-C_3)$-alkyl)-$CHR^{10}-CH_2-$ or $-O-N=CR^{10}-CH_2-$ unit in which each of the $(CH_2)$ groups is substituted by m radicals selected from the group consisting of halogen and methyl;

$R^9$ is hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, $(C_3-C_7)$-halocycloalkyl, $(C_3-C_7)$-cycloalkyl-$(C_1-C_3)$-alkyl, halo-$(C_3-C_7)$-cycloalkyl-$(C_1-C_3)$-alkyl, heteroaryl, heterocyclyl or phenyl, where the three latter radicals are each substituted by s radicals selected from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkylthio, $(C_1-C_6)$-alkylsulfinyl, $(C_1-C_6)$-alkylsulfonyl, $(C_1-C_6)$-alkoxy, halo-$(C_1-C_6)$-alkoxy and $(C_1-C_6)$-alkoxy-$(C_1-C_4)$-alkyl;

$R^{10}$ is hydrogen, $(C_1-C_3)$-alkyl, or phenyl substituted by u radicals selected from the group Consisting of $(C_1-C_3)$-alkyl, halogen, cyano and nitro;

$R^{11}$ is hydrogen, $(C_1-C_6)$-alkyl, $(C_2-C_6)$-alkenyl, $(C_2-C_6)$-alkynyl, formyl, $(C_2-C_6)$-alkylcarbonyl, $(C_2-C_6)$-alkoxycarbonyl or $(C_1-C_2)$-alkylsulfonyl;

X and Y are independently O, S, SO, $SO_2$, C=O, C=S, $NR^{10}$, $CR^7R^8$, C=$NOR^{10}$ or C=$NN(R^{11})_2$;

$X^1$ and $X^2$ are each independently O, S or N($(C_1-C_3)$-alkyl);

$X^3$ is O or S;

m is 0, 1 or 2;

n is 2;

r is 2, 3 or 4;

s is 2, 3, 4 or 5;

t is 1, 2, 3 or 4;

u is 0, 1, 2 or 3;

v is 2 or 3; and w is 2, 3, 4, 5 or 6.

2. An N-(1,2,5-oxadiazol-3-yl)—, N-(tetrazol-5-yl)- or N-(triazol-5-yl)bicycloarylcarboxamide as claimed in claim 1, in which $R^1$ is $(C_1-C_3)$-alkyl, $(C_3-C_5)$-cycloalkyl, halo-$(C_1-C_3)$-alkyl or $(C_1-C_3)$-alkoxy-$(C_1-C_3)$-alkyl;

$R^2$ is hydrogen, $(C_1-C_3)$-alkyl, $(C_3-C_5)$-cycloalkyl, halo-$(C_1-C_3)$-alkyl, $(C_1-C_3)$-alkoxy, halo-$(C_1-C_3)$-alkoxy, cyano, nitro, methylsulfenyl, methylsulfinyl, methylsulfonyl, acetylamino, methoxycarbonyl, ethoxycarbonyl, halogen, amino, aminocarbonyl, methylaminocarbonyl, dimethylaminocarbonyl or methoxymethyl;

$R^3$ and $R^4$ are each independently hydrogen, $(C_1-C_3)$-alkyl, halo-$(C_1-C_3)$-alkyl, $(C_3-C_5)$-cycloalkyl, $(C_1-C_3)$-alkoxy, $(C_1-C_3)$-haloalkoxy, $(C_1-C_6)$-alkylthio, $(C_1-C_6)$-alkylsulfinyl, $(C_1-C_6)$-alkylsulfonyl, $(C_1-C_6)$-alkoxy-$(C_1-C_4)$-alkyl, halogen, nitro or cyano;

$R^5$ is hydrogen;

$R^7$ and $R^8$ are each independently hydrogen, $(C_1-C_3)$-alkyl, halo-$(C_1-C_3)$-alkyl, $(C_3-C_5)$-cycloalkyl, $-OR^9$, $-S(O)_m R^9$, $(C_1-C_3)$-alkylthio, $(C_1-C_3)$-alkylsulfinyl, $(C_1-C_3)$-alkylsulfonyl, $(C_1-C_3)$-alkoxy-$(C_1-C_3)$-alkyl, halogen, nitro, cyano, heteroaryl, heterocyclyl or phenyl, where the three latter radicals are each substituted by u radicals selected from the group consisting of halogen, nitro, cyano, $(C_1-C_3)$-alkyl, halo-$(C_1-C_3)$-alkyl, $(C_3-C_5)$-cycloalkyl, $(C_1-C_3)$-alkylthio, $(C_1-C_3)$-alkylsulfinyl, $(C_1-C_3)$-alkylsulfonyl, $(C_1-C_3)$-alkoxy, halo-$(C_1-C_3)$-alkoxy and $(C_1-C_3)$-alkoxy-$(C_1-C_3)$-alkyl, or $R^7$ and $R^8$ together with the carbon atom to which they are bonded form a $-X^1-(CH_2)_r-X^2-$, $-(CH_2)_s-X^3-$, $-(CH_2)_t-X^3-CH_2-$, $-(CH_2)_v-X^3-CH_2CH_2-$ or $-(CH_2)_w-$ unit in which each of the $(CH_2)$ groups is substituted by m radicals selected from the group consisting of halogen, methyl and $(C_1-C_3)$-alkoxy, or R⁷ and R⁸ together with the carbon atom to which they are bonded form the —O—N((C₁-C₃)-alkyl)-CHR¹⁰—CH₂— or —O—N=CR¹⁰—CH₂— unit in which each of the (CH₂) groups is substituted by m radicals selected from the group consisting of halogen and methyl;

R⁹ is hydrogen, (C₁-C₃)-alkyl, halo-(C₁-C₃)-alkyl, (C₂-C₃)-alkenyl, (C₂-C₄)-alkynyl, (C₃-C₅)-cycloalkyl, (C₃-C₅)-cycloalkyl-(C₁-C₃)-alkyl, heteroaryl, heterocyclyl or phenyl, where the three latter radicals are each substituted by s radicals selected from the group consisting of halogen, nitro, cyano, (C₁-C₃)-alkyl, halo-(C₁-C₃)-alkyl, (C₃-C₆)-cycloalkyl, (C₁-C₃)-alkylthio, (C₁-C₃)-alkylsulfinyl, (C₁-C₃)-alkylsulfonyl, (C₁-C₃)-alkoxy, halo-(C₁-C₃)-alkoxy and (C₁-C₃)-alkoxy-(C₁-C₃)-alkyl;

R¹⁰ is hydrogen or (C₁-C₃)-alkyl;

X and Y are each independently O, SO₂, C=O, C=S, CR⁷R⁸, C=NOR¹⁰;

X¹ and X² are each independently O, S, N(CH₃);

X³ is O or S;

m is 0, 1 or 2;

n is 2;

r is 2 or 3;

s is 2, 3 or 4;

t is 1, 2 or 3;

u is 0, 1 or 2;

v is 2 or 3; and w is 2, 3, 4 or 5.

3. A herbicidal composition, comprising a herbicidally active content of at least one compound of the formula (I) as claimed in claim 1.

4. The herbicidal composition as claimed in claim 3, in a mixture with at least one formulation auxiliary.

5. A herbicidal composition as claimed in claim 3 additionally comprising at least one pesticidally active substance selected from the group consisting of an insecticide, an acaricide, a further herbicide, a fungicide, a safener and a growth regulator.

6. The herbicidal composition as claimed in claim 5, comprising a safener.

7. A herbicidal composition as claimed in claim 6, comprising cyprosulfamide, cloquintocet-mexyl, mefenpyr-diethyl or isoxadifen-ethyl.

8. A herbicidal composition as claimed in claim 5, comprising a further herbicide.

9. The compound of formula (I) and/or a salt thereof as claimed in claim 1 capable of being used for controlling an unwanted plant.

10. The compound of formula (I) and/or a salt thereof as claimed in claim 1, wherein said compound of formula (I) is capable of being used for controlling an unwanted plant in a crop of a useful plant.

11. The compound of formula (I) capable of being used as claimed in claim 10, wherein said useful plant is a transgenic useful plant.

12. The compound of formula (I) and/or a salt thereof as claimed in claim 2, capable of being used for controlling an unwanted plant.

13. A herbicidal composition as claimed in claim 3 capable of being used for controlling an unwanted plant.

14. An N-(tetrazol-5-yl)bicycloarylcarboxamide as claimed in claim 1 having the formula

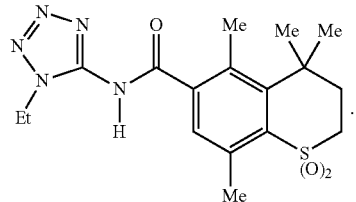

15. An N-(tetrazol-5-yl)bicycloarylcarboxamide as claimed in claim 1 having the formula

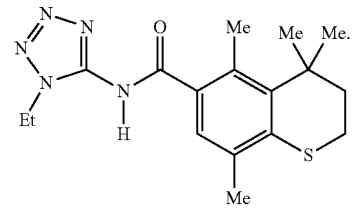 [SMILES: CCn1nnnc1NC(=O)c1cc(C)c2c(c1C)C(C)(C)CCS2]

16. An N-(tetrazol-5-yl)bicycloarylcarboxamide as claimed in claim 1 having the formula

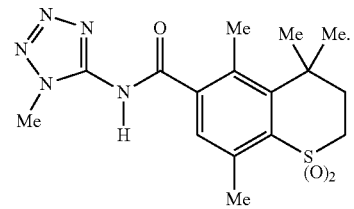

17. An N-(tetrazol-5-yl)bicycloarylcarboxamide as claimed in claim 1 having the formula

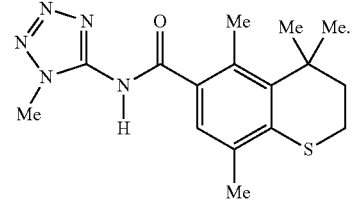

18. An N-(tetrazol-5-yl)bicycloarylcarboxamide as claimed in claim 1 having the formula

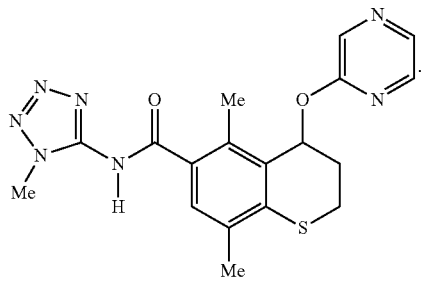 [SMILES: Cc1cc(C(=O)Nc2nnnn2C)c(C)c2c1SCCC2Oc1cnccn1]

* * * * *